United States Patent
Beck et al.

(10) Patent No.: US 6,174,912 B1
(45) Date of Patent: Jan. 16, 2001

(54) NITROGEN SUBSTITUTED IMIDAZO[4,5-C] PYRAZOLES AS CORTICOTROPIN RELEASING HORMONE ANTAGONISTS

(75) Inventors: James P. Beck, Smyrna; Paul J. Gilligan, Wilmington, both of DE (US)

(73) Assignee: DuPont Pharmaceuticals Company, Wilmington, DE (US)

( * ) Notice: Under 35 U.S.C. 154(b), the term of this patent shall be extended for 0 days.

(21) Appl. No.: 09/138,460

(22) Filed: Aug. 21, 1998

Related U.S. Application Data

(60) Provisional application No. 60/056,735, filed on Aug. 22, 1997.
(51) Int. Cl.$^7$ .................. A61K 31/4162; C07D 231/00; C07D 235/00; C07D 487/04
(52) U.S. Cl. ....................... 514/393; 548/303.4
(58) Field of Search .......................... 514/393; 548/303.4

(56) References Cited

FOREIGN PATENT DOCUMENTS

| 190457 A1 | 12/1985 | (EP) . |
| 190457 | * 8/1986 | (EP) . |
| 407102 A1 | 6/1990 | (EP) . |
| 778277 A1 | 11/1999 | (EP) . |
| 9111999 | 8/1991 | (WO) . |
| 9510506 | 6/1994 | (WO) . |
| 9533727 | 5/1996 | (WO) . |
| 9534563 | 5/1996 | (WO) . |

OTHER PUBLICATIONS

Damasio, *Alzheimer's Disease And Related Dementias*, Cecil Textbook of Medicine, 20th Edition, vol. 2, pp. 1992–1996.*
France et al., *CSF Corticotropin–Releasing Factor–Like Immunoactivity in Chronic Pain Patients With and Without Major Depression*, 1988, pp. 86–88.
Koob, George F, *Stress, Cortcotropin–Releasing Factor, and Behavior*, 1985, pp. 39–52.
Vale et al., *Chemical and Biological Charcterization of Corticotropin Releasing Factor*, 1983, pp. 245–270.
Britton et al., *Corticotropin Releasing Factor and Amphetamine Exaggerate Partial agonist Properties of Benzodiazepine Antagonist Ro 15–1788 in the Conflict Test*, 1988, pp. 306–311.
Britton et al., *Chlordiazepoxide Attenuates Responses Suppression Induced by Corticotropin–Releasing Factor in the Conflict Test*, 1985, pp. 147–152.
Swerdlow et al., *Corticotropin–Releasing Factor Potentiates Acoustics Startle in Rats: Blockade by Chlordiazepoxide*, 1986, pp. 147–152.
DeSouza et al., *Corticotropin–Releasing Factor Receptors are Widely Distributed Within the Rat Central Nervous System: An Autoradiographic Study*, Dec. 1985, pp. 3189–3203.
Arato et al., *Elevated CSF CRF in Suicide Victims*, 1989, pp. 355–359.

Holsboer et al., *ACTH and Multistereroid Responses Factor Enchances Behavioral Effects of Novelty*, 1982, pp. 363–367.
Berridge et al., *Corticotropin–Releasing Factor Elicits Naloxone Sensitive Stress–Like Alterations in Exploratoty Behavior in Mice*, Aug. 1986, 83–93.
Dunn et al., *Phsiological and Behaviroal Responses to Corticotropin–Releasing Factor Administration: Is CRF a Mediator of Anxiety or Stress Responses?*, 1990, pp. 71–100.
Koob et al., *Behavioral Effects of Corticotropin–Releasing Factor*, 1989, pp. 253–265.
Sapolsky, R.M., *Hypercortisolism among Socially Subordinate Wild Baboons Orginates at the CNS Level*, Nov. 1989, pp. 1047–1054.
Nemeroff et al., *reduced Corticotropin Releasing factor Binding Sites in the Frontal Cortex of Suicide Victims*, Jun. 1988, pp. 577–579.
Blalock, J. Edwin, *A Molecular Basis for Bidirectional Communication Between the Immune and Neuroendocine Systems*, Jan. 1989, pp. 1–32.
Berridge et al., *A Corticotropin–Releasing Factor Antagonist Reverse the Stress–Induced Changes of Exploratory Behavior in Mice*, 1987, pp. 393–401.

(List continued on next page.)

* cited by examiner

Primary Examiner—Mukund J. Shah
Assistant Examiner—Deepak R. Rao
(74) Attorney, Agent, or Firm—Blair Q. Ferguson

(57) ABSTRACT

Corticotropin releasing factor (CRF) antagonists of Formulae (I) or (II):

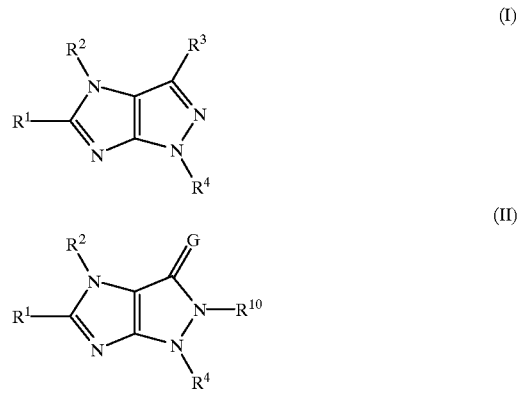

and their use in treating psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress.

11 Claims, No Drawings

OTHER PUBLICATIONS

Gold et al., *Psychiatric Implications of Basic and Clinical Studies With Corticotropin–Releasing Factor*, May 1984, pp. 619–627.

Grigoriadis et al., *Effects of Chronic Antidepressant and Benzodiazepine Treatment on Corticotropin–Releasing–Factor Receptors in Rat Brain and Pituitary*, 1989, pp. 53–60.

Nemeroff et al., *Elevated Concentrations of CSF Corticotropin–Releasing Factor–Like Immunoreactivity in Depressed Patients*, 1984, pp. 1342–1344.

Vale et al., *Characterization of a 41–Residue Ovine Hypothalamic Peptide That Stimulates Secretion of Corticotropin and β–Endorpin*, Sept. 1981, pp. 1394–1397.

Banki et al., *CSF Corticotropin–Releasing Factor–Like Immunoreactivity in Depression and Schizophrenia*, Jul. 1987, pp. 873–877.

Morley et al., *Neuropeptides: Conductors of the Immune Orchestra*, 1987, pp. 527–544.

Rivier et al., *Characterization of Rat Hypothalamic Cortitropin–Releasing Factor*, Aug. 1983, pp. 4851–4855.

NITROGEN SUBSTITUTED IMIDAZO[4,5-C] PYRAZOLES AS CORTICOTROPIN RELEASING HORMONE ANTAGONISTS

This application claims the benefit of U.S. Provisional Application No. 60/056,735, filed Aug. 22, 1997.

FIELD OF THE INVENTION

This invention relates to novel nitrogen substituted imidazo[4,5-c]pyrazole compounds and pharmaceutical compositions, and to methods for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. In particular, the present invention relates to novel imidazopyrimidines and imidazopyridines, pharmaceutical compositions containing such compounds and their use in treating psychiatric disorders, neurological diseases, immunological, cardiovascular or heart-related diseases and colonic hypersensitivity associated with psychopathological disturbance and stress.

BACKGROUND OF THE INVENTION

Corticotropin releasing hormone or factor (herein referred to as CRH or CRF), a 41 amino acid peptide, is the primary physiological regulator of proopiomelanocortin(POMC)-derived peptide secretion from the anterior pituitary gland [J. Rivier et al., *Proc. Nat. Acad. Sci.* (*USA*) 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF-neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9–41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist ($\alpha$-helical CRF$_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

Several publications describe corticotropin releasing factor antagonist compounds and their use to treat psychiatric disorders and neurological diseases. Examples of such publications include DuPont Merck PCT application US94/11050, Pfizer WO 95/33750, Pfizer WO 95/34563, Pfizer WO 95/33727 and Pfizer EP 778277 A1.

European Patent Application Number 190457 A1 discloses 3-methyl-imidazo [4,5-c] pyrazole derivatives which have the general formula shown below. The compounds have an intense depressant activity on the central nervous system, including anticonvulsant, sedative, analgesic and hypothermizing.

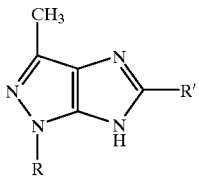

Similar imidazo[4,5-c]pyrazole derivatives are disclosed in *Tetrahedron*, Vol. 46, pp. 5777–5788 (1990).

European Patent Application Publication Number 407102A discloses angiotensin II antagonists having the general formula:

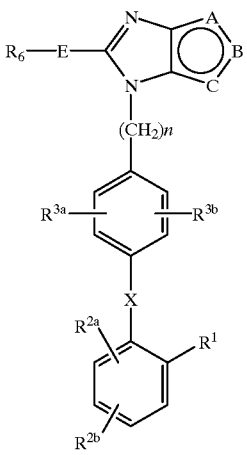

PCT Patent Application WO 91/11999 discloses angiotensin II antagonists having the general formula shown below. These compounds also have utility as treatments for cognitive dysfunctions, depression, anxiety and dysphoric mental states.

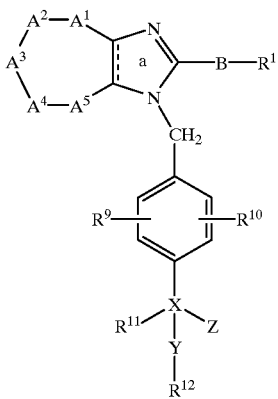

Insofar as is known, novel nitrogen substituted imidazo[4,5-c]pyrazoles, which are described in detail below, have not been previously reported as corticotropin releasing factor antagonist compounds useful in the treatment of psychiatric disorders and neurological diseases, including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress.

SUMMARY OF THE INVENTION

In accordance with one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

According to another aspect, the present invention provides novel compounds of formulae (I) and (II) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of formulae (I) and (II), and methods of using such compounds for the suppression of CRF hypersecretion, and/or for the treatment-of anxiogenic disorders.

According to yet another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, and disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in mammals.

According to a still further aspect of the invention, the compounds provided by this invention (and especially labelled compounds of this invention) are also useful as standards and reagents in determining the ability of a potential pharmaceutical to bind to the CRF receptor.

DETAILED DESCRIPTION OF THE INVENTION

[1] Thus, in a first embodiment, the present invention provides novel compounds of Formulae (I) and (II):

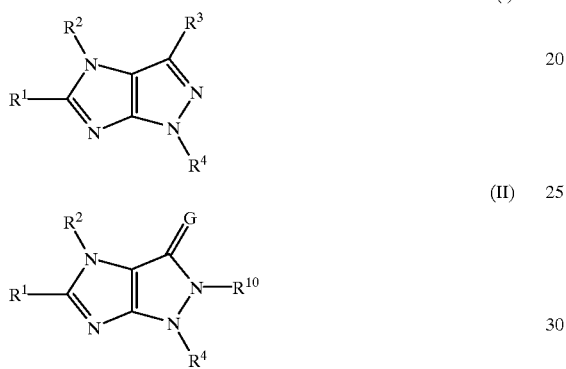

or isomers thereof, stereoisomeric forms thereof, or mixtures of stereoisomeric forms thereof, and pharmaceutically acceptable salt forms thereof, wherein:

$R^1$ is selected from H, $C_1$–$C_6$ alkyl, $C_2$–$C_6$ alkenyl, $C_2$–$C_6$ alkynyl, $C_1$–$C_6$ haloalkyl, where such haloalkyl is substituted with 1–6 halogens, $C_3$–$C_6$ cycloalkyl, $C_4$–$C_8$ cycloalkylalkyl, C1–C6 alkoxy, aryl, heteroaryl or heterocyclyl;

$R^2$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, where each group can be optionally substituted with 1 to 3 substituents independently selected at each occurrence from $C_1$–$C_6$ alkyl, $C_3$–$C_{10}$ alkenyl, $C_3$–$C_{10}$ alkynyl, $C_3$–$C_6$ cycloalkyl, aryl, heteroaryl, heterocyclyl, halogen, cyano, $NR^6R^7$, $OR^7$, thiol, $S(O)_nR^9$, $COR^7$, $CO_2R^7$, $OC(O)R^9$, $NR^8COR^7$, $NR^8CONR^6R^7$, $NR^8CO_2R^9$, $CONR^6R^7$;

or $S(O)_nR^9$, $COR^7$, $CO_2R^7$, $CONR^6R^7$;

or $C_1$–$C_4$ haloalkyl, where $C_1$–$C_4$ haloalkyl may be substituted with 1–6 halogens;

or aryl or aryl($C_1$–$C_4$ alkyl), heteroaryl or heteroaryl ($C_1$–$C_4$ alkyl), heterocyclyl, or heterocyclyl($C_1$–$C_4$ alkyl), wherein $C_1$–$C_4$ alkyl in aryl($C_1$–$C_4$ alkyl), heteroaryl($C_1$–$C_4$ alkyl) or heterocyclyl($C_1$–$C_4$ alkyl) is optionally substituted with substituents selected from $C_1$–$C_8$ alkyl, $COR^7$, $CO_2R^7$, $S(O)_nR^9$, cyano and aryl;

n is independently at each occurrence 0, 1, or 2;

$R^3$ is H, $C_1$–$C_6$ alkyl, $C_2$–$C_6$ alkenyl, $C_2$–$C_6$ alkynyl, $C_1$–$C_6$ haloalkyl, where such haloalkyl is substituted with 1–6 halogens, $C_3$–$C_6$ cycloalkyl, $C_2$–$C_{10}$ alkoxyalkyl, $C_1$–$C_6$ hydroxyalkyl, cyano, $OR^6$, thiol, $S(O)_nR^9$, $NR^6R^7$, aryl, or heteroaryl;

$R^4$ is phenyl, pyridyl, pyrimidyl, triazinyl, furanyl, naphthyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, 2,3-dihydrobenzofuranyl, 2,3-dihydrobenzothienyl, 1,2-benzopyranyl, 3,4-dihydro-1,2-benzopyranyl or pyrazolyl, where each $R^4$ is attached via an unsaturated carbon atom and each $R^4$ may be optionally substituted with 1 to 4 $R^5$ groups;

$R^5$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, where $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl are optionally substituted with 1–3 substituents independently selected at each occurrence from $C_1$–$C_4$ alkyl, nitro, halogen, cyano, $NR^6R^7$, $NR^8COR^7$, $NR^8CO_2R^9$, $COR^7$, $OR^7$, $CONR^6R^7$, $NR^8CONR^6R^7$, $CO_2R^7$, thiol, or $S(O)_nR^9$;

or nitro, halogen, cyano, $C_1$–$C_4$ haloalkyl optionally substituted with 1–6 halogens, $NR^6R^7$, $NR^8COR^7$, $NR^8CO_2R^9$, $COR^7$, $OR^7$, $CONR^6R^7$, $NR^8CONR^6R^7$, $CO_2R^7$, thiol, or $S(O)_nR^9$;

$R^6$ and $R^7$ are independently at each occurrence selected from:

(1) H;

(2) $C_1$–$C_{10}$ alkyl, $C_3$–$C_{10}$ alkenyl, $C_3$–$C_{10}$ alkynyl, $C_2$–$C_8$ alkoxyalkyl, $C_3$–$C_6$ cycloalkyl, or $C_4$–$C_{12}$ cycloalkylalkyl, each optionally substituted with 1–6 substituents independently selected at each occurrence from $C_1$–$C_6$ alkyl, $C_3$–$C_6$ cycloalkyl, halogen, $C_1$–$C_4$ haloalkyl, cyano, nitro, $OR^{12}$, thiol, $S(O)_nR^9$, $COR^{12}$, $CO_2R^{12}$, $NR^8COR^{12}$, $NR^8CONR^{11}R^{12}$, $NR^8CO_2R^9$, $NR^{11}R^{12}$, and $CONR^{11}R^{12}$;

(3) aryl, aryl($C_1$–$C_4$ alkyl), heteroaryl or heteroaryl ($C_1$–$C_4$ alkyl), heterocyclyl, or heterocyclyl($C_1$–$C_4$ alkyl);

$R^8$ is independently at each occurrence selected from H, $C_1$–$C_4$ alkyl, C3–C8 alkenyl, $C_3$–$C_6$ cycloalkyl, or $C_4$–$C_7$ cycloalkylalkyl;

or phenyl or phenyl (C1–C4 alkyl), each optionally substituted with 1–3 substitutents selected from C1–C4 alkyl, halogen, C1–C4 haloalkyl optionally substituted with 1–6 halogens, C1–C4 alkoxy, OH;

$R^9$ is independently at each occurrence selected from H, $C_1$–$C_4$ alkyl, $C_2$–$C_4$ alkoxyalkyl, $C_3$–$C_6$ cycloalkyl, $C_4$–$C_7$ cycloalkylalkyl;

or phenyl or phenyl(C1–C4 alkyl), each optionally substituted with 1–3 substitutents selected from C1–C4 alkyl, halogen, C1–C4 haloalkyl optionally substituted with 1–6 halogens, C1–C4 alkoxy, OH;

$R^{10}$ is H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl), heteroaryl, heteroaryl($C_1$–$C_4$ alkyl), heterocyclyl, heterocyclyl ($C_1$–$C_4$ alkyl), where C1–C4 haloalkyl is optionally substituted with 1 to 6 halogens;

$R^{11}$ and $R^{12}$ are independently at each occurrence selected from H, $C_1$–$C_6$ alkyl, $C_3$–$C_6$ cycloalkyl, $C_4$–$C_7$ cycloalkylalkyl, or $C_1$–$C_4$ haloalkyl optionally substituted with 1–6 halogens;

or
  phenyl or phenyl(C1–C4 alkyl), each optionally substituted with 1–3 substitutents selected from C1–C4 alkyl, halogen, C1–C4 haloalkyl optionally substituted with 1–6 halogens, C1–C4 alkoxy, OH;

aryl is phenyl or naphthyl, each optionally substituted with 1 to 5 substituents independently selected at each occurrence from $R^{13}$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl, 2,3-dihydrobenzofuranyl, 2,3-dihydrobenzothienyl, or indazolyl, each optionally substituted with 1 to 4 substituents independently selected from at each occurrence $R^{13}$;

heterocyclyl is saturated or partially saturated heteroaryl, optionally substituted with 1 to 3 substituents independently selected at each occurrence from $R^{13}$;

$R^{13}$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, where $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl are optionally substituted with 1–3 substituents independently selected at each occurrence from $C_1$–$C_4$ alkyl, nitro, halogen, cyano, $NR^8R^9$, $NR^8COR^9$, $NR^8CO_2R^9$, $COR^9$, $OR^9$, $CONR^8R^9$, $NR^8CONR^8R^9$, $CO_2R^9$, thiol, or $S(O)_nR^9$ or nitro, halogen, cyano, $C_1$–$C_4$ haloalkyl optionally substituted with 1–6 halogens, $NR^8R^9$, $NR^8COR^9$, $NR^8CO_2R^9$, $COR^9$, $OR^9$, $CONR^8R^9$, $NR^8CONR^8R^9$, $CO_2R^9$, thiol, or $S(O)_nR^9$;

[2] In a preferred embodiment, the present invention provides novel compounds of Formulae (I) and (II) wherein: $R^4$ is phenyl, pyridyl or pyrimidyl, each optionally substituted by 1 to 4 $R^5$ groups.

[3] In a more preferred embodiment, the present invention provides novel compounds of Formula (I) and (II), wherein: $R^1$ is selected from H, $C_1$–$C_6$ alkyl, $C_1$–$C_6$ haloalkyl, where such haloalkyl is substituted with 1–6 halogens, $C_3$–$C_6$ cycloalkyl, or aryl.

[4] In an even more preferred embodiment, the present invention provides novel compounds of Formulae (I) and (II), wherein: $R^1$ is selected from H, $C_1$–$C_6$ alkyl, $C_1$–$C_6$ haloalkyl, where such haloalkyl is substituted with 1–6 halogens, $C_3$–$C_6$ cycloalkyl, or aryl and $R^4$ is phenyl, pyridyl or pyrimidyl, each optionally substituted by 1 to 4 $R^5$ groups.

[5] In an even further preferred embodiment, the present invention provides novel compounds of Formula (I) and (II), wherein the compound is selected from the group:

1-(2-chloro-4-trifluoromethyl)phenyl-5-ethyl-3-methyl-4-[1-(1-methyl)butane]imidazo[4,5-c]pyrazole;
1-(2-chloro-4-trifluoromethyl)phenyl-5-ethyl-4-[1-(1-ethyl)butane]-3-methylimidazo[4,5-c]pyrazole;
4-(n-butyl)-1-(2-chloro-4-bromo)phenyl-5-ethyl-3-methylimidazo[4,5-c]pyrazole;
1-(2-chloro-4-bromo)phenyl-5-ethyl-3-methyl-4-[1-(1-methyl)butane]imidazo[4,5-c]pyrazole;
1-(2-chloro-4-bromo)phenyl-5-ethyl-4-[1-(1-ethyl)butane]3-methylimidazo[4,5-c]pyrazole;
5-ethyl-3-fluoromethyl-4-[1-(1-methyl)butane]-1-(2,4,6-trichloro)phenylimidazo[4,5-c]pyrazole;
5-ethyl-4-[1-(1-methyl)butane]-1-(2,4,6-trichloro)phenylimidazo[4,5-c]pyrazole;
1-(2,6-dichloro-4-bromo)phenyl-5-ethyl-4-[1-(1-ethyl)butane]-3-methylimidazo[4,5-c]pyrazole;
1-(2,4-dichloro)phenyl-5-ethyl-4-[1-(1-ethyl)butane]-3-methylimidazo[4,5-c]pyrazole;
1-(2,4-dichloro)phenyl-5-ethyl-3-methyl-4-[1-(1-methyl)butane]imidazo[4,5-c]pyrazole;
1-(2,4-dichloro)phenyl-5-ethyl-3-methyl-4-[1-(1,3-dimethyl)butane]imidazo[4,5-c]pyrazole;
1-(2,6-dichloro-4-bromo)phenyl-5-ethyl-3-methyl-4-[1-(1-methyl)butane]imidazo[4,5-c]pyrazole;
5-ethyl-4-[-1-(1-ethyl)butane]-3-methyl-1-(2,4,5-trichloro)phenylimidazo[4,5-c]pyrazole;
5-ethyl-3-methyl-4-[1-(1-methyl)butane]-1-(2,4,5-trichloro)phenylimidazo[4,5-c]pyrazole;
5-ethyl-4-[1-(1-methyl)pentane]-3-methyl-1-(2,4,6-trichloro)phenylimidazo[4,5-c]pyrazole;
1-(2-bromo-4-isopropyl)phenyl-5-ethyl-4-[1-(1-ethyl)butane]-3-methylimidazo[4,5-c]pyrazole;
1-(2-bromo-4-isopropyl)phenyl-5-ethyl-3-methyl-4-[1-(1-methyl)butane)imidazo[4,5-c]pyrazole;
1-(2-bromo-4,6-dichloro)phenyl-5-ethyl-4-[1-(1-ethyl)butane]-3-methylimidazo[4,5-c]pyrazole;
1-(2-bromo-4,6-dichloro)phenyl-5-ethyl-3-methyl-4-[1-(1-methyl)butane]imidazo[4,5-c]pyrazole;
4-(n-butyl)-1-(2,6-dichloro-4-bromo)phenyl-5-ethyl-3-methylimidazo[4,5-c]pyrazole;
1-(2,6-dichloro-4-bromo)phenyl-5-ethyl-3-methyl-4-[1-(3-methyl)butane]imidazo(4,5-c]pyrazole;
1-(2,6-dichloro-4-bromo)phenyl-5-ethyl-4-[1-(2-ethyl)butane]-3-methylimidazo[4,5-c]pyrazole;
4-benzyl-1-(2,6-dichloro-4-bromo)phenyl-5-ethyl-3-methylimidazo[4,5-c]pyrazole; and
1-(2,6-dichloro-4-bromo)phenyl-4-(3,4-difluorobenzyl)-5-ethyl-3-methylimidazo[4,5-c]pyrazole or a pharmaceutically acceptable salt form thereof.

[6, 7, 8, 9, 10] In another preferred embodiment, the present invention provides a pharmaceutical composition comprising a pharmaceutically acceptable carrier and a therapeutically effective amount of compounds of Formulae (I) and (II).

[11, 12, 13, 14, 15] In yet another preferred embodiment, the present invention provides a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals, comprising: administering to the mammal a therapeutically effective amount of compounds of Formulae (I) and (II).

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-propoxy, "Cycloalky" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4- thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids,such as those disclosed in, for example, Roberts and Vellaccio (1983) *The Peptides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., $=O$) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

The term "therapeutically effective amount" of a compound of this invention means an amount effective to antagonize abnormal level of CRF or treat the symptoms of affective disorder, anxiety or depression in a host.

Synthesis

The novel substituted bicyclic imidazo[4,5-c]pyrazoles of Formulae (I) and (II) of this invention can be prepared by one of the general schemes outlined below, in particular Schemes 1–2.

Compounds of Formula (I) of this invention may be prepared as shown in Scheme 1.

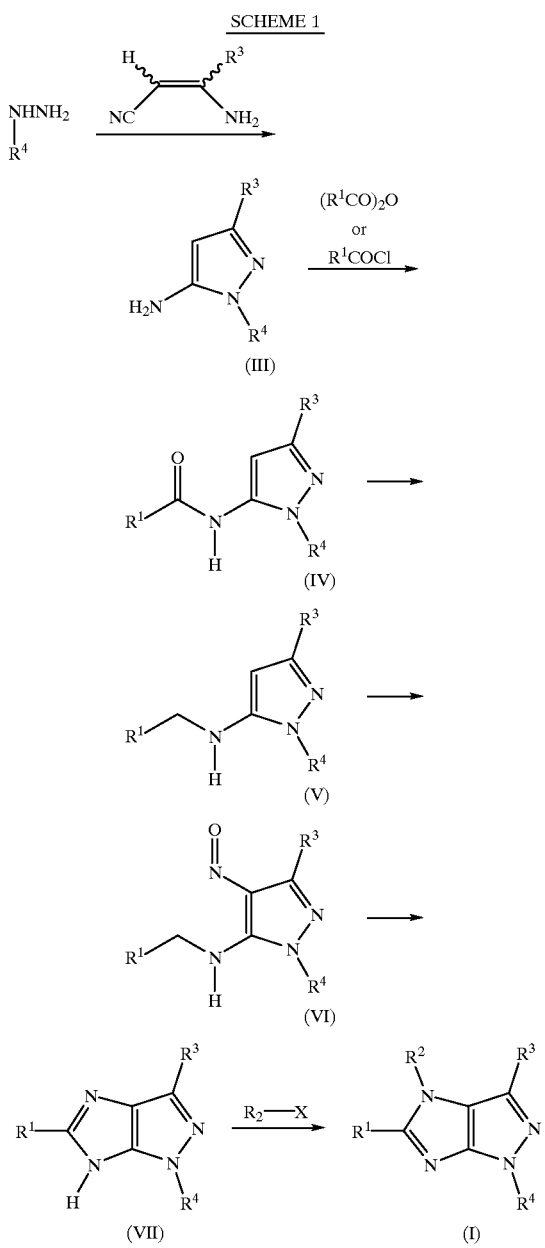

An appropriate hydrazine ($R^4NHNH_2$), either as the free base or as the corresponding mineral acid salt, may be condensed with acrylonitrile compounds of formula $R^3(NH_2)C=C(CN)H$ to afford pyrazole compounds of formula (III). These cyclizations are preferably conducted in aqueous media and at elevated temperatures up to boiling.

When $R^3$ is hydrogen, 2-halogenoacrylonitrile compounds of formula $CH_2=CH(CN)Hal$ or 2,3-dihalogenopropionitrile compounds of formula Hal'$CH_2CH$(CN)Hal may be cyclized with the hydrazines of formula $R^4NHNH_2$. Hal and Hal' may be independently selected from chlorine, bromine or iodine. One skilled in the art of heterocyclic chemistry will readily understand the optimal combinations of conversions necessary to prepare a number of compounds of formula (III) with $R^3$ and $R^4$ variations and can refer to the review of Potts, K. T. (*Comprehensive Heterocyclic Chemistry*, Katritzky, A. R., et.al., Eds., Pergamon Press, Oxford, 1984, 5, pg. 111–157) or Vicentini, et.al. (*Tetrahedron*, 1990, 46, 5777).

Compounds of formula (III) may be readily condensed with compounds of formula $(R^1CO)_2O$ or $R^1COCl$ to provide amides of formula (IV). The condensations may be conducted neat or in the optional presence of cosolvent. The reactions are preferably run at room temperature where $R^1$ is methyl and at elevated temperature up to the boiling point of the anhydride or cosolvent used where $R^1$ is larger than methyl. Amides of formula (IV) may then be converted, in the presence of a reducing agent, to the substituted amino pyrazoles of formula (V). Reducing agents include, but are not limited to, lithium aluminum hydride and borane. Reactions are generally run in ethereal solvents, for example tetrahydrofuran and diethyl ether. The reductions are carried out for a period of time between 1 hour and 4 days, and at room temperature or elevated temperature up to reflux in order to effect the reaction. If borane is used, it may be employed as a complex, for example, but not limited to, borane-methyl sulfide complex, borane-piperidine complex, borane-pyridine complex, and borane-tetrahydrofuran complex.

In preparation for ring closure to the imidazole, compounds of formula (V) may be nitrosated in the presence of acid and a suitable nitrosating agent such as, but not limited to, isoamyl nitrite in an alcoholic solvent such as methanol, ethanol, or isopropanol. The reactions are generally conducted at room temperature and afford compounds of formula (VI) in high yield and purity after filtration or column chromatography. Cyclization to imidazopyrazoles of formula (VII) may be accomplished by refluxing precursors of formula (VI) in the presence of a base such as, but not limited to, pyridine or other non-nucleophilic organic base for a period of time between 1 hour and 3 days and at a temperature ranging from room temperature up to the boiling point of the base or co-solvent employed. Cosolvents such as, but not limited to, tetrahydrofuran may be used, however, it may be preferable to conduct the cyclizations in the absence of cosolvent. Compounds of formula (VII) are expected to exist as a mixture of imidazole tautomers, and one skilled in the art will immediately recognize this.

Finally, treatment of compounds of formula (VII) with a base and a compound of formula $R^2$-X wherein X represents a leaving group may afford the desired imidazopyrazole compounds of formula (I). Leaving groups may include, but are not limited to, bromo, chloro, iodo, cyano, alkoxy, methanesulfonyl, and p-toluenesulfonyl. Possible bases include, but are not limited to, the sodium, lithium or potassium bis(trimethylsilyl)amides, sodium or potassium hydride, alkyl lithiums and alkyl grignards and inorganic bases such as sodium, potassium and lithium hydroxide. The reactions are optionally conducted at room temperature or at elevated temperatures up to the boiling point of a cosolvent. A wide variety of inert solvents may be employed, for example, dimethylformamide, dimethylsulfoxide, toluene, tetrahydrofuran, diethyl ether, and methylene chloride. The reactions may be successfully performed in glass reaction vessels or polypropylene wells, and one skilled in the art of organic chemistry will readily understand the optimal combinations of above conditions for effecting this transformation, or can consult the text of Larock, R. C. (*Comprehensive Organic Transformations*, VCH Publishers, New York, 1989). Although regiomeric alkylation products are conceivably possible from tautomers of formula (VII), the experimental conditions taught herein will selectively provide the desired regiomer represented by compounds of formula (I).

Alternatively, compounds of formula (I) may be formed from compounds of formula (VII) by treatment with a base and subsequent addition to the carbon-carbon double bond of an α, β-unsaturated carboxylic acid derivative, ketone, aldehyde, or nitrile; a process commonly accepted as the Michael reaction. Bases and optional inert cosolvents may be selected from those identified (vide supra). One skilled in the art of organic synthesis will readily appreciate the utility of the Michael reaction, and may consult the teachings of House, H. O. (*Modern Synthetic Reactions*, W. A. Benjamin, Inc., Menlo Park, Calif., 1972, p 595).

As shown in Scheme 2, compounds of formula (I) where $R^3$ is OH or SH may be transformed into compounds of formula (I) where $R^3$ is $OR^6$ or $SR^6$ or compounds of formula (II) where G is O or S and the pyrazole nitrogen is substituted as $R^{10}$.

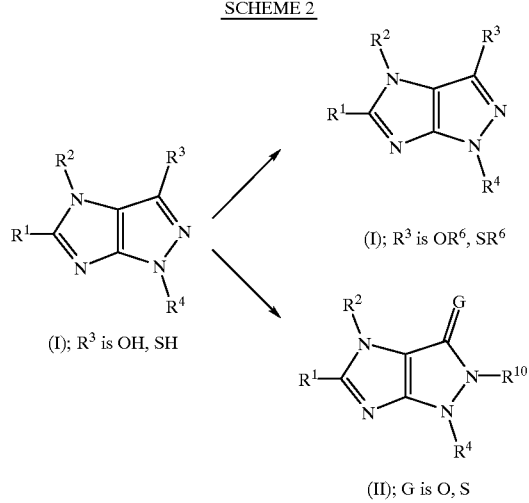

Reactions to afford compounds of formula (I) where $R^3$ is $OR^6$ or $SR^6$ may be preferably conducted with oxophilic alkylating agents such as, but not limited to, the trialkyloxonium tetrafluoroborates and/or thiophilic alkylating agents such as, but not limited to, dialkyl sulfates. Reactions to afford compounds of formula (II), where G is O or S and the pyrazole nitrogen is 10 substituted (Scheme 2) as $R^{10}$ are more preferably effected by treatment of compounds of formula (I, $R^3$ is OH or SH) with a base such as, but not limited to, potassium hydroxide in a solvent such as acetone or other inert solvent with a reagent $R^{10}$-X where X is a leaving group (vide supra). These product compounds arise via the tautomeric nature of compounds of formula (I) where $R^3$ is OH or SH.

In the described manner then, the novel substituted bicyclic imidazo[4,5-c]pyrazoles of formula (I) and (II) of this invention can be prepared by one of the general schemes outlined above. See Schemes 1–2.

Compounds of Formula (II) may also be prepared as outlined in Scheme 3.

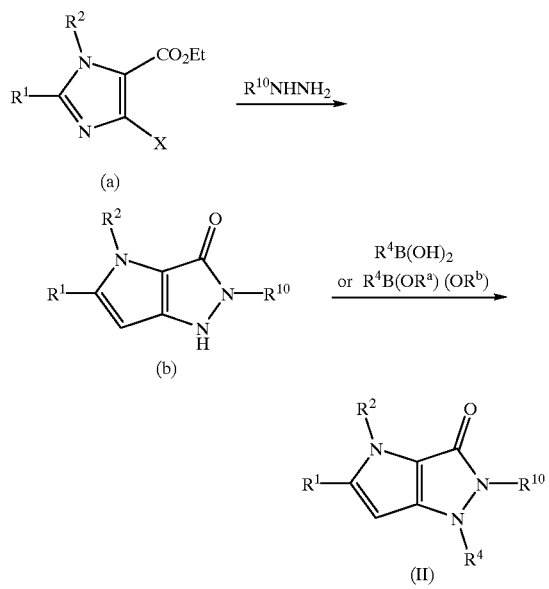

Imidazoles of Formula (a) (where X=halogen, $NH_2$, alkylamino (1–6 carbons), dialkylamino (2–12 carbons), alkylthio (1 to 6 carbons) or alkylsulfonyl (1 to 6 carbons) may be reacted with a compound of the formula $R^{10}NHNH_2$, in the presence or absence of a base, in an inert solvent to give intermediates of formula (b). Bases may include, but are not limited to, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20 to 100° C.

Intermediates (b) may then be treated with a boronic acid or a boronic acid ester of the formula $R^4B(OH)_2$ or $R^4B(OR^a)(OR^b)$ (where $R^a$ and $R^b$ are lower alkyl(1 to 6 carbons) or together $R^a$ and $R^b$ are lower alkylene (2 to 12 carbons) in the presence of a metal catalyst with or without a base in an inert solvent to give compounds of Formula (II). Metal catalysts include, but are not limited to salts or phosphine complexes of Cu, Pd or Ni (e.g. $Cu(OAc)_2$, $PdCl_2(PPh_3)_2$, $NiCl_2(PPh_3)_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 150° C.

Alternatively, compounds of Formula (II) may be prepared as outlined in Scheme 4.

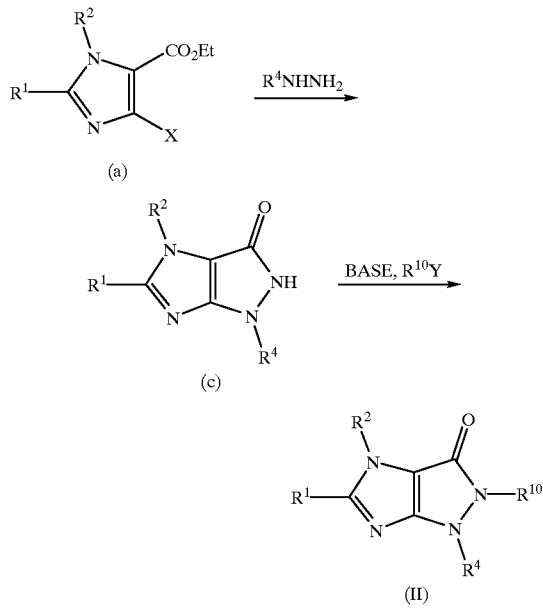

Imidazoles of Formula (a) (where X is defined above) may be treated with compounds of the formula $R^4NHNH_2$ to yield intermediates (c) in the presence or absence of a base in an inert solvent. Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 150° C.

Intermediates (c) may then be treated with a reagent of the Formula $R^{10}X$ to give compounds of Formula (II) in the presence or absence of a base in an inert solvent. Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 150° C.

The following examples are provided to describe the invention in further detail. These examples, which set forth the best mode presently contemplated for carrying out the invention, are intended to illustrate and not to limit the invention.

EXAMPLE 1

Preparation of 4-Cyclopropylmethyl-3,5-dimethyl-1-(2,4,6-trichloro)phenylimidazo[4,5-c]pyrazole Step A: β-Aminocrotononitrile (14.68 g, 0.18 mol) was dissolved in 1.0N HCl (500 ml) and treated with 2,4,6-trichlorophenylhydrazine (36 g, 0.17 mol). The reaction was refluxed 4 h, cooled, and decanted into a 2 liter beaker. The solution was diluted with water (250 ml) and neutralized with 10% NaOH. The resultant precipitate was filtered and dried to constant weight to afford 44.71 g (95%) of the desired aminopyrazole as a white crystalline solid, mp 135.5–136.0° C. $^1$H NMR (300 MHz, CDCl$_3$) δ 7.48 (s, 2H), 5.50 (s, 1H), 3.48 (bs, 2H), 2.25 (s, 3H). Anal. Calcd. for $C_{10}H_8N_3Cl_3$: C, 43.43; H, 2.92, N, 15.19. Found: C, 43.56; H, 2.92; N, 15.09.

Step B: The product from Part A (14.0 g, 0.05 mol) was suspended in acetic anhydride (40 ml) and allowed to stir at room temperature. The reaction became homogeneous after 20 minutes and was stirred 40 additional minutes, then transferred to a slurry of ice (600 ml). The resultant precipitate was stirred 1 h, filtered and dried to constant weight, affording 14.22 g (88%) of acetylated product, mp 210.0–211.0° C. $^1$H NMR (300 MHz, CDCl$_3$) δ 7.50 (s, 2H), 6.81 (bs, 1H), 6.47 (s, 1H), 2.33 (s, 3H), 2.08 (s, 3H). Anal. Calcd. for $C_{12}H_{10}N_3Cl_3O_1$: C, 45.24; H, 3.16; N, 13.19. Found: C, 45.52; H, 3.18; N, 13.10.

Step C: The product from Part B (16.63 g, 0.05 mmol) was dissolved in dry tetrahydrofuran (100 ml) under an atmosphere of nitrogen, and treated with borane/THF complex (156 ml, 0.15 mol) via addition funnel. Upon completion of addition, the reaction was brought to reflux for 48 hours. The reaction was cooled, treated with 10% NaOH (100 ml), and stirred 1 h. The heterogeneous mixture was diluted with water (400 ml) and diethyl ether (350 ml) and transferred to a separatory funnel. The mixture was partitioned and the aqueous layer reextracted with diethyl ether (2×100 ml). The combined organic extracts were dried over anhydrous magnesium sulfate, filtered and concentrated in-vacuo. Column chromatography on silica gel (450 g), eluting with hexanes/ethyl acetate (2/1) afforded the substituted amino pyrazole, 5.89 g (c. 40%) as a white crystalline solid, mp 81.5–83.5° C. $^1$H NMR (300 MHz, CDCl$_3$) δ 7.47 (s, 2H), 5.38 (s, 1H), 3.14 (m, 2H), 3.03 (bs, 1H), 2.26 (s, 3H), 1.19 (t, 3H, J=7.0 Hz). Anal. Calcd. for $C_{12}H_{12}N_3Cl_3$: C, 47.32; H, 3.97; N, 13.80. Found: C, 47.41; H, 4.01; N, 13.56.

Step D: The product from Step C (7.78 g, 25.54 mmol) was dissolved in ethanol (100 ml), cooled to 0° C., and treated with 1.0N HCl (0.5 ml) and isoamyl nitrite (3.42 ml, 25.54 mmol). The reaction was stirred 5 hours before final concentration in-vacuo to remove solvent. Purification via column chromatography (600 g) eluting with hexanes/ethyl acetate (1/2) yielded a violet crystalline solid, 7.14 g (87%), mp 180.0–181.0° C. $^1$H NMR (300 MHz, CDCl$_3$) δ 7.50 (s, 2H), 2.84 (m, 2H), 2.73 (s, 3H), 1.14 (t, 3H, J=7.3 Hz). Anal. Calcd. for $C_{12}H_{11}N_4Cl_3O_1$: C, 43.20; H, 3.32; N, 16.79. Found: C, 43.06; H, 3.26; N, 16.54.

Part E: The product from Part D (7.82 g, 0.023 mol) was dissolved in pyridine (50 ml) and the homogeneous solution refluxed 8 hours. The reaction was concentrated in-vacuo to remove pyridine and purified via column chromatography (600 g) eluting initially with ethyl acetate/hexanes (1/2) and then with ethyl acetate to afford desired imidazopyrazole, 1.71 g (c. 25%), mp 245° C. (dec.). $^1$H NMR (300 MHz, CDCl$_3$) δ 9.20 (bs, 1H), 7.42 (s, 2H), 2.52 (s, 3H), 2.44 (s, 3H). MS (CI) M+H=315.

Part F: The product from Part E (0.10 g, 0.32 mmol) was charged to a dry flask, dissolved in anhydrous dimethylformamide (5.0 ml), and treated with sodium hydride (0.03 g, 0.70 mmol). After stirring 5 minutes, the crimson reaction was quenched with cyclopropylmethylbromide (77 μl, 0.80 mmol). The reaction was heated to 100° C. and allowed to stir 30 minutes, whereupon the reaction returned to a golden yellow color. After dilution with water (30 ml) the reaction was extracted with ethyl acetate (4×15 ml). The combined organic extracts were dried over anhydrous magnesium sulfate and concentrated in-vacuo. Purification on silica gel (30 g) eluting with ethyl acetate/hexanes (2/1) gave 50.3 mg of the title compound, mp 190.0–192.0° C. $^1$H NMR (300 MHz, CDCl$_3$) δ 7.43 (s, 2H), 3.94 (d, 2H, J=7.5 Hz), 2.52 (s, 3H), 2.50 (s, 3H), 1.26 (m, 1H), 0.71 (m, 2H), 0.40 (m, 2H). HRMS calcd. for M+H ($C_{16}H_{16}N_4Cl_3$): 369.0441. Found: 369.0446.

EXAMPLE 3

Preparation of 3,5-Dimethyl-4-[1-(2-ethyl)butane]-1-(2,4,6-trichloro) phenylimidazo[4,5-c]pyrazole The product from Example 1, Part E (61 mg, 0.19 mmol) was reacted with sodium hydride (19 mg, 0.48 mmol) and 1-bromo-2-ethylbutane (108 μl, 0.77 mmol) in dimethylformamide (2.0 ml) as described for the preparation of Example 1, Part F. Title compound: mp 112.0–114.5° C. $^1$H NMR (300 MHz, CDCl$_3$) δ 7.44 (s, 2H), 3.89 (d, 2H, J=7.3 Hz), 2.51 (s, 3H), 2.48 (s, 3H), 1.8 (m, 1H), 1.39 (m, 4H), 0.95 (m, 6H). HRMS calcd. for M+H ($C_{18}H_{22}N_4Cl_3$): 399.0910. Found: 399.0896.

Examples 2 and 4–9 given in TABLE 1 may be prepared in the same manner as described for the preparation of Examples 1 and 3, starting with the product from Example 1, Part E and substituting the appropriate electrophile.

EXAMPLE 11

Preparation of 4-Benzyl-3,5-dimethyl-1-(2,4,6-trimethyl)phenylimidazo[4,5-c]pyrazole Step A: β-Aminocrotononitrile (11.96 g, 0.15 mol) was dissolved in 1.0N HCl (350 ml) and treated with 2,4,6-trimethylphenylhydrazine, hydrochloride (25.89 g, 0.14 mol). The reaction was refluxed 4 h, cooled, and decanted into a 2 liter beaker. The solution was diluted with water (250 ml) and neutralized with 10% NaOH. The resultant precipitate was filtered and dried to constant weight to afford 27.82 g (93%) of the desired aminopyrazole as a white crystalline solid, mp 127–129° C. $^1$H NMR (CDCl$_3$) δ 6.93 (s, 2H), 5.42 (s, 1H), 3.4 (bs, 2H), 2.31 (s, 3H), 2.23 (s, 3H), 2.02 (s, 6H).

Step B: The product from Part A (10.0 g, 46.40 mmol) was suspended in acetic anhydride (35 ml) and allowed to stir at room temperature. The reaction became homogeneous after 20 minutes and was stirred 40 additional minutes, then transferred to a slurry of ice (500 ml). The resultant precipitate was stirred 2 h, filtered and dried to constant weight, affording 8.14 g (68%) of acetylated product, $^1$H NMR (CDCl$_3$) δ 6.98 (s, 2H), 6.78 (bs, 1H), 6.52 (s, 1H), 2.34 (s, 3H), 2.31 (s, 3H), 2.04 (s, 3H), 1.96 (s, 6H).

Step C: The product from Step B (8.1 g, 31.47 mmol) was dissolved in anhydrous THF (80 ml) and treated with lithium aluminum hydride (63 ml, 62.94 mmol, 1.0 M/THF) under nitrogen at room temperature. The reaction was stirred 1.5 h at room temperature and 1.0 h at 50° C., and quenched by the addition of 10% sodium hydroxide (10 ml). The heterogeneous slurry was filtered through celite with copious diethyl ether washings. The filtrate was concentrated in-vacuo and purified by column chromatography on silica gel (250 g), eluting with hexanes/ethyl acetate (1/1) to provide the desired product, 7.3 g (95%) as a crystalline solid.

Step D: The product from Step C (7.3 g, 29.99 mmol) was dissolved in ethanol (50 ml), cooled to 0° C., and treated with 1.0 N HCl (14 drops) and isoamyl nitrite (4.02 ml, 29.99 mmol). The reaction was stirred 10 minutes, warmed to room temperature, and stirred an additional 5 hours. The reaction was concentrated in-vacuo to remove ethanol and purified by column chromatography on silica gel (600 g) eluting with hexanes/ethyl acetate (2/1) to afford a violet crystalline solid, 7.14 g (87%). $^1$H NMR (CDCl$_3$) δ 9.95 (bs, 1H), 6.94 (s, 2H), 2.70 (s, 3H), 2.69 (q, 2H, J=7.2 Hz), 2.33 (s, 3H), 2.10 (s, 6H), 1.03 (t, 3H, J=7.3 Hz).

Step E: The product from Step D (7.14 g, 26.21 mmol) was dissolved in anhydrous pyridine (50 ml) and brought to reflux for 8 hours. The reaction was then concentrated in-vacuo to dryness and directly purified by column chromatography on silica gel (600 g) eluting with ethyl acetate/hexanes (2/1) to afford a dark solid, 1.24 g (19%), mp 191–193° C. $^1$H NMR (CDCl$_3$) δ 9.54 (bs, 1H), 6.87 (s, 2H), 2.39 (s, 3), 2.38 (s, 3H), 2.27 (s, 3H), 1.99 (s, 6H).

Stet F: The product from Part E (0.125 g, 0.49 mmol) was charged to a dry flask, dissolved in anhydrous dimethylformamide (7.0 ml), and treated with sodium hydride (0.05 g, 1.22 mmol). After stirring 30 minutes, the dark reaction was quenched with benzylbromide (234 μl, 1.96 mmol). The reaction was heated to 50° C. and allowed to stir 1 hour, whereupon the reaction returned to a golden yellow color. After dilution with water (40 ml) the reaction was extracted with ethyl acetate (4×15 ml). The combined organic extracts were dried over anhydrous magnesium sulfate and concentrated in-vacuo. Purification on silica gel (40 g) eluting with ethyl acetate/hexanes (1/1) gave 83.8 mg (50%) of the title compound, mp 88–89° C. $^1$H NMR (300 MHz, CDCl$_3$) δ 7.4 (m, 3H), 7.15 (d, 2H, J=8.0 Hz), 6.90 (s, 2H), 5,24 (m, 2H), 2.47 (s, 3H), 2.29 (s, 3H), 2.20 (s, 3H), 2.01 (s, 3H). HRMS calcd. for M+H (C$_{22}$H$_{25}$N$_4$): 345.2079. Found: 345.2061.

Examples 6–10 and 12–36 given in TABLE 1 may be prepared in the same manner as described for the preparation of Example 11, starting with the product from Example 11, Part E, and substituting the appropriate electrophile.

TABLE 1

| Ex. | R$^1$ | R$^2$ | R$^3$ | R$^4$ | R$^5$ | mp ° C. |
|---|---|---|---|---|---|---|
| 1 | CH$_2$cPr | Cl | Cl | Cl | H | 190–192 |
| 2 | CH(CH$_2$CH$_3$)$_2$ | Cl | Cl | Cl | H | 210–212 |
| 3 | CH$_2$CH(CH$_2$CH$_3$)$_2$ | Cl | Cl | Cl | H | 112–114 |
| 4 | benzyl | Cl | Cl | Cl | H | Amorphous |
| 5 | n-butyl | Cl | Cl | Cl | H | 176–177 |
| 6 | 4-fluorobenzyl | Cl | Cl | Cl | H | |
| 7 | 4-phenylbenzyl | Cl | Cl | Cl | H | |
| 8 | CH$_2$(2-tetrahydropyran) | Cl | Cl | Cl | H | |
| 9 | CH$_2$CH$_2$OCH$_2$CH$_3$ | Cl | Cl | Cl | H | |
| 10 | CH$_2$CH(CH$_2$CH$_3$)$_2$ | Me | Me | Me | H | Oil, MS |
| 11 | benzyl | Me | Me | Me | H | 88–89 |
| 12 | n-butyl | Me | Me | Me | H | 122–123 |
| 13 | CH$_2$(2-tetrahydropyran) | Me | Me | Me | H | |
| 14 | COPh | Me | Me | Me | H | |
| 15 | CH$_2$cPr | Cl | Cl | H | H | 106–107 |
| 16 | CH$_2$cPr | H | Cl | H | H | 130–134 |
| 17 | benzyl | Cl | Cl | Br | H | |
| 18 | benzyl | Br | Cl | Br | H | |
| 19 | benzyl | Cl | OMe | OMe | H | |
| 20 | benzyl | Br | OMe | OMe | H | |
| 21 | n-butyl | Et | Br | Et | H | |
| 22 | n-butyl | Et | Me | Et | H | |
| 23 | CH$_2$cPr | Me | OMe | H | H | |
| 24 | CH$_2$cPr | Me | Cl | H | H | |
| 25 | CH(CH$_2$CH$_3$)$_2$ | Br | iPr | H | H | |
| 26 | CH(CH$_2$CH$_3$)$_2$ | Br | Br | H | H | |
| 27 | CH(CH$_2$CH$_3$)$_2$ | Cl | OMe | H | H | |
| 28 | CH(CH$_2$CH$_3$)$_2$ | Cl | Me | Me | H | |
| 29 | benzyl | Cl | Me | Me | H | |
| 30 | CH$_2$CH$_2$OCH$_2$CH$_3$ | Cl | Me | Me | H | |
| 31 | CH$_2$cPr | Cl | Cl | H | Cl | |
| 32 | CH(CH$_2$CH$_3$)$_2$ | Me | Cl | H | Cl | |
| 33 | CH$_2$CH(CH$_2$CH$_3$)$_2$ | Br | Me | H | Cl | |
| 34 | benzyl | Cl | Cl | H | F | |
| 35 | n-butyl | Cl | Me | H | F | |
| 36 | CH(CH$_3$)CH$_2$CH$_2$CH$_3$ | Me | Me | H | F | |

EXAMPLE 38

Preparation of 5-Ethyl-3-methyl-4-[1-(2-ethyl) butane]-1-(2,4,6-trichloro) phenylimidazo[4,5-c] pyrazole Part A: The product from Example 1, Part A (15 g, 54.23 mmol) was suspended in propionic anhydride (40 ml) and allowed to stir at room temperature for 2 hours. The reaction was poured onto an ice slurry (500 ml) and stirred overnight. The resultant precipitate was filtered and dried to constant weight to afford 16.02 g (89%) of desired amido pyrazole.

Part B: The product from Part A (15.92 g, 47.86 mmol) was reduced with borane/THF complex (144 ml) in the same manner as described for the preparation of Example 1, Part C to afford an oil, 5.65 g (56%, based on recovered starting material). $^1$H NMR (300 MHz, CDCl$_3$) δ 7.47 (s, 2H), 5.36 (s, 1H), 3.08 (bs, 1H), 3.05 (m, 2H), 2.26 (s, 3H), 1.57 (m, 2H), 0.92 (s, 3H, J=7.8 Hz).

Part C: The product from Step B (10.50 g, 32.97 mmol) was dissolved in ethanol (75 ml), cooled to 0° C., and treated with 1.0N HCl (0.5 ml) and isoamyl nitrite (4.41 ml, 32.97 mmol). The reaction was stirred 24 hours, cooled to 0° C. and the resultant purple precipitate filtered and dried to constant weight to afford 8.64 g (75%). $^1$H NMR (300 MHz, CDCl$_3$) δ 7.51 (s, 2H), 2.74 (m, 2H), 2.3 (s, 3H), 1.48 (m, 2H), 0.85 (t, 3H, J=7.2 Hz).

Part D: The product from Part C (8.47 g, 24.36 mmol) was dissolved in pyridine (140 ml) and the homogeneous solution refluxed 14 hours. The reaction was concentrated in-vacuo to remove pyridine and purified via column chromatography on silica gel (800 g) eluting initially with ethyl acetate/hexanes (1/1) to remove unreacted starting material, and then with ethyl acetate to afford desired imidazopyrazole, 2.87 g (36%), mp 221.0–223.0° C. $^1$H NMR (300 MHz, CDCl$_3$) δ 8.82 (bs, 1H), 7.44 (s, 2H), 2.85 (q, 2H, J=7.8 Hz), 2.46 (s, 3H), 1.37 (t, 3H, J=7.5 Hz).

Part E: The product from Part D (0.10 g, 0.30 mmol) was reacted with sodium hydride (30 mg, 0.75 mmol) and 1-bromo-2-ethylbutane (170 μl, 1.20 mmol) in dimethylformamide (2.0 ml) as described for the preparation of Example 1, Part F. Title compound: mp 135.5–136.0° C. $^1$H NMR (300 MHz, CDCl$_3$) δ 7.44 (s, 2H), 3.89 (d, 2H, J=7.2 Hz), 2.77 (q, 2H, J=7.5 Hz), 2.51 (s, 3H), 1.80 (m, 1H), 1.38 (m, 7H), 0.94 (t, 3H, 7.5 Hz).

EXAMPLE 40

Preparation of 4-Cyclopropylmethyl-5-ethyl-3-methyl-1-(2,4,6-trichloro)phenylimidazo[4,5-c] pyrazole The product from Example 38, Part D (0.02 g, 0.06 mmol) was reacted with sodium bis(trimethylsilyl)amide (152 μl, 0.09 mmol, 0.6M/toluene) and cyclopropylmethylbromide (11.8 μl, 0.12 mmol) in dimethylformamide (0.6 ml) in a 2.0 ml polypropylene well confined within a 96 well microtiter plate. The reaction was agitated for 1 hour at room temperature, heated for 30 minutes at 60° C., then treated with aminomethylpolystyrene (180 mg, 0.180 mmol, Advanced ChemTech, 1.00 mmol/g loading, Lot #13312) for 1 hour. The reaction was filtered, dried to constant weight, and purified on a silica gel plug (0.70 g) eluting with a solvent gradient from hexanes/ethyl acetate (9/1) to hexanes/ethyl acetate (1/1) to afford title compound, 18.2 mg, mp 144.5–146.0° C. $^1$H NMR (300 MHz, CDCl$_3$) δ 7.44 (s, 2H), 3.94 (d, 2H, J=6.6 Hz), 2.79 (q, 2H, J=7.2 Hz), 2.52 (s, 3H), 1.59 (s, 6H), 1.35 (t, 3H, J=7.2 Hz), 1.26 (m, 1H), 0.66 (m, 2H), 0.40 (m, 2H). MS (CI) M+H=313.1.

EXAMPLE 10

Preparation of 5-Ethyl-3-methyl-4-[1-(1-n-propyl) butane]-1-(2,4,6-trichloro) phenylimidazo[4,5-c] pyrazole The product from Example 38, Part D (50 mg, 0.15 mmol) was reacted with sodium bis(trimethylsilyl)amide (630 μl, 0.38 mmol, 0.6M/toluene) and 4-bromoheptane (11.8 μl, 0.12 mmol) in dimethylformamide (1.5 ml). The reaction was heated to 60° C. for 3 hours, then diluted with water (10 ml) and extracted with ethyl acetate (3×15 ml). The combined organic extracts were dried over anhydrous magnesium sulfate, concentrated in-vacuo and the crude product purified by column chromatography on silica gel (20 g) eluting with hexanes/ethyl acetate (1/1) to afford the title compound as a crystalline solid, mp 113–114° C. $^1$H NMR (300 MHz, CDCl$_3$) δ 7.44 (s, 2H), 4.10 (m, 1H), 2.83 (q, 2H, J=7.3 Hz), 2.54 (s, 3H), 1.84 (q, 4H, J=7.7 Hz), 1.34 (t, 3H, J=7.2 Hz), 1.20 (m, 4H), 0.91 (t, 3H, J=7.4 Hz). HRMS calcd. for M+($C_{20}H_{26}N_4Cl_3$): 426.1145. Found: 426.1130.

EXAMPLE 106

Preparation of 5-Ethyl-3-methyl-4-[1-(1-ethyl) pentane]-1-(2,4,6-trichloro) phenylimidazo[4,5-c] pyrazole The product from Example 38, Part D (200 mg, 0.61 mmol) was reacted with sodium bis(trimethylsilyl)amide (2.50 ml, 1.52 mmol, 0.6M/toluene) and 3-bromoheptane (435 μg, 2.43 mmol) in dimethylformamide (6.0 ml) as described for the preparation of Example 99. Title compound was obtained as a crystalline solid, mp 121–122° C. $^1$H NMR (300 MHz, CDCl$_3$) δ 7.44 (s, 2H), 3.99 (m, 1H), 2.81 (q, 2H, J=7.3 Hz), 2.53 (s, 3H), 1.88 (m, 4H), 1.35 (t, 3H, J=7.3 Hz), 1.29 (m, 4H), 0.86 (t, 3H, J=6.9 Hz), 0.84 (t, 3H, J=6.7 Hz). HRMS calcd. for M+H ($C_{20}H_{26}N_4Cl_3$): 427.1223. Found: 427.1213.

EXAMPLE 107

Preparation of 5-Ethyl-3-methyl-4-[1-(1-methyl) propane]-1-(2,4,6-trichloro) phenylimidazo[4,5-c] pyrazole The product from Example 38, Part D (200 mg, 0.61 mmol) was reacted with sodium bis(trimethylsilyl)amide (2.50 ml, 1.52 mmol, 0.6M/toluene) and 2-bromobutane (260 μl, 2.43 mmol) in dimethylformamide (6.0 ml) as described for the preparation of Example 105. Title compound was obtained as a crystalline solid, mp 113–114° C. $^1$H NMR (300 MHz, CDCl$_3$) δ 7.45 (s, 2H), 4.2 (m, 1H), 2.83 (q, 2H, J=7.3 Hz), 2.56 (s, 3H), 1.91 (m, 2H), 1.57 (d, 3H, J=6.6 Hz), 1.33 (t, 3H, J=7.3 Hz), 0.86 (t, 3H, J=7.3 Hz). HRMS calcd. for M+H ($C_{17}H_{20}N_4Cl_3$): 385.0754. Found: 385.0743.

EXAMPLE 108

Preparation of 5-Ethyl-3-methyl-4-[1-(1-methyl) butane]-1-(2,4,6-trichloro) phenylimidazo[4,5-c] pyrazole The product from Example 38, Part D (200 mg, 0.61 mmol) was reacted with sodium bis(trimethylsilyl)amide (2.50 ml, 1.52 mmol, 0.6M/toluene) and 2-bromopentane (300 μl, 2.43 mmol) in dimethylformamide (6.0 ml) as described for the preparation of Example 105. Title compound was obtained as a viscous oil. $^1$H NMR (300 MHz, CDCl$_3$) δ 7.44 (s, 2H), 4.30 (m, 1H), 2.56 (s, 3H), 1.86 (m, 2H), 1.55 (d, 3H, J=6.9 Hz), 1.33 (t, 3H, J=7.3 Hz), 0.93 (t, 3H, J=7.3 Hz). HRMS calcd. for M+H ($C_{18}H_{22}N_4Cl_3$): 399.0910. Found: 399.0901.

EXAMPLE 113

Preparation of 5-Ethyl-4-methanesulfonylbenzyl-3-methyl-1-(2,4,6-trichloro)phenylimidazo[4,5-c] pyrazole:

The product from Example 38, Part D (0.02 g, 0.06 mmol) was reacted with sodium bis(trimethylsilyl)amide (152 μl, 0.09 mmol, 0.6M/toluene) and 4-methylsulfonylbenzyl chloride (121 μl, 0.12 mmol as a 1.0 M solution in DMF) in dimethylformamide (0.6 ml) in a 2.0 ml polypropylene well as described for the preparation of Example 40. Title compound was obtained as a crystalline solid, mp 194.0–196.0° C. $^1$H NMR (300 MHz, CDCl$_3$) δ 7.98 (d, 2H, J=8.1 Hz), 7.46 (s, 2H), 7.32 (d, 2H, J=8.1 Hz), 5.36 (s, 2H), 3.07 (s, 3H), 2.78 (q, 2H, J=7.7 Hz), 2.19 (s, 3H), 1.32 (t, 3H, J=7.7 Hz). HRMS calcd. for M+1 ($C_{21}H_{20}N_4O_2Cl_3S_1$): 497.0373. Found: 497.0343.

EXAMPLE 114

Preparation of 4-Benzoyl-5-ethyl-3-methyl-1-(2,4,6-trichloro)phenylimidazo [4,5-c]pyrazole The product from Example 38, Part D (200 mg, 0.61 mmol) was dissolved with gentle heating in anhydrous methylene chloride (5 ml) and treated with 4-dimethylaminopyridine (15 mg, 0.12 mmol), diisopropylethylamine (160 μl, 0.92 mmol) and benzoyl chloride (78 μl, 0.67 mmol). The reaction was stirred 1.5 hours at room temperature, concentrated directly in-vacuo and purified by column chromatography on silica gel (50 g) eluting with hexanes/ethyl acetate (2/1) to afford desired product, 189 mg (71%) as a crystalline solid, mp 169.0–170.0° C. $^1$H NMR (300 MHz, CDCl$_3$) δ 7.85 (d, 2H, J=8.0 Hz), 7.75 (m, 1H), 7.59 (t, 2H, J=8.1 Hz), 7.48 (s, 2H), 3.10 (q, 2H, J=7.3 Hz), 1.54 (s, 3H), 1.38 (t, 3H, J=7.3 Hz). HRMS calcd. for M+ ($C_{20}H_{15}N_4Cl_3O_1$): 432.0311. Found: 432.0291. Anal. Calcd. for $C_{20}H_{15}N_4Cl_3O_1$: C, 55.39: H, 3.50; N, 12.92. Found: C, 55.65; H, 3.46; N, 12.52.

EXAMPLE 115

Preparation of 4-Benzenesulfonyl-5-ethyl-3-methyl-1-(2,4,6-trichloro)phenyl imidazo[4,5-c]pyrazole The product from Example 38, Part D (200 mg, 0.61 mmol) was dissolved with gentle heating in anhydrous methylene chloride (5 ml) and treated diisopropylethylamine (160 μl, 0.92 mmol) and benzenesulfonyl chloride (86 μl, 0.67 mmol). The reaction was stirred 20 hours at room temperature, concentrated directly in-vacuo and purified by column chromatography on silica gel (55 g) eluting with hexanes/ethyl acetate (2/1) to afford desired product, 150 mg (53%) as a crystalline solid, mp 189.0–190.0° C. $^1$H NMR (300 MHz, CDCl$_3$) δ 7.90 (d, 2H, J=8.8 Hz), 7.72 (m, 1H), 7.58 (t, 2H, J=8.1 Hz), 7.45 (s, 2H), 3.01 (q, 2H, J=7.3 Hz), 2.65 (s, 3H), 1.30 (t, 3H, J=7.3 Hz). HRMS calcd. for M+1 ($C_{19}H_{16}N_4O_2Cl_3S_1$): 469.0060. Found: 469.0035. Anal. Calcd. for $C_{19}H_{15}N_4Cl_3O_2S_1$: C, 48.58; H, 3.23. Found: C, 48.93, H, 3.36.

EXAMPLE 116

Preparation of 4-Diphenylmethyl-5-ethyl-3-methyl-1-(2,4,6-trichloro)phenylimidazo[4,5-c]pyrazole The compound prepared in Example 38, Part D (330 mg, 1.0 mmol) was dissolved in anhydrous dimethylformamide (10 mL), and sodium bis(trimethylsilyl)amide (0.6 M in toluene, 4.17 mL, 2.5 mmol) was added. The solution was heated to 60° C. for one hour, then bromodiphenylmethane (988 mg, 4.0 mmol) was added and the reaction held at 100° C. for 63 hours. The reaction was then cooled to room temperature, and diluted with water and diethyl ether. The layers were separated and the organic phase washed with water, dried over anhydrous magnesium sulfate, and reduced to dryness in vacuo. The residue was purified by column chromatography (25% ethyl acetate/hexanes) to give the final product as a crystalline solid (183 mg, 37%), mp $^1$H NMR (300 MHz,CDCl$_3$) δ 7.44 (s, 2H), 7.39 (m, 6H), 7.14 (m, 4H), 6.69 (s, 1H), 2.85 (q, 2H, J=7.7 Hz), 1.38 (s, 3H), 1.29 (t, 3H, J=7.5 Hz). HRMS Calcd. for M+H (C$_{26}$H$_{22}$Cl$_3$N$_4$): 495.0910. Found: 495.0883.

EXAMPLE 117

Preparation of 5-Ethyl-3-methyl-4-(1-phenylethyl)-1-(2,4,6-trichloro)phenylimidazo[4,5-c]pyrazole The compound prepared in Example Banana, Part D (200 mg, 0.61 mmol) was dissolved in anhydrous dimethylformamide (6 mL), and sodium bis(trimethylsilyl)amide (0.6 M in toluene, 2.50 mL, 1.52 mmol) was added. The solution was heated to 60° C. for one hour, then (1-bromoethyl)benzene (451 mg, 2.44 mmol) was added. The reaction was held at 100° C. for 24 hours. The reaction was then cooled to room temperature, and diluted with water and diethyl ether. The layers were separated and the organic phase washed with water, dried over anhydrous magnesium sulfate, and reduced to dryness in vacuo. The residue was purified by column chromatography (25% ethyl acetate/hexanes) to give the final product as a crystalline solid (135 mg, 31%), mp $^1$H NMR (300 MHz,CDCl$_3$) δ 7.44 (s, 2H), 7.37 (m, 3H), 7.19 (m, 2H), 2.87 (dq, 2H, J=7.4 Hz, J=1.1 Hz), 1.98 (s, 3H), 1.96 (d, 3H, J=7.0 Hz), 1.34 (t, 3H, J=7.5 Hz). HRMS Calcd. for M+H (C$_{21}$H$_{20}$Cl$_3$N$_4$): 433.0753. Found: 433.0763. Anal. Calcd. for C$_{21}$H$_{19}$Cl$_3$N$_4$: C, 58.15; H, 4.42; N, 12.92. Found: C, 58.05; H, 4.38; N, 12.73.

EXAMPLE 118

Preparation of 4-Cyclopentyl-5-ethyl-3-methyl-1-(2,4,6-trichloro)phenylimidazo[4,5-c]pyrazole The compound prepared in Example Banana, Part D (330 mg, 1.0 mmol) was dissolved in anhydrous dimethylformamide (10 mL), and sodium bis(trimethylsilyl)amide (0.6 M in toluene, 4.17 mL, 2.5 mmol) was added. The solution was heated to 60° C. for one hour, then bromocyclopentane (596 mg, 4.0 mmol) was added and the reaction held at 100° C. for 63 hours. The reaction was then cooled to room temperature, and diluted with water and diethyl ether. The layers were separated and the organic phase washed with water, dried over anhydrous magnesium sulfate, and reduced to dryness in vacuo. The residue was purified by preparative thin layer chromatography (25% ethyl acetate/hexanes) to give the final product as a crystalline solid (81 mg, 20%), mp $^1$H NMR (300 MHz,CDCl$_3$) δ 7.44 (s, 2H), 4.58 (m, 1H), 2.84 (q, 2H, J=7.6 Hz), 2.55 (s, 3H), 2.22 (m, 2H), 2.00 (m, 4H), 1.80 (m, 2H), 1.33 (t, 3H, J=7.7 Hz). HRMS Calcd. for M+H (C$_{18}$H$_{20}$Cl$_3$N$_4$): 397.0753. Found: 397.0755. Anal. Calcd. for C$_{18}$H$_{19}$Cl$_3$N$_4$: C, 54.36; H, 4.82; N, 14.09. Found: C, 54.37; H, 4.84; N, 13.82.

EXAMPLE 152

Preparation of 4-(n-Butyl)-5-ethyl-3-ethyl-1-(2,4,6-trichloro)phenylimidazo[4,5-c]pyrazole Step A: Sodium hydride (60% in mineral oil, 6.30 g, 157 mmol) was rinsed free of oil with cyclohexane, fresh cyclohexane was added (200 mL), and this suspension was heated to reflux. A solution of ethyl propionate (15.3 g, 150 mmol) and acetonitrile (6.77 g, 165 mmol) in cyclohexane (30 mL) was then added to the sodium hydride suspension over 10 minutes, the reaction was held at reflux for 16 hours, and cooled to room temperature. The reaction was extracted with water, and the resulting aqueous solution acidified to pH 4 with 10% HCl. This solution was then extracted with ethyl acetate, and the organic solution dried over anhydrous magnesium sulfate and reduced in vacuo to leave the cyanoketone as an amber oil (5.60 g, 38%). This oil was then dissolved in ethanol (500 mL), the reaction heated to 40° C., and ammonium nitrate (2.3 g, 28.8 mmol) added. Anhydrous ammonia was bubbled through the solution for 24 hours, then water (200 mL) was added and the ethanol removed in vacuo, then 0.3 N NaOH (200 mL) was added. The aqueous solution was extracted with diethyl ether, and the organic phase was dried over anhydrous magnesium sulfate and reduced in vacuo to leave the β-aminoacrylonitrile (2.82 g, 29.3 mmol, 51%). To this material was added 1N HCl (95 mL) and 2,4,6-trichlorophenylhydrazine (4.13 g, 19.5 mmol), and this mixture was refluxed for three hours. The reaction was cooled to room temperature and the supernatant aqueous phase was decanted and neutralized with 10% NaOH, producing an oil that solidifies upon stirring. The amorphous solid was recovered by filtration to give the product (5.16 g, 91%). $^1$H NMR (300 MHz,CDCl$_3$) δ 7.47 (s, 2H), 5.52 (s, 1H), 3.49 (bs, 2H), 2.61 (q, 2H, J=7.7 Hz), 1.25 (t, 3H, J=7.7 Hz). HRMS Calcd. for M+H (C$_{11}$H$_{11}$Cl$_3$N$_3$): 290.0018. Found: 289.9995. Anal. Calcd. for C$_{11}$H$_{10}$Cl$_3$N$_3$: C, 45.47; H, 3.48; N, 14.46. Found: C, 45.58; H, 3.34; N, 14.30.

Step B: The compound prepared in Step A (5.16 g, 17.8 mmol) was suspended in propionic anhydride (11.4 mL, 88.8 mmol) at room temperature and allowed to stir for 2 hours, resulting in a homogeneous solution. Ice was added and the reaction stirred for 5 hours, causing a solid to form. The off-white solid was isolated by filtration to leave the product (5.52 g, 90%), mp 145–148° C. $^1$H NMR (300 MHz,CDCl$_3$) δ 7.50(s, 2H), 6.70 (bs, 1H), 6.53 (bs, 1H), 2.70 (q, 2H, J=7.7 Hz), 2.30 (q, 2H, J=7.3 Hz), 1.29 (t, 3H, J=7.5 Hz), 1.15 (t, 3H, J=7.3 Hz). HRMS Calcd. for M+H (C$_{14}$H$_{15}$Cl$_3$N$_3$O): 346.0281. Found: 346.0280. Anal. Calcd. for C$_{14}$H$_{14}$Cl$_3$N$_3$O: C, 48.51; H, 4.07; N, 12.12. Found: C, 48.51; H,3.96; N, 12.07.

Step C: The compound prepared in Step B (5.47 g, 15.8 mmol) was dissolved in anhydrous tetrahydrofuran (50 mL). To this suspension was added borane/THF complex (47.3 mL, 47.3 mmol), and the reaction was refluxed for 16 hours. The reaction was cooled to room temperature and excess borane was quenched with 10% NaOH (15 mL) until off-gassing ceased. The reaction was diluted with water and diethyl ether, the layers separated and the organic phase washed with saturated sodium chloride, dried over anhydrous magnesium sulfate, and reduced in vacuo to leave a white solid, mp 138–140° C. $^1$H NMR (300 MHz, CDCl$_3$) δ 7.52 (s, 2H), 5.43 (s, 1H), 3.41 (m, 1H), 3.12 (q, 2H, J=6.6 Hz), 2.80 (q, 2H, J=7.7 Hz), 1.58 (m, 2H), 1.29 (t, 3H, J=7.7 Hz), 0.92 (t, 3H, J=7.5 Hz). HRMS Calcd. for M+H (C$_{14}$H$_{17}$Cl$_3$N$_3$): 332.0488. Found: 332.0485.

Step D: The compound prepared in Step C was suspended in ethanol (30 mL), and 15 drops of 10% HCl were added. Upon addition of the HCl significant off-gassing occurred, and at the completion of the off-gassing the reaction mixture was homogeneous. Isoamyl nitrite (2.1 mL, 15.7 mmol) was then added, and the solution darkened upon addition. The solution was stirred at room temperature for 16 hours, then reduced to dryness in vacuo to give a dark oil. This residue was purified by column chromatography (gradient elution of 25–50% ethyl acetate/hexanes) to give the final product as purple crystals (1.66 g, 29% from amide), mp 104–107° C.

$^1$H NMR (300 MHz,CDCl$_3$) δ 10.46 (bs, 1H), 7.50 (s, 2H), 3.17 (q, 2H, J=7.7 Hz), 2.75 (m, 2H), 1.49 (q, 2H, J=7.0 Hz), 1.46 (t, 3H, J=7.7 Hz), 0.85 (t, 3H, J=7.5 Hz). HRMS Calcd. for M+H (C$_{14}$H$_{16}$Cl$_3$N$_4$O): 361.0390. Found: 361.0386. Anal. Calcd. for C$_{14}$H$_{15}$Cl$_3$N$_4$O: C, 46.50; H, 4.18; N, 15.49, Found: C, 46.78; H, 4.10; N, 15.50.

Step E: The compound prepared in Step D (1.56 g, 4.31 mmol) was dissolved in anhydrous pyridine (20 mL) and the solution heated to reflux for 16 hours. The solvent was removed in vacuo and the residue purified by column chromatography (50% ethyl acetate/hexanes) to afford the product as a brown solid. This solid was washed with ethyl ether to leave the product as a tan solid (517 mg, 35%), mp 242–243.5° C. $^1$H NMR (300 MHz,CDCl$_3$) δ 8.60 (bs, 1H), 7.44 (s, 2H), 2.866 (q, 2H, J=7.6 Hz), 2.860 (q, 2H, J=7.5 Hz), 1.394 (t, 3H, J=7.7 Hz), 1.386 (t, 3H, J=7.7 Hz). HRMS Calcd. for M+H (C$_{14}$H$_{14}$Cl$_3$N$_4$): 343.0273. Found: 343.0284. Anal. Calcd. for C$_{14}$H$_{13}$Cl$_3$N$_4$: C, 48.93; H, 3.81; N, 16.30. Found: C, 48.87; H, 3.61; N, 16.14.

Step F: The compound prepared in Step E (80 mg, 0.23 mmol) was dissolved in anhydrous dimethylformamide (2.5 mL) and sodium bis(trimethylsilyl)amide (0.6 M in toluene, 0.97 mL, 0.58 mmol) was added. The solution was heated to 60° C. for one hour, then 1-bromobutane (0.10 mL, 0.92 mmol) was added. The reaction was held at 60° C. for one hour, cooled to room temperature, and diluted with water and diethyl ether. The layers were separated and the organic phase washed with water, dried over anhydrous magnesium sulfate, and reduced to dryness in vacuo. The residue was purified by column chromatography (25% ethyl acetate/hexanes) to give the final product as a crystalline solid (53 mg, 58%), mp 101–104° C. $^1$H NMR (300 MHz,CDCl$_3$) δ 7.43 (s, 2H), 4.02 (t, 2H, J=7.5 Hz), 2.87 (q, 2H, J=7.7 Hz), 2.79 (q, 2H, J=7.3 Hz), 1.84 (m, 2H), 1.39 (m, 8H), 1.01 (t, 3H, J=7.3 Hz). $^{13}$C NMR (75 MHz,CDCl$_3$) δ 157.18, 152.16, 136.73, 136.14, 135.15, 133.77, 128.58, 120.94, 45.27, 33.45, 21.31, 21.25, 20.04, 14.14, 13.74, 12.72. HRMS Calcd. for M+ (C$_{18}$H$_{21}$Cl$_3$N$_4$): 398.0829. Found: 398.0832. Anal. Calcd. for C$_{18}$H$_{21}$Cl$_3$N$_4$: C, 54.08; H, 5.30; N, 14.02. Found: C, 54.45; H, 5.22; N, 13.86.

EXAMPLE 153

Preparation of 4-(3,4-Difluorobenzyl)-5-ethyl-3-ethyl-1-(2,4,6-trichloro)phenylimidazo[4,5-c]pyrazole The compound prepared in Step E, Example 152 (80 mg, 0.23 mmol) was dissolved in anhydrous dimethylformamide (2.5 mL) and sodium bis(trimethylsilyl)amide (0.6 M in toluene, 0.97 mL, 0.58 mmol) was added. The solution was heated to 60° C. for one hour, then α-bromo-3,4-difluorotoluene (0.12 mL, 0.92 mmol) was added. The reaction was held at 60° C. for one hour, cooled to room temperature, and diluted with water and diethyl ether. The layers were separated and the organic phase washed with water, dried over anhydrous magnesium sulfate, and reduced to dryness in vacuo. The residue was purified by column chromatography (25% ethyl acetate/hexanes) to give the final product as a crystalline solid (74 mg, 68%), mp 100–103° C. $^1$H NMR (300 MHz,CDCl$_3$) δ 7.45 (s, 2H), 7.18 (m, 1H), 6.87 (m, 2H), 5.24 (s, 2H), 2.76 (q, 2H, J=7.7 Hz), 2.57 (q, 2H, J=7.6 Hz), 1.31 (t, 3H, J=7.6 Hz), 1.17 (t, 3H, J=7.5 Hz). HRMS Calcd. for M+H (C$_{21}$H$_{18}$Cl$_3$F$_2$N$_4$): 469.0550. Found: 469.0565. Anal. Calcd. for C$_{21}$H$_{17}$Cl$_3$F$_2$N$_4$ C, 53.69; H, 3.66; N, 11.93. Found: C, 53.85; H, 3.52; N, 11.49.

EXAMPLE 154

Preparation of 4-[1-(1-Ethyl)butane]-5-ethyl-3-ethyl-1-(2,4,6-trichloro)phenylimidazo[4,5-c]pyrazole The compound prepared in Step E, Example 152 (145 mg, 0.42 mmol) was dissolved in anhydrous dimethylformamide (4 mL) and sodium bis(trimethylsilyl)amide (0.6 M in toluene, 1.76 mL, 1.05 mmol) was added. The solution was heated to 60° C. for one hour, then 3-bromohexane (277 mg, 1.68 mmol) was added. The reaction was held at 60° C. for 24 hours, then held at 80° C. for an additional 24 hours. The reaction was then cooled to room temperature, and diluted with water and diethyl ether. The layers were separated and the organic phase washed with water, dried over anhydrous magnesium sulfate, and reduced to dryness in vacuo. The residue was purified by column chromatography (25% ethyl acetate/hexanes) to give the final product as a crystalline solid (22 mg, 12%), mp 96.5–98.0° C. $^1$H NMR (300 MHz,CDCl$_3$) δ 7.43 (s, 2H), 4.01 (m, 1H), 2.90 (q, 2H, J=7.3 Hz), 2.81 (q, 2H, J=7.7 Hz), 1.87 (m, 4H), 1.39 (t, 3H, J=7.5 Hz), 1.34 (t, 3H, J=7.5 Hz), 1.25 (m, 2H), 0.92 (t, 3H, J=7.3 Hz), 0.84 (t, 3H, J=7.5 Hz). HRMS Calcd. for M+ (C$_{20}$H$_{25}$Cl$_3$N$_4$): 426.1130. Found: 426.1145.

EXAMPLE 155

Preparation of 5-Ethyl-4-[1-(1-methyl)butane]-3-ethyl-1-(2,4,6-trichloro)phenylimidazo[4,5-c]pyrazole The compound prepared in Step E, Example 152 (145 mg, 0.42 mol) was dissolved in anhydrous dimethylformamide (4 mL) and sodium bis(trimethylsilyl)amide (0.6 M in toluene, 1.76 mL, 1.05 mmol) was added. The solution was heated to 60° C. for one hour, then 2-bromopentane (0.21 mL, 1.68 mmol) was added. The reaction was held at 60° C. for 24 hours, then held at 80° C. for an additional 24 hours. The reaction was then cooled to room temperature, and diluted with water and diethyl ether. The layers were separated and the organic phase washed with water, dried over anhydrous magnesium sulfate, and reduced to dryness in vacuo. The residue was purified by column chromatography (25% ethyl acetate/hexanes) to give the final product as a crystalline solid (20 mg, 11%), mp 87.5–89.5° C. $^1$H NMR (300 MHz,CDCl$_3$) δ 7.43 (s, 2H), 4.29 (m, 1H), 2.93 (q, 2H, J=7.3 Hz), 2.82 (q, 2H, J=7.7 Hz), 1.87 (m, 2H), 1.55 (d, 3H, J=6.6 Hz), 1.40 (t, 3H, J=7.5 Hz), 1.33 (t, 3H, J=7.5 Hz), 1.20 (m, 2H), 0.93 (t, 3H, J=7.3 Hz). HRMS Calcd. for M+H (C$_{19}$H$_{24}$Cl$_3$N$_4$): 413.1066. Found: 413.1056.

EXAMPLE 156

Preparation of 4-(n-Butyl)-5-ethyl-3-methoxymethyl-1-(2,4,6-trichloro)phenylimidazo[4,5-c]pyrazole Step A: A solution of methoxyacetonitrile (16.3 g, 0.23 mol) and acetonitrile (8.21 g, 0.20 mol) in tetrahydrofuran (50 mL) was added slowly at room temperature to potassium t-butoxide (1M in THF, 180 mL, 0.18 mol). A thick slurry resulted during the addition, and additional tetrahydrofuran (70 mL) was added. The reaction was heated to reflux for 24 hours, and was then slowly hydrolyzed with water (100 mL). This mixture was then extracted with dichloromethane, and the organic phase was dried over anhydrous magnesium sulfate, filtered and reduced in vacuo to leave a brown oil. This oil was then purified by vacuum distillation to give the β-aminoacrylonitrile as a light yellow solid (13.0 g, 116 mmol, 50%). To this solid was added 1N HCl (200 mL) and 2,4,6-trichlorophenylhydrazine (16.3 g, 77.0 mmol) and this mixture was heated at reflux for three hours. The reaction was cooled to room temperature and the supernatant aqueous phase was decanted and neutralized with 10% NaOH, producing an oil that solidifies upon stirring. The solid was isolated by filtration, then redissolved in 1N HCl and filtered to remove dark solids. The solution was neutralized to recover the product as a tan solid. The tarry residue from the reaction was dissolved in ethyl acetate and extracted with 1N HCl, and this extract was neutralized with 10% NaOH to leave a brown oil which solidifies upon standing to give the product (combined with earlier product, 5.71 g, 24%), mp 103.5–106° C. $^1$H NMR (300 MHz,CDCl$_3$) δ 7.49 (s, 2H), 5.72 (s, 1H), 4.42 (s, 2H), 3.58 (bs, 2H), 3.38 (s, 3H). HRMS Calcd. for M+H (C$_{11}$H$_{11}$Cl$_3$N$_3$O) : 305.9970. Found: 305.9974. Anal. Calcd. for C$_{11}$H$_{10}$Cl$_3$N$_3$O: C, 43.10; H, 3.30; N, 13.71. Found: C, 43.09; H, 3.23; N, 13.70.

Step B: The compound prepared in Step A (5.61 g, 18.3 mmol) was suspended in propionic anhydride (11.7 mL, 91.5 mmol) at room temperature and allowed to stir for 20 hours, resulting in a homogeneous solution. Ice was added and the reaction stirred for 5 hours, then diethyl ether was added and the phases were separated, the organic phase washed with saturated aqueous NaHCO$_3$, then saturated aqueous Na$_2$CO$_3$, then dried over anhydrous magnesium sulfate and reduced in vacuo to leave an oil. Ice was added to this oil and stirred for four hours, causing a solid to form. The solid was isolated by filtration to leave the product as an amorphous solid (5.42 g, 81%). $^1$H NMR (300 MHz,CDCl$_3$) 7.52(s, 2H), 6.72 (m, 2H), 4.51 (s, 2H), 3.40 (s, 3H), 2.31 (m, 2H), 1.15 (t, 3H, J=7.3 Hz). HRMS Calcd. for M+H (C$_{14}$H$_{15}$Cl$_3$N$_3$O$_2$): 362.0230. Found: 362.0223. Anal. Calcd. for C$_{14}$H$_{14}$Cl$_3$N$_3$O$_2$: C, 46.37; H, 3.89; N, 11.59. Found: C, 46.51; H, 3.82; N, 11.55.

Step C: The compound prepared in Step B (5.32 g, 14.7 mmol) was dissolved in anhydrous tetrahydrofuran (50 mL). To this suspension was added borane/THF complex (47.3 mL, 47.3 mmol), and the reaction was refluxed for 16 hours. The reaction was cooled to room temperature and excess borane was quenched with 10% NaOH (15 mL) until off-gassing ceased. The reaction was diluted with water and diethyl ether, the layers separated and the organic phase washed with saturated sodium chloride, dried over anhydrous magnesium sulfate, and reduced in vacuo to leave an orange oil. This oil was purified by column chromatography (25% ethyl acetate/hexanes) to give a light yellow oil (3.75 g, 73%) $^1$H NMR (300 MHz,CDCl$_3$) δ 7.48 (s, 2H), 5.59 (s, 1H), 4.44 (s, 2H), 3.40 (s, 3H), 3.10 (m, 3H), 1.58 (m, 2H), 0.92 (t, 3H, J=7.3 Hz) .Anal. Calcd. for C$_{14}$H$_{16}$Cl$_3$N$_3$O: C, 48.23; H, 4.64; N, 12.05. Found: C, 48.38; H, 4.50; N, 11.94. HRMS Calcd. for M+H (C$_{14}$H$_{17}$Cl$_3$N$_3$O) : 348.0437. Found: 348.0441.

Step D: The compound prepared in Step C was dissolved in ethanol (25 mL), and 15 drops of 10% HCl were added. Isoamyl nitrite (1.7 mL, 12.6 mmol) was then added, and the solution darkened upon addition. The solution was stirred at room temperature for 16 hours, and then reduced to dryness in vacuo to give a dark oil. This residue was purified by column chromatography (gradient elution of 25–50% ethyl acetate/hexanes) to give the final product as a dark blue oil (1.05 g, 26%). $^1$H NMR (300 MHz,CDCl$_3$) δ 10.25 (bs, 1H), 7.55 (s, 2H), 5.04 (s 2H), 3.56 (s, 3H), 2.76 (m, 2H), 1.49 (m, 2H), 0.86 (t, 3H, J=7.5 Hz). HRMS Calcd. for M+H (C$_{14}$H$_{16}$Cl$_3$N$_4$O$_2$): 377.0339. Found: 377.0318.

Step E: The compound prepared in Step D (1.05 g, 2.8 mmol) was dissolved in anhydrous pyridine (20 mL) and the solution heated to reflux for 16 hours. The solvent was removed in vacuo and the residue purified by column chromatography (50% ethyl acetate/hexanes) to afford the product as a brown solid. This solid was recrystallized from diethyl ether/ethyl acetate to give the product as a light tan solid (505 mg, 50%), mp 165.5–167.0° C. $^1$H NMR (300 MHz,CDCl$_3$) δ 8.89 (bs, 1H), 7.46 (s, 2H), 4.68 (s, 2H), 3.44 (s, 3H), 2.86 (q, 2H, J=7.7 Hz), 1.37 (t, 3H, J=7.7 Hz). HRMS Calcd. for M+H (C$_{14}$H$_{14}$Cl$_3$N$_4$O): 359.0233. Found: 359.0242. Anal. Calcd. for C$_{14}$H$_{15}$Cl$_3$N$_4$: C, 61.20; H, 5.50; N, 20.39; Cl, 12.90. Found: C, 61.18; H, 5.90; N, 20.34; Cl, 12.78.

Step F: The compound prepared in Step E (76 mg, 0.21 mmol) was dissolved in anhydrous dimethylformamide (3 mL) and sodium bis(trimethylsilyl)amide (0.6 M in toluene, 0.88 mL, 0.53 mmol) was added. The solution was heated to 60° C. for one hour, then 1-bromobutane (0.09 mL, 0.84 mmol) was added. The reaction was held at 60° C. for 1.5 hours, cooled to room temperature, and diluted with water and diethyl ether. The layers were separated and the organic phase washed with water, dried over anhydrous magnesium sulfate, and reduced to dryness in vacuo. The residue was purified by column chromatography (10% ethyl acetate/hexanes) to give the final product as an orange solid (46 mg, 53%), mp 65.5–67.5° C. $^1$H NMR (300 MHz,CDCl$_3$) δ 7.45 (s, 2H), 4.67 (s, 2H), 4.08 (t, 2H, J=7.5 Hz), 3.41 (ws, 3H), 2.80 (q, 2H, J=7.7 Hz), 1.84 (m, 2H), 1.43 (m, 2H), 1.36 (t, 3H, J=7.7 Hz), 1.00 (t, 3H, J=7.3 Hz). HRMS Calcd. for M+H (C$_{18}$H$_{22}$Cl$_3$N$_4$O): 415.0870. Found: 415.0859.

EXAMPLE 157

Preparation of 4-(3,4-Difluorobenzyl)-5-ethyl-3-methoxymethyl-1-(2,4,6-trichloro)phenylimidazo[4,5-c]pyrazole The compound prepared in Step E, Example 156 (76 mg, 0.21 mmol) was dissolved in anhydrous dimethylformamide (3 mL) and sodium bis(trimethylsilyl)amide (0.6 M in toluene, 0.88 mL, 0.53 mmol) was added. The solution was heated to 60° C. for one hour, then α-bromo-3,4-difluorotoluene (0.11 mL, 0.84 mmol) was added. The reaction was held at 60° C. for 1.5 hours, cooled to room temperature, and diluted with water and diethyl ether. The layers were separated and the organic phase washed with water, dried over anhydrous magnesium sulfate, and reduced to dryness in vacuo. The residue was purified by column chromatography (10% ethyl acetate/hexanes) to give the final product as an orange solid (50 mg, 49%), mp 91.5–94.5° C. $^1$H NMR (300 MHz,CDCl$_3$) δ 7.47 (s, 2H), 7.16 (m, 1H), 6.90 (m, 2H), 5.30 (s, 2H), 4.45 (s, 2H), 3.30 (s, 3H), 2.77 (q, 2H, J=7.7 Hz), 1.31 (t, 3H, J=7.7 Hz). $^{13}$C NMR (75 MHz,CDCl$_3$) δ 158.28, 152.56, 151.48, 148.87, 148.34, 148.17, 136.05, 135.76, 133.92, 133.23, 132.97, 128.68, 122.36, 122.30, 122.22, 121.83, 117.93, 117.70, 115.67, 115.43, 67.75, 57.75, 48.09, 21.45, 12.36. HRMS Calcd. for M+H (C$_{21}$H$_{18}$Cl$_3$F$_2$N$_4$O): 485.0505. Found: 485.0514.

EXAMPLE 158

Preparation of 4-[1-(1-Ethyl)butane]-5-ethyl-3-methoxymethyl-1-(2,4,6-trichloro)phenylimidazo[4,5-c]pyrazole The compound prepared in Step E, Example 156,(125 mg, 0.35 mmol) was dissolved in anhydrous dimethylformamide (4.0 mL) and sodium bis(trimethylsilyl)amide (0.6 M in toluene, 1.45 mL, 0.87 mmol) was added. The solution was heated to 60° C. for one hour, then 3-bromohexane (229 mg, 1.39 mmol) was added. The reaction was held at 60° C. for 20 hours, cooled to room temperature, and diluted with water and diethyl ether. The layers were separated and the organic phase washed with water, dried over anhydrous magnesium sulfate, and reduced to dryness in vacuo. The residue was purified by column chromatography (10% ethyl acetate/hexanes) to give the final product as a white solid (27 mg, 17%), mp 117–119° C. $^1$H NMR (300 MHz,CDCl$_3$) δ 7.46 (s, 2H), 4.67 (d, 2H, J=1.4 Hz), 4.04 (m, 1H), 3.34 (s, 3H), 2.83 (q, 2H, J=7.3 Hz), 1.92 (m, 4H), 1.35 (t, 3H, J=7.5 Hz), 0.91 (t, 3H, J=7.3 Hz), 0.82 (t, 3H, J=7.3 Hz). $^{13}$C NMR (75 MHz,CDCl$_3$) δ 158.65, 153.50, 136.09, 135.62, 133.32, 131.87, 128.64, 67.93, 58.61, 56.77, 37.10, 28.38, 22.11, 19.88, 13.87, 12.84, 11.10. HRMS Calcd. for M+H ($C_{20}H_{26}Cl_3N_4O$): 443.1161. Found: 443.1172.

EXAMPLE 159

Preparation of 5-Ethyl-4-[1-(1-methyl)butane]-3-methoxymethyl-1-(2,4,6-trichloro)phenylimidazo[4,5-c]pyrazole The compound prepared in Step E, Example 156 (125 mg, 0.35 mmol) was dissolved in anhydrous dimethylformamide (4 mL) and sodium bis(trimethylsilyl)amide (0.6 M in toluene, 0.97 mL, 0.58 mmol) was added. The solution was heated to 60° C. for one hour, then 2-bromopentane (0.18 mL, 1.39 mmol) was added. The reaction was held at 60° C. for 20 hours, cooled to room temperature, and diluted with water and diethyl ether. The layers were separated and the organic phase washed with water, dried over anhydrous magnesium sulfate, and reduced to dryness in vacuo. The residue was purified by column chromatography (10% ethyl acetate/hexanes) to give the final product as a crystalline solid (34 mg, 23%), mp 100.0–101.5° C. $^1$H NMR (300 MHz,CDCl$_3$) δ 7.46 (s, 2H), 4.69 (s, 2H), 4.32 (m, 1H), 3.36 (s, 3H), 2.84 (q, 2H, J=7.7 Hz), 2.05 (m, 1H), 1.85 (m, 1H), 1.58 (d, 3H, J=6.5 H), 1.34 (t, 3H, J=7.7 Hz), 1.18 (m, 2H), 0.92 (t, 3H, J=7.3 Hz). HRMS Calcd. for M+H ($C_{19}H_{24}Cl_3N_4O$): 429.1017. Found: 429.1016.

EXAMPLE 161

Preparation of 5-Ethyl-3-hydroxymethyl-4-[1-(1-methyl)butane]-1-(2,4,6-trichloro)phenylimidazo[4,5-c]pyrazole This compound was obtained as the second eluting compound from the reaction described in Example 163 (see below) as a solid (1.51 g, 65%), mp 144–146° C. $^1$H NMR (300 MHz,CDCl$_3$) δ 7.46 (s, 2H), 4.90 (d, 2H, J=5.8 Hz), 4.33 (m, 1H), 3.27 (bs, 1H), 2.84 (q, 2H, J=7.5 Hz), 1.97 (m, 1H), 1.88 (m, 1H), 1.56 (d, 3H, J=6.9 Hz), 1.34 (t, 3H, J=7.7 Hz), 1.25 (m, 2H), 0.91 (t, 3H, J=7.3 Hz). HRMS Calcd. for M+ ($C_{17}H_{19}Cl_3N_4O$): 415.0859. Found: 415.0860.

EXAMPLE 163

Preparation of 3-Bromomethyl-5-ethyl-4-[1-(1-methyl)butane]-1-(2,4,6-trichloro)phenylimidazo[4,5-c]pyrazole The compound prepared in Example 159 (2.39 g, 5.56 mmol) was dissolved in dichloromethane and cooled to −78° C. and BBr$_3$ (27.8 mL as 1.0 M in dichloromethane, 27.8 mmol) was added. The reaction was held at −78° C. for one hour, then warmed to room temperature for 16 hours. The reaction was quenched with water (100 mL) and diluted with dichloromethane. The layers were separated and the organic phase washed with saturated sodium chloride, dried over anhydrous magnesium sulfate, and reduced in vacuo. The residue was purified by column chromatography (gradient elution of 10–20% ethyl acetate/hexanes), the first eluting compound being the title product as an amorphous solid (660 mg, 25%). $^1$H NMR (300 MHz,CDCl$_3$) δ 7.46 (s, 2H), 4.75 (s, 2H), 4.35 (m, 1H), 2.84 (q, 2H, J=7.5 Hz), 2.0 (m, 2H), 1.63 (d, 3H, J=8.4 Hz), 1.35 (t, 3H, J=7.5 Hz), 1.25 (m, 2H), 0.96 (t, 3H, J=7.3 Hz). HRMS Calcd. for M+H ($C_{18}H_{21}Cl_3BrN_4$): 477.0016. Found: 477.0020.

EXAMPLE 164

Preparation of 4-Benzyl-5-isopropyl-3-methyl-1-(2,4,6-trichloro)phenyl-imidazo[4,5-c]pyrazole Part A: The product from Example 1, Part A (9.96 g, 36.01 mmol) was suspended in isobutyric anhydride (25 ml), refluxed for 18 hours and allowed to stir at room temperature for 18 hours. The reaction was treated with water (200 ml) and 10% sodium hydroxide (100 ml) and stirred 2 hours. The reaction was then extracted with diethyl ether (3×100 ml), and the combined organic extracts dried over anhydrous magnesium sulfate, and concentrated in-vacuo and dried to constant weight to afford an amorphous solid, 12.48 g (100%). $^1$H NMR (300 MHz, CDCl$_3$) δ 7.51 (s, 2H), 6.71 (bs, 1H), 6.47 (bs, 1H), 2.39 (m, 1H), 2.33 (s, 3H), 1.24 (d, 3H, J=7.0 Hz), 1.13 (d, 3H, J=7.0 Hz).

Part B: The product from Part A (12.48 g, 36.00 mmol) was reduced with borane/THF complex (100 ml) in the same manner as described for the preparation of Example 1, Part C to afford an oil, 10.91 g (92%). $^1$H NMR (300 MHz, CDCl$_3$) δ 7.53 (s, 2H), 5.39 (s, 1H), 3.49 (m, 1H), 2.94 (t, 2H, J=4.5 Hz), 2.39 (s, 3H).

Part C: The product from Step B (10.91 g, 32.80 mmol) was dissolved in ethanol (55 ml), cooled to 0° C., and treated with 1.0N HCl (0.5 ml) and isoamyl nitrite (4.40 ml, 32.80 mmol). The reaction was stirred for 3 hours while exposed to air, then concentrated to dryness in-vacuo, and purified by column chromatography on silica gel (800 g) eluting with hexanes/ethyl acetate (1/1) to afford a violet crystalline solid, 8.56 g (72%), mp 100–102° C. $^1$H NMR (300 MHz, CDCl$_3$) δ 10.53 (bs, 1H), 7.51 (s, 2H), 2.73 (s, 3H), 2.60 (t, 3H, J=6.3 Hz), 1.68 (m, 1H), 0.84 (d, 6H, J=7.2 Hz).

Part D: The product from Part C (8.56 g, 23.67 mmol) was dissolved in pyridine (143 ml) and the homogeneous solution refluxed 20 hours. The reaction was concentrated in-vacuo to remove pyridine and purified via column chromatography on silica gel (800 g) eluting initially with ethyl acetate/hexanes (1/1) and then hexanes/ethyl acetate (1/2) to afford desired imidazopyrazole, 1.49 g (18%), mp 139–139.5° C. $^1$H NMR (300 MHz, CDCl$_3$) δ 8.81 (bs, 1H), 7.44 (s, 2H), 3.13 (m, 1H), 2.46 (s, 3H), 1.39 (d, 6H, J=7.0 Hz).

Part E: The product from Part D (0.10 g, 0.29 mmol) was reacted with sodium hydride (30 mg, 0.75 mmol) and benzyl bromide (138 µl, 1.16 mmol) in dimethylformamide (2.0 ml) as described for the preparation of Example 1, Part F. Title compound: mp 103–105° C. $^1$H NMR (300 MHz, CDCl$_3$) δ 7.44 (s, 2H), 7.35 (m, 3H), 7.11 (d, 2H, J=6.6Hz), 5.29 (s, 2H), 3.07 (m, 1H), 2.15 (s, 3H), 1.32 (d, 6H, J=7.0 Hz). HRMS calcd. for M+ ($C_{21}H_{20}N_4Cl_3$): 432.0675. Found: 432.0660. Anal. Calcd. for $C_{21}H_{20}N_4Cl_3$: C, 58.14; H, 4.42; N, 12.92. Found: C, 58.30; H, 4.29; N, 12.70.

EXAMPLE 165

Preparation of 4-(n-Butyl)-5-isopropyl-3-methyl-1-(2,4,6-trichloro)phenyl imidazo[4,5-c]pyrazole The product from Example 164, Step D (100 mg, 0.29 mmol) was reacted with sodium hydride (30 mg, 0.75 mmol) and n-butyl bromide (125 µl, 1.16 mmol) in dimethylformamide (2.0 ml) as described for the preparation of Example 1, Part F. Title compound: mp 85.0–86.0° C. $^1$H NMR (300 MHz, CDCl$_3$) δ 7.43 (s, 2H), 4.03 (t, 2H, J=7.3 Hz), 3.05 (m, 1H), 2.51 (s, 3H), 1.84 (m, 2H), 1.45 (m, 2H), 1.36 (d, 6H, J=7.6 Hz), 1.01 (t, 3H, J=7.3 Hz). HRMS calcd. for M+ ($C_{18}H_{21}N_4Cl_3$): 398.0832. Found: 398.0819.

EXAMPLE 166

Preparation of 5-Isopropyl-3-methyl-4-[1-(3-methyl) butane]-1-(2,4,6-trichloro)phenyl imidazo[4,5-c] pyrazole The product from Example 164, Step D (100 mg, 0.29 mmol) was reacted with sodium hydride (30 mg, 0.75 mmol) and 1-bromo-2-ethylbutane (160 μl, 1.16 mmol) in dimethylformamide (2.0 ml) as described for the preparation of Example 1, Part F. Title compound: mp 88.0–91.0° C. $^1$H NMR (300 MHz, CDCl$_3$) δ 7.43 (s, 2H), 3.92 (d, 2H, J=6.6 Hz), 3.03 (m, 1H), 2.50 (s, 3H), 2.78 (m, 1H), 1.35 (d, 6H, J=7.0 Hz), 1.40–1.25 (m, 4H), 0.94 (t, 6H, J=7.3 Hz). HRMS calcd. for M+ ($C_{20}H_{25}N_4Cl_3$): 426.1145. Found: 412.1143.

EXAMPLE 167

Preparation of 5-Isopropyl-3-methyl-4-[1-(3-methyl) butane]-1-(2,4,6-trichloro)phenyl imidazo[4,5-c] pyrazole The product from Example 164, Step D (100 mg, 0.29 mmol) was reacted with sodium hydride (30 mg, 0.75 mmol) and 1-bromo-3-methylbutane (140 μl, 1.16 mmol) in dimethylformamide (2.0 ml) as described for the preparation of Example 1, Part F. Title compound: mp 87.0–89.0° C. $^1$H NMR (300 MHz, CDCl$_3$) δ 7.43 (s, 2H), 4.04 (m, 2H), 3.02 (m, 1H), 2.52 (s, 3H), 1.76 (m, 3H), 1.36 (d, 6H, J=7.0 Hz), 1.23 (m, 2H), 1.03 (d, 6H, J=6.2 Hz). HRMS calcd. for M+ ($C_{19}H_{23}N_4Cl_3$): 412.0988. Found: 412.0988. Anal. Calcd. for $C_{19}H_{23}N_4Cl_3$: C, 55.15; H, 5.60; N, 13.54. Found: C, 55.44; H, 5.50; N, 13.17.

EXAMPLE 238

Preparation of 5-Ethyl-3-formyl-4-[1-(1-methyl) butane]-1-(2,4,6-trichloro)phenylimidazo[4,5-c] pyrazole Dess-Martin periodinane (1.84 g, 4.33 mmol) was dissolved in anhydrous acetonitrile (3 mL), and to this was added the compound prepared in Example 161 (1.50 g, 3.61 mmol) suspended in anhydrous acetonitrile (60 mL). The reaction was stirred at room temperature for 30 minutes, and was then diluted with diethyl ether. The reaction was quenched with 0.5 N NaOH and the phases were separated, the organic phase was washed with saturated sodium chloride, dried over anhydrous magnesium sulfate, and reduced in vacuo. The residue was purified by column chromatography (25% ethyl acetate/hexanes) to give the product as an amophous white solid (1.43 g, 96%). $^1$H NMR (300 MHz,CDCl$_3$) δ 9.97 (s, 1H), 7.52 (s, 2H), 4.43 (m, 1H), 2.88 (q, 2H, J=7.5 Hz), 2.16 (m, 1H), 1.95 (m, 1H), 1.66 (d, 3H, J=7.0 Hz), 1.36 (t, 3H, J=7.5 Hz(), 1.27 (m, 1H), 1.11 (m, 1H), 0.89 (t, 3H, J=7.3 Hz). HRMS Calcd. for M+H ($C_{18}H_{20}Cl_3N_4O$): 413.0703. Found: 413.0704.

EXAMPLE 243

Preparation of 5-Ethyl-3-(1-hydroxyethyl)-4-[1-(1-methyl)butane]-1-(2,4,6-trichloro)phenylimidazo[4,5-c]pyrazole The compound prepared in Example 238 (1.38 g, 3.33 mmol) was dissolved in anhydrous tetrahydrofuran (50 mL) and cooled to −78° C. To this solution was added methylmagnesium bromide (2.11 mL, 3.0 M in diethyl ether, 6.33 mol) and the reaction was held at −78° C. for one hour, then the temperature was gradually increased to room temperature. After three hours at room temperature, the reaction was quenched with 15% aqueous ammonium chloride and diethyl ether was added. The organic phase was dried over anhydrous magnesium sulfate and reduced in vacuo. The residue was purified by chromatography (20% ethyl acetate/ hexanes) to give the desired mixture of diastereomers as a white solid (950 mg, 66%), mp 182.0–184.0° C. $^1$H NMR (300 MHz,CDCl$_3$) δ 7.45 (s, 2H), 5.15 (m, 1H), 4.40 (m, 1H), 2.83 (q, 2H, J=7.5 Hz), 2.28 (d, 0.5H, J=7.7 Hz), 2.23 (d, 0.5H, J=7.7 Hz), 2.0 (m, 2H), 1.72 (d, 1.5H, J=6.6 Hz), 1.72 (d, 1.5H, J=6.6 Hz), 1.56 (m, 3H), 1.34 (t, 3H, J=7.7 Hz), 0.93 (t, 1.5H, J=7.3 Hz), 0.921 (t, 1.5H, J=7.3 Hz) . HRMS Calcd. for M+H ($C_{19}H_{24}Cl_3N_4O$): 429.1016. Found: 429.1010. Anal. Calcd. for ($C_{19}H_{23}Cl_3N_4O$): C, 53.10; H, 5.39; N, 13.04. Found: C, 53.11; H, 5.41; N, 12.64.

EXAMPLE 251

Preparation of 3-Acetyl-5-ethyl-4-[1-(1-methyl) butane]-1-(2,4,6-trichloro)phenylimidazo[4,5-c] pyrazole Dess-Martin periodinane (1.12 g, 2.65 mmol) was suspended in anhydrous dichloromethane (5 mL) and to this solution was added the compound prepared in Example 243 (950 mg, 2.21 mmol) in anhydrous dichloromethane (100 mL). The reaction was held at room temperature for two hours, and was then quenched with 0.5 N NaOH (200 mL). Diethyl ether was added and the organic phase was dried over anhydrous magnesium sulfate and reduced in vacuo. The residue was purified by chromatography (gradient elutions with 10–20% ethyl acetate/hexanes) to give the final product as a white solid (768 mg, 81%), mp 50.0–52.0° C. $^1$H NMR (400 MHz,DMSO-d$_6$, 120° C.) δ 7.88 (s, 2H), 4.66 (m, 1H), 2.85 (q, 1H, J=7.5 Hz), 2.84 (q, 1H, J=7.4 Hz), 2.05 (m, 1H), 1.90 (m, 1H), 1.57 (d, 3H, J=6.8 Hz), 1.28 (m, 4H, includes 1.26 (t, 3H, J=7.5 Hz), 1.09 (m, 1H), 0.83 (t, 3H, J=7.3 Hz). HRMS Calcd. for M+H ($C_{19}H_{22}Cl_3N_4O$): 427.0859. Found: 427.0853. Anal. Calcd. for $C_{19}H_{21}Cl_3N_4O$: C, 53.35; H, 4.961 N, 13.10. Found: C, 53.55; H, 4.91; N, 13.11.

The Examples in Table 2 may be prepared as exemplified above for the preparation of Examples 38, 40, 105–108, 113–118, 152–159, 161, 163–167, 238, 243, and 251.

TABLE 2

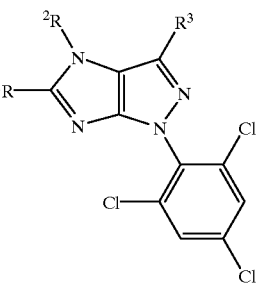

| Ex. | $R^1$ | $R^2$ | $R^3$ | mp ° C. |
|---|---|---|---|---|
| 37 | Et | CH$_2$Ph | Me | 129–131 |
| 38 | Et | CH$_2$CH(Et)$_2$ | Me | 135–136 |

TABLE 2-continued

| Ex. | R¹ | R² | R³ | mp °C |
|---|---|---|---|---|
| 39 | Et | CH₂CH₂CH(Me)₂ | Me | 109–110 |
| 40 | Et | CH₂cPr | Me | 144–146 |
| 41 | Et | n-butyl | Me | 115–117 |
| 42 | Et | n-propyl | Me | 110–113 |
| 43 | Et | CH(Et)₂ | Me | 110–111 |
| 44 | Et | CH₂CH₂CH₂CN | Me | Oil, MS |
| 45 | Et | CH₂CH₂CN | Me | 192–194 |
| 46 | Et | 4-methoxybenzyl | Me | 134–136 |
| 47 | Et | 3-methoxybenzyl | Me | Oil, MS |
| 48 | Et | 2-methylbenzyl | Me | 135–137 |
| 49 | Et | 3-methylbenzyl | Me | 155–156 |
| 50 | Et | 4-methylbenzyl | Me | 133–134 |
| 51 | Et | 2,4-dimethylbenzyl | Me | Oil, MS |
| 52 | Et | 2,5-dimethylbenzyl | Me | 130–133 |
| 53 | Et | 3,4-dimethylbenzyl | Me | 125–127 |
| 54 | Et | 3,5-dimethylbenzyl | Me | 157–157 |
| 55 | Et | 4-tertbutylbenzyl | Me | 104–105 |
| 56 | Et | 2-phenylbenzyl | Me | 126–127 |
| 57 | Et | 4-phenylbenzyl | Me | 140–141 |
| 58 | Et | 2-bromobenzyl | Me | 151–153 |
| 59 | Et | 3-bromobenzyl | Me | 147–148 |
| 60 | Et | 4-bromobenzyl | Me | 192–194 |
| 61 | Et | 2-chlorobenzyl | Me | 158–159 |
| 62 | Et | 3-chlorobenzyl | Me | 140–141 |
| 63 | Et | 4-chlorobenzyl | Me | 193–195 |
| 64 | Et | 2,4-dichlorobenzyl | Me | 194–195 |
| 65 | Et | 2,6-dichlorobenzyl | Me | 130–132 |
| 66 | Et | 3,4-dichlorobenzyl | Me | 187–188 |
| 67 | Et | 2-chloro-6-fluorobenzyl | Me | 146–147 |
| 68 | Et | 2-fluorobenzyl | Me | 127–129 |
| 69 | Et | 3-fluorobenzyl | Me | 136–137 |
| 70 | Et | 4-fluorobenzyl | Me | 130–132 |
| 71 | Et | 2,4-difluorobenzyl | Me | 151–152 |
| 72 | Et | 2,5-difluorobenzyl | Me | 162–163 |
| 73 | Et | 3,4-difluorobenzyl | Me | 154–155 |
| 74 | Et | 3,5-difluorobenzyl | Me | 139–140 |
| 75 | Et | 2-trifluoromethylbenzyl | Me | 177–178 |
| 76 | Et | 3-trifluoromethylbenzyl | Me | 176–178 |
| 77 | Et | 4-trifluoromethylbenzyl | Me | 167–168 |
| 78 | Et | 2,4-bis(trifluoromethyl)benzyl | Me | 150–151 |
| 79 | Et | 3,5-bis(trifluoromethyl)benzyl | Me | 144–145 |
| 80 | Et | 3,5-dimethoxybenzyl | Me | 139–140 |
| 81 | Et | 4-methoxy-3-methylbenzyl | Me | 149–150 |
| 82 | Et | 4-benzyloxybenzyl | Me | 115–117 |
| 83 | Et | 2-cyanobenzyl | Me | 220–221 |
| 84 | Et | 3-cyanobenzyl | Me | 149–152 |
| 85 | Et | 4-cyanobenzyl | Me | 205–206 |
| 86 | Et | 3-trifluoromethoxybenzyl | Me | 93–96 |
| 87 | Et | 4-trifluoromethoxybenzyl | Me | 79–81 |
| 88 | Et | 2-nitrobenzyl | Me | >250 |
| 89 | Et | 3-nitrobenzyl | Me | >250 |
| 90 | Et | 4-nitrobenzyl | Me | >250 |
| 91 | Et | 2-methyl-3-nitrobenzyl | Me | >250 |
| 92 | Et | 4-acetamidobenzyl | Me | Oil, MS |
| 93 | Et | CH₂CH₂CH(OiPr)4-methylphenyl | Me | Oil, MS |
| 94 | Et | CH₂CH₂CH(OMe)4-chlorophenyl | Me | Oil, MS |
| 95 | Et | CH₂CH₂CH₂CF₃ | Me | 138–140 |
| 96 | Et | geranyl | Me | 151–152 |
| 97 | Et | CH₂CH=CHPh | Me | Oil, MS |
| 98 | Et | CH₂(cyclohexyl) | Me | 149–150 |
| 99 | Et | CH₂CH(Me)₂ | Me | 131–132 |
| 100 | Et | CH₂CH₂CH₂CCH | Me | 145–146 |
| 101 | Et | nPentyl | Me | 142–143 |
| 102 | Et | CH₂CH₂OCH₂CH₃ | Me | 195–196 |
| 103 | Et | CH₂(2-tetrahydropyran) | Me | Oil, MS |
| 104 | Et | CH₂CH(CH₃)CH₂CH₃ | Me | 118–120 |
| 105 | Et | CH(CH₂CH₂CH₃)₂ | Me | 113–114 |
| 106 | Et | CH(CH₂CH₃)CH₂CH₂CH₂CH₃ | Me | 121–122 |
| 107 | Et | CH(CH₃)CH₂CH₃ | Me | 113–114 |
| 108 | Et | CH(CH₃)CH₂CH₂CH₃ | Me | 93–95 |
| 109 | Et | CH(CH₃)CH₂CH₂CH₂CH₃ | Me | Oil, MS |
| 110 | Et | CH(CH₃)CH₂CH(CH₃)₂ | Me | 119–120 |
| 111 | Et | CH(CH₃)CH₂CH₂CH₂CH₃ | Me | Oil, MS |
| 112 | Et | 4-methylcyclohexyl | Me | Oil, MS |
| 113 | Et | 4-methanesulfonylbenzyl | Me | 194–196 |
| 114 | Et | COPh | Me | 169–170 |
| 115 | Et | SO₂Ph | Me | 189–190 |
| 116 | Et | CH(phenyl)₂ | Me | 170–172 |
| 117 | Et | CH(CH₃)phenyl | Me | 166–168 |
| 118 | Et | cyclopentyl | Me | 125–128 |
| 119 | Et | cyclohexyl | Me | |
| 120 | Et | CH₂(2-tetrahydrofuran) | Me | |
| 121 | Et | CH₂CH₂COPh | Me | |
| 122 | Et | CH₂CH₂CO(4-fluorophenyl) | Me | |
| 123 | Et | CH₂CH₂COCH₂CH₃ | Me | |
| 124 | Et | CH₂CH₂CH₂COCH₃ | Me | |
| 125 | Et | CH₂CH₂NHCOPh | Me | |
| 126 | Et | 2,4,6-trimethylbenzyl | Me | |
| 127 | Et | 2-picolyl | Me | |
| 128 | Et | 3-picolyl | Me | |
| 129 | Et | 4-picolyl | Me | |
| 130 | Et | 2-methylquinoline | Me | |
| 131 | Et | n-butyl | H | 80–82 |
| 132 | Et | benzyl | H | 86–89 |
| 133 | Et | 3,4-difluorobenzyl | H | 145–147 |
| 134 | Et | CH₂CH(CH₂CH₃)₂ | H | Oil, MS |
| 135 | Et | CH₂CH₂CH(CH₃)₂ | H | Oil, MS |
| 136 | Et | CH₂-2-tetrahydropyranyl | H | Oil, MS |
| 137 | Et | CH(CH₂CH₃)CH₂CH₂CH₃ | H | Oil, MS |
| 138 | Et | CH(CH₃)CH₂CH(CH₃)₂ | H | 90–92 |
| 139 | Et | CH(CH₃)CH₂CH₂CH₃ | H | Oil, MS |
| 140 | n-Pr | n-butyl | H | Oil, MS |
| 141 | n-Pr | CH(CH₂CH₃)CH₂CH₂CH₃ | H | Oil, MS |
| 142 | n-Pr | CH(CH₃)CH₂CH(CH₃)₂ | H | Oil, MS |
| 143 | n-Pr | CH(CH₃)CH₂CH₂CH₃ | H | Oil, MS |
| 144 | n-Pr | n-butyl | Me | 94–95 |
| 145 | n-Pr | CH(CH₂CH₃)CH₂CH₂CH₃ | Me | 91–93 |
| 146 | n-Pr | CH(CH₃)CH₂CH(CH₃)₂ | Me | 113–115 |
| 147 | n-Pr | CH(CH₃)CH₂CH₂CH₃ | Me | 98–100 |
| 148 | c-Pr | n-butyl | Me | 91–93 |
| 149 | c-Pr | CH(CH₂CH₃)CH₂CH₂CH₃ | Me | 120–122 |
| 150 | c-Pr | CH(CH₃)CH₂CH(CH₃)₂ | Me | 152–155 |
| 151 | c-Pr | CH(CH₃)CH₂CH₂CH₃ | Me | 102–105 |
| 152 | Et | n-butyl | Et | 101–104 |
| 153 | Et | 3,4-difluorobenzyl | Et | Oil, MS |
| 154 | Et | CH(CH₂CH₃)CH₂CH₂CH₃ | Et | 96–98 |
| 155 | Et | CH(CH₃)CH₂CH₂CH₃ | Et | 88–90 |
| 156 | Et | n-butyl | CH₂OCH₃ | 66–68 |
| 157 | Et | 3,4-difluorobenzyl | CH₂OCH₃ | Oil, MS |
| 158 | Et | CH(CH₂CH₃)CH₂CH₂CH₃ | CH₂OCH₃ | 117–119 |
| 159 | Et | CH(CH₃)CH₂CH₂CH₃ | CH₂OCH₃ | 100–102 |
| 160 | Et | n-butyl | CH₂OH | 163–165 |

TABLE 2-continued

[Structure: imidazo[4,5-c]pyrazole with $R^1$, $R^2$, $R^3$ substituents and N1-(2,4,6-trichlorophenyl) group]

| Ex. | $R^1$ | $R^2$ | $R^3$ | mp °C. |
|---|---|---|---|---|
| 161 | Et | CH(CH$_3$)CH$_2$CH$_2$CH$_3$ | CH$_2$OH | 144–146 |
| 162 | Et | CH(CH$_3$)CH$_2$CH$_2$CH$_3$ | CH$_2$F | Oil, MS |
| 163 | Et | CH(CH$_3$)CH$_2$CH$_2$CH$_3$ | CH$_2$Br | Oil, MS |
| 164 | i-Pr | benzyl | Me | 103–105 |
| 165 | i-Pr | n-butyl | Me | 85–86 |
| 166 | i-Pr | CH$_2$CH(CH$_2$CH$_3$)$_2$ | Me | 88–91 |
| 167 | i-Pr | CH$_2$CH$_2$CH(CH$_3$)$_2$ | Me | 87–89 |
| 168 | i-Pr | n-butyl | H | |
| 169 | i-Pr | benzyl | H | |
| 170 | i-Pr | CH$_2$CH(CH$_2$CH$_3$)$_2$ | H | |
| 171 | i-Pr | CH$_2$CH$_2$CH(CH$_3$)$_2$ | H | |
| 172 | n-Bu | n-butyl | Me | |
| 173 | n-Bu | benzyl | Me | |
| 174 | n-Bu | CH$_2$CH(CH$_2$CH$_3$)$_2$ | Me | |
| 175 | n-Bu | CH$_2$CH$_2$CH(CH$_3$)$_2$ | Me | |
| 176 | Ph | n-butyl | Me | |
| 177 | Ph | CH(CH$_2$CH$_3$)CH$_2$CH$_2$CH$_3$ | Me | |
| 178 | Ph | CH(CH$_3$)CH$_2$CH(CH$_3$)$_2$ | Me | |
| 179 | Ph | CH(CH$_3$)CH$_2$CH$_2$CH$_3$ | Me | |
| 180 | Ph | CH(CH$_3$)CH$_2$CH(CH$_3$)$_2$ | Me | |
| 181 | Ph | CH(CH$_3$)CH$_2$CH$_2$CH$_3$ | Me | |
| 182 | CF$_3$ | n-butyl | Me | |
| 183 | CF$_3$ | CH(CH$_2$CH$_3$)CH$_2$CH$_2$CH$_3$ | Me | |
| 184 | CF$_3$ | CH(CH$_3$)CH$_2$CH(CH$_3$)$_2$ | Me | |
| 185 | CF$_3$ | CH(CH$_3$)CH$_2$CH$_2$CH$_3$ | Me | |
| 186 | CF$_3$ | CH(CH$_3$)CH$_2$CH(CH$_3$)$_2$ | Et | |
| 187 | CF$_3$ | CH(CH$_3$)CH$_2$CH$_2$CH$_3$ | Et | |
| 188 | Et | n-butyl | CF$_3$ | |
| 189 | Et | CH(CH$_2$CH$_3$)CH$_2$CH$_2$CH$_3$ | CF$_3$ | |
| 190 | Et | CH(CH$_3$)CH$_2$CH(CH$_3$)$_2$ | CF$_3$ | |
| 191 | Et | CH(CH$_3$)CH$_2$CH$_2$CH$_3$ | CF$_3$ | |
| 192 | Et | n-butyl | CHF$_2$ | |
| 193 | Et | benzyl | CHF$_2$ | |
| 194 | Et | CH(CH$_3$)CH$_2$CH$_2$CH$_3$ | CHF$_2$ | |
| 195 | Et | CH(CH$_3$)CH$_2$CH$_2$CH$_3$ | CH$_2$CF$_3$ | |
| 196 | Et | CH$_2$CH$_2$SCH$_2$CH$_3$ | Me | |
| 197 | Et | CH$_2$CH$_2$OPh | Me | |
| 198 | Et | CH$_2$CH(CH$_3$)CN | Me | |
| 199 | Et | (CH$_2$)$_4$CN | Me | |
| 200 | Et | 2-methoxybenzyl | Me | |
| 201 | Et | 2-methoxy-5-nitrobenzyl | Me | |
| 202 | Et | 2-hydroxy-5-nitrobenzyl | Me | |
| 203 | Et | CH$_2$CH$_2$Ph | Me | |
| 204 | Et | (CH$_2$)$_3$Ph | Me | |
| 205 | Et | CH$_2$CH$_2$N(i-Pr)$_2$ | Me | |
| 206 | Et | CH$_2$CH$_2$-morpholino | Me | |
| 207 | Et | 5-methyl-2-nitrobenzyl | Me | |
| 208 | Et | 2-pentanone | Me | |
| 209 | Et | 2,4,6-trifluorobenzyl | Me | |
| 210 | Et | CH(COphenyl)CH$_3$ | Me | |
| 211 | Et | CH(COphenyl)CH(CH$_3$)$_2$ | Me | |
| 212 | Et | CH(COphenyl)phenyl | Me | |
| 213 | Et | CH(COphenyl)benzyl | Me | |
| 214 | Et | CH(CO$_2$CH$_3$)phenyl | Me | |
| 215 | Et | CH(CO$_2$CH$_3$)CH$_2$CH$_2$CH$_3$ | Me | |
| 216 | Et | CH(COCH$_3$)CH$_3$ | Me | |
| 217 | Et | CH$_2$CH(OH)CH$_2$Ophenyl | Me | |
| 218 | Et | CH$_2$CH(OH)phenyl | Me | |
| 219 | Et | CH$_2$CH(OH)benzyl | Me | |
| 220 | Et | CH$_2$CH(OH)CH$_2$CH$_2$CH$_3$ | Me | |
| 221 | Et | CH$_2$COCH$_2$CH$_2$CH$_3$ | Me | |
| 222 | Et | CH$_2$CObenzyl | Me | |
| 223 | Et | CH$_2$CH(OMe)benzyl | Me | |
| 224 | Et | CO(4-chlorophenyl) | Me | |
| 225 | Et | CO(2-methoxyphenyl) | Me | |
| 226 | Et | COCH(CH$_2$CH$_3$)phenyl | Me | |
| 227 | Et | CO$_2$CH$_2$CH$_3$ | Me | |
| 228 | Et | CO$_2$phenyl | Me | |
| 229 | Et | CON(CH$_3$)phenyl | Me | |
| 230 | Et | COmorpholino | Me | |
| 231 | Et | SO$_2$(2-thiophene) | Me | |
| 232 | Et | SO$_2$benzyl | Me | |
| 233 | Et | SO$_2$CH$_2$CH$_2$CH$_3$ | Me | |
| 234 | Et | CON(CH$_3$)phenyl | H | |
| 235 | Et | COmorpholino | CF$_3$ | |
| 236 | Et | SO$_2$(2-thiophene) | CF$_3$ | |
| 237 | Et | n-butyl | CHO | |
| 238 | Et | CH(CH$_3$)CH$_2$CH$_2$CH$_3$ | CHO | Oil, MS |
| 239 | Et | benzyl | CHO | |
| 240 | Et | CH$_2$cPr | CH(CH$_3$)OH | |
| 241 | Et | n-butyl | CH(CH$_3$)OH | |
| 242 | Et | benzyl | CH(CH$_3$)OH | |
| 243 | Et | CH(CH$_3$)CH$_2$CH$_2$CH$_3$ | CH(CH$_3$)OH | 182–184 |
| 244 | Me | benzyl | CH(Ph)OH | |
| 245 | Et | CH(CH$_3$)CH$_2$CH$_2$CH$_3$ | CH(Ph)OH | |
| 246 | Et | n-butyl | CO$_2$H | |
| 247 | Et | CH(CH$_3$)CH$_2$CH$_2$CH$_3$ | CO$_2$H | |
| 248 | Et | CH(CH$_3$)CH$_2$CH$_2$CH$_3$ | CO$_2$Et | |
| 249 | Et | n-butyl | CO$_2$Et | |
| 250 | Et | benzyl | COMe | |
| 251 | Et | CH(CH$_3$)CH$_2$CH$_2$CH$_3$ | COMe | 50–52 |
| 252 | Et | n-butyl | COMe | |
| 253 | Et | 3,4-difluorobenzyl | COMe | |
| 254 | Et | 4-fluorobenzyl | COMe | |
| 255 | Et | cyclopentyl | COMe | |
| 256 | Et | CH(CH$_3$)CH$_2$CH$_2$CH$_3$ | CH$_2$NH$_2$ | |
| 257 | Et | benzyl | CH$_2$NH$_2$ | |
| 258 | Et | CH$_2$cPr | CH$_2$NHMe | |
| 259 | Et | n-butyl | CH$_2$NHMe | |
| 260 | Et | benzyl | CH$_2$NMe$_2$ | |
| 261 | Et | CH(CH$_3$)CH$_2$CH$_2$CH$_3$ | CH$_2$NMe$_2$ | |

EXAMPLE 263

Preparation of 4-Benzyl-5-ethyl-3-methyl-1-(2,4,6-trimethyl)phenyl-imidazo[4,5-c]pyrazole Step A: The product from Example 11, Part A (10 g, 46.44 mmol) was suspended in propionic anhydride (30 ml) and allowed to stir at room temperature for 2 hours. The reaction was poured onto an ice slurry (500 ml) and stirred overnight. The resultant precipitate was filtered and dried to constant weight to afford 11.92 g (95%) of desired amido pyrazole, mp 171.5–173° C. $^1$H NMR (300 MHz, CDCl$_3$) δ 6.98 (s, 2H), 6.74 (bs, 1H), 6.54 (s, 1H), 2.34 (s, 3H), 2.31 (s, 3H), 2.24 (q, 2H, J=7.3 Hz), 1.96 (s, 3H), 1.13 (t, 3H, J=7.3 Hz).

SteD B: The product from Step A (11.5 g, 42.37 mmol) was reduced with lithium aluminum hydride (84.75 ml, 84.74 mmol, 1.0 M/THF) as described for the preparation of Example 11, Step C. The product was obtained as a clear viscous oil, 10.81 g (99%). $^1$H NMR (300 MHz, CDl$_3$) δ 6.93 (s, 2H), 5.31 (s, 1H), 3.02 (m, 3H), 2.31 (s, 3H), 2.24 (s, 3H), 1.99 (s, 6H), 1.53 (m, 2H), 0.88 (t, 3H, J=7.3 Hz).

Step C: The product from Step B (10.81 g, 41.99 mmol) was treated with isoamyl nitrite (5.62 ml, 41.99 mmol) as described for the preparation of Example 11, Step D to afford a purple crystalline solid, 9.59 g (80%). $^1$H NMR (300 MHz, CDCl$_3$) δ 10.07 (bs, 1H), 6.94 (s, 2H), 2.70 (s, 3H), 2.62 (q, 2H, J=6.8 Hz), 2.36 (s, 3H), 2.09 (s, 6H), 1.36 (m, 2H), 0.77 (t, 3H, J=7.3 Hz).

Step D: The product from Step C (9.59 g) was refluxed in pyridine (60 ml) for 16 hours, as described for the preparation of Example 11, Step E. Chromatography on silica gel (700 g) eluting with hexanes/ethyl acetate (1/1) yielded recovery of 2.38 g of starting material, while elution with ethyl acetate alone afforded the desired product, 3.41 g (50% based on recovered starting material). $^1$H NMR (300 MHz, CDCl$_3$) δ 9.67 (bs, 1H), 6.86 (s, 2H), 2.71 (q, 2H, J=7.8 Hz), 2.38 (s, 3H), 2.27 (s, 3H), 1.99 (s, 6H), 1.28 (t, 3H, J=7.8 Hz).

Step E: The product from Step D (0.25 g, 0.93 mmol) was treated with sodium hydride (93 mg, 2.32 mmol) and benzyl bromide (443 μl, 3.7 mmol) in anhydrous dimethylformamide (15 ml) as described for the preparation of Example 11, Step F. Title compound: 200.0 mg (60%), mp 96.5–98° C., $^1$H NMR (300 MHz, CDCl$_3$) δ 7.35 (m, 3H), 7.14 (d, 2H, J=6.6 Hz), 6.90 (s, 2H), 5.26 (s, 2H), 2.77 (q, 2H, J=7.7 Hz), 2.29 (s, 3H), 2.16 (s, 3H), 2.02 (s, 6H), 1.29 (t, 3H, J=7.7 Hz).

EXAMPLE 325

Preparation of 4-(n-Butyl)-5-ethyl-3-methyl-1-(2-chloro-4-bromo)phenylimidazo[4,5-c]pyrazole Step A: β-Aminocrotononitrile (8.62 g, 0.10 mol) was dissolved in 1.0N HCl (275 ml) and treated with 2-chloro-4-bromophenylhydrazine (0.1 mol). The reaction was refluxed 4 h, cooled, and decanted into a 2 liter beaker. The solution was diluted with water (250 ml) and neutralized with 10% NaOH (125 ml). The resultant precipitate was filtered and dried to constant weight to afford 22.71 g (79%) of the desired aminopyrazole as a white crystalline solid, mp 125.0–126.0° C. $^1$H NMR (300 MHz, CDCl$_3$) δ 7.69 (d, 1H, J=2.0 Hz), 7.51 (dd, 1H, J=2.0, 7.0 Hz), 7.34 (d, 1H, J=7.0 Hz), 5.46 (s, 1H), 3.58 (bs, 2H), 2.23 (s, 3H).

Step B: The compound prepared in Step A (4.0 g, 14.0 mmol) was suspended in propionic anhydride (9.0 mL, 69.8 mmol) at room temperature and was allowed to stir for 16 hours. Ice was then added and the reaction stirred for 5 hours. Diethyl ether was added and the phases were separated. The organic phase was washed with saturated sodium chloride, dried over magnesium sulfate and reduced in vacuo to leave a thick oil. This residue was purified by column chromatography (50% ethyl acetate/hexanes) to give the final product as a solid (4.2 g, 88%), mp 107–110° C. $^1$H NMR (300 MHz,CDCl$_3$) δ 7.71 (d, 1H, J=2.2 Hz), 7.54 (dd, 1H, J=8.4 Hz, J=2.2 Hz), 7.35 (d, 1H, J=8.4 Hz), 6.91 (bs, 1H), 6.44 (s, 1H), 2.31 (s, 3H), 2.28 (m, 2H), 1.14 (m, 3H). $^{13}$C NMR (75 MHz,CDCl$_3$) δ 150.61, 137.18, 134.68, 133.02, 132.62, 131.39, 123.73, 99.01, 29.82, 14.04, 9.30. Anal. Calcd. for C$_{13}$H$_{13}$BrClN$_3$O: C, 45.57; H, 3.82; N, 12.26. Found: C, 45.76; H, 3.83; N, 12.26.

Step C: The compound prepared in Step B (4.1 g, 12.0 mmol) was suspended in tetrahydrofuran (30 mL). To this suspension was added borane/THF complex (36.0 mL, 36.0 mmol), and the reaction refluxed for 3 hours. The reaction was cooled to room temperature and excess borane was quenched with 10% NaOH (10 mL) until off-gassing ceased and the reaction was diluted with water and diethyl ether. The layers were separated and the organic phase was washed with saturated sodium chloride, dried over anhydrous anhydrous magnesium sulfate, and reduced in vacuo. This residue was purified by column chromatography (25% ethyl acetate/hexanes) to provide the final product as a white solid (3.46 g, 88%), mp 140–141.5° C. $^1$H NMR (300 MHz, CDCl$_3$) δ 7.75 (d, 1H, J=2.2 Hz), 7.59 (dd, 1H, J=8.5 Hz, J=2.2 Hz), 7.31 (d, 1H, J=8.4 Hz), 5.39 (s, 1H), 3.43 (t, 1H, J=5.9 Hz), 3.07 (m, 2H), 2.38 (s, 3H), 1.57 (m, 2H), 0.90 (t, 3H, J=7.5 Hz). $^{13}$C NMR (75 MHz,CDCl$_3$) δ 149.79, 149.42, 135.79, 133.45, 133.33, 131.34, 130.94, 125.56, 87.10, 46.66, 22.51, 14.01, 11.15.

Step D: The compound prepared in Step C (2.76 g, 8.40 mmol) was suspended in ethanol (20 mL), and 15 drops of 10% HCl were added. Upon addition of the HCl significant off-gassing occurred, and at the completion of the off-gassing the reaction mixture was homogeneous. Isoamyl nitrite (1.35 mL, 10.1 mmol) was then added, and the solution darkened upon addition. The solution was stirred at room temperature for 16 hours, and then reduced to dryness in vacuo. The residue was purified by column chromatography (gradient elution of 25–50% ethyl acetate/hexanes) to give the final product as purple crystals (2.16 g, 72%), mp 118.5–119.5° C. $^1$H NMR (300 MHz,CDCl$_3$) δ 10.30 (bs, 1H), 7.72 (d, 1H, J=2.2 Hz), 7.57 (dd, 1H, J=8.5 Hz, J=2.2 Hz), 7.40 (d, 1H, J=8.5 Hz), 2.72 (m, 2H), 2.70 (s, 3H), 1.45 (m, 2H), 0.82 (t, 3H, J=7.3 Hz). $^{13}$C NMR (75 MHz,CDCl$_3$) δ 152.98, 149.91, 149.01, 135.40, 134.37, 132.92, 131.23, 131.01, 124.69, 43.90, 22.76, 11.45, 10.95. Anal Calcd. for C$_{13}$H$_{14}$BrClN$_4$O: C, 43.66; H, 3.95; N, 15.67. Found: C, 43.85; H, 3.96; N, 15.69.

Step E: The compound prepared in Step D (2.06 g, 5.76 mmol) was dissolved in anhydrous pyridine (30 mL) and the solution heated to reflux for 16 hours. The solvent was removed in vacuo and the residue was purified by column chromatography (50% ethyl acetate/hexanes) to recover the product as a brown solid (0.83 g, 42%). This product was used in further reactions directly, however a sample was further purified for analytical purposes by washing briefly with 50% diethyl ether/hexanes to remove a brown oily residue, leaving the final product as an off-white solid, mp 175.5–178.5° C. $^1$H NMR (300 MHz,CDCl$_3$) δ 8.69 (bs, 1H), 7.67 (d, 1H, J=1.8 Hz), 7.45 (m, 2H), 2.87 (q, 2H, J=7.5 Hz), 2.45 (s, 3H), 1.38 (t, 3H, J=7.7 Hz). $^{13}$C NMR (75 MHz,CDCl$_3$) 157.73, 152.93, 136.01, 133.16, 130.80, 130.59, 128.94, 121.14, 120.31, 23.29, 12.91, 12.55.

Step F: The compound prepared in Step E (500 mg, 1.47 mmol) was dissolved in anhydrous dimethylformamide (15 mL) and sodium bis(trimethylsilyl)amide (0.6 M in toluene, 6.1 mL, 3.68 mmol) was added. The solution was heated to 60° C. for one hour, then 1-bromobutane (0.63 mL, 5.88 mmol) was added. The reaction was held at 60° C. for 4 hours, cooled to room temperature, and diluted with water and diethyl ether. The layers were separated and the organic phase washed with water, dried over anhydrous magnesium sulfate, and reduced to dryness in vacuo. The residue was purified by column chromatography (33% ethyl acetate/hexanes) to give the final product as an oil (303 mg, 52%). $^1$H NMR (300 MHz,CDCl$_3$) δ 7.67 (d, 1H, J=1.8 Hz), 7.44 (m, 2H), 4.01 (t, 2H, J=7.4 Hz), 2.79 (q, 2H, J=7.6 Hz), 2.51 (s, 3H), 1.83 (m, 2H), 1.43 (m, 2H), 1.35 (t, 3H, J=7.5 Hz), 1.00 (t, 3H, J=7.3 Hz). $^{13}$C NMR (75 MHz,CDCl$_3$) δ 157.15, 136.17, 133.25, 130.64, 130.53, 128.88, 120.82, 44.89, 33.54, 21.24, 19.99, 13.74, 12.99, 12.80.

EXAMPLE 326

Preparation of 4-(3,4-Difluorobenzyl)-5-ethyl-3-methyl-1-(2-chloro-4-bromo)phenylimidazo[4,5-c]pyrazole The product from Step E, Example 325 (50 mg, 0.15 mmol) was dissolved in anhydrous dimethylformamide (1 mL) and sodium bis(trimethylsilyl)amide (0.6 M in toluene, 0.61 mL, 0.37 mmol) was added. The solution was heated to 60° C. for one hour, then α-bromo-3,4-difluorotoluene (0.075 mL, 0.59 mmol) was added. The reaction was held at 60° C. for 4 hours, cooled to room temperature, and diluted with water and diethyl ether. The layers were separated and the organic phase was washed with water, dried over anhydrous magnesium sulfate, and reduced to dryness in vacuo. The residue was purified by column chromatography (33% ethyl acetate/hexanes) to give the final product as a solid (30 mg, 13%), mp 114–116° C. $^1$H NMR (300 MHz,CDCl$_3$) δ 7.68 (d, 1H, J=1.5 Hz), 7.46 (m, 2H), 7.21 (m, 1H), 6.95 (m, 2H), 5.21 (s, 2H), 2.79 (q, 2H, J=7.5 Hz), 2.19 (s, 3H), 1.32 (t, 3H, J=7.5 Hz). $^{13}$C NMR (75 MHz,CDCl$_3$) δ 157.62, 135.96, 133.29, 130.75, 130.61, 128.96, 122.23, 121.13, 118.20, 117.97, 115.54, 115.30, 47.44, 21.38, 12.65, 12.54.

EXAMPLE 327

Preparation of 4-[1-(1-Ethyl)butane]-5-ethyl-3-methyl-1-(2-chloro-4-bromo)phenylimidazo[4,5-c]pyrazole The product from Step E, Example 325 (110 mg, 0.32 mmol) was dissolved in anhydrous dimethylformamide (4 mL) and sodium bis(trimethylsilyl)amide (0.6 M in toluene, 1.3 mL, 0.8 mmol) was added. The solution was heated to 60° C. for one hour, then 3-bromohexane (211 mg, 1.28 mmol) was added. The reaction was held at 100° C. for 64 hours, then cooled to room temperature and diluted with water and diethyl ether. The layers were separated and the organic phase was washed with water, dried over anhydrous magnesium sulfate, and reduced to dryness in vacuo. The residue was purified by column chromatography (33% ethyl acetate/hexanes) to give the final product as an oil (19 mg, 14%). $^1$H NMR (300 MHz,CDCl$_3$) δ 7.67 (t, 1H, J=1.1 Hz), 7.46 (d, 2H, J=1.1 Hz), 4.01 (m, 1H), 2.82 (q, 2H, J=7.5 Hz), 2.53 (s, 3H), 1.86 (m, 4H), 1.35 (t, 3H, J=7.5 Hz), 1.26 (m, 2H), 0.92 (t, 3H, 7.2 Hz), 0.85 (t, 3H, J=7.3 Hz). $^{13}$C NMR (75 MHz,CDCl$_3$) δ 157.85, 152.75, 136.08, 133.29, 130.72, 130.66, 130.52, 128.92, 120.84, 119.95, 58.19, 38.40, 29.47, 22.32, 21.94, 19.83, 15.43, 13.87, 12.91, 11.14.

EXAMPLE 328

Preparation of 5-Ethyl-4-[1-(1-methyl)butane]-3-methyl- 1-(2-chloro-4-bromo)phenylimidazo[4,5-c]pyrazole The product from Step E, Example 325 (110 mg, 0.32 mmol) was dissolved in anhydrous dimethylformamide (4 mL) and sodium bis(trimethylsilyl)amide (0.6 M in toluene, 1.3 mL, 0.8 mmol) was added. The solution was heated to 60° C. for one hour, then 2-bromopentane (0.16 mL, 1.28 mmol) was added. The reaction was held at 100° C. for 64 hours, then cooled to room temperature and diluted with water and diethyl ether. The layers were separated and the organic phase was washed with water, dried over anhydrous magnesium sulfate, and reduced to dryness in vacuo. The residue was purified by column chromatography (33% ethyl acetate/hexanes) to give the final product as an oil (27 mg, 20%). $^1$H NMR (300 MHz,CDCl$_3$) δ 8 7.67 (d, 1H, J=1.4 Hz), 7.45 (m, 2H), 4.31 (m, 1H), 2.83 (q, 2H, J=7.7 Hz), 2.56 (s, 3H), 1.84 (m, 2H), 1.54 (d, 3H, J=6.6 Hz), 1.33 (t, 3H, J=7.5 Hz), 1.25 (m, 2H), 0.93 (t, 3H, J=7.3 Hz). $^{13}$C NMR (75 MHz,CDCl$_3$) δ 156.94, 152.63, 136.07, 133.26, 130.65, 130.60, 130.53, 128.92, 120.85, 120.07, 51.77, 39.77, 22.30, 22.00, 19.87, 15.50, 13.78, 12.98.

EXAMPLE 329

Preparation of 4-(n-Butyl)-5-ethyl-3-methyl-1-(2-chloro-4-methyl)phenylimidazo[4,5-c]pyrazole Step A: β-Aminocrotonitrile (4.53 g, 0.06 mol) was dissolved in 1.0N HCl (90 ml) and treated with 2-chloro-4-methylhydrazine (8.66 g, 0.06 mol). The reaction was allowed to reflux for 6 h, cooled, and decanted into a 2 liter beaker. The solution was diluted with water (250 ml) and neutralized with 10% NaOH. The resulting solution was extracted with Et$_2$O (4×30 ml) and the combined organic extracts were dried over MgSO$_4$, filtered and concentrated in-vacuo to afford 2.29 g (17.2%) of the desired aminopyrazole as a red oil. $^1$H NMR (300 Mhz, CDCl$_3$) δ 7.34 (m, 2H), 7.19 (m, 1H), 5.46 (s, 1H), 3.56 (bs, 2H), 2.39 (s, 3H), 2.24 (s, 3H).

Step B: The compound prepared in Step A (0.97 g, 4.37 mmol) was suspended in propionic anhydride (2.8 mL, 21.9 mmol) at room temperature and allowed to stir for 16 hours. Ice was added and the reaction stirred for 24 hours. Diethyl ether was added and the phases separated. The organic phase was washed with saturated sodium chloride and dried over anhydrous magnesium sulfate and reduced in vacuo to leave a thick oil. This residue was purified by column chromatography (50% ethyl acetate/hexanes) to give the final product as a solid (1.0 g, 85%), mp 115–116.5° C. $^1$H NMR (300 MHz,CDCl$_3$) 7.33 (m, 2H), 7.21 (d, 1H, J=8.0 Hz), 6.91 (bs, 1H), 6.48 (s, 1H), 2.42 (s, 3H), 2.32 (s, 3H), 2.27 (q, 2H, J=7.5), 1.14 (t, 3H, J=7.5 Hz). $^{13}$C NMR (75 MHz,CDCl$_3$) δ 149.99, 141.42, 137.22, 132.64, 131.25, 130.72, 129.95, 128.83, 97.88, 29.87, 21.03, 14.05, 9.30. Anal. Calcd. for C$_{14}$H$_{16}$ClN$_3$O: C, 60.54; H, 5.82; N, 15.13. Found: C, 60.60; H, 5.79; N, 15.10.

Step C: The compound prepared in Step B (0.94 g, 3.4 mmol) was suspended in anhydrous tetrahydrofuran (20 mL). To this suspension was added borane/THF complex (10.2 mL, 10.2 mmol), and the reaction was refluxed for 1.5 hours. The reaction was cooled to room temperature and excess borane was quenched with 10% NaOH (10 mL) until off-gassing ceased and the reaction was diluted with water and diethyl ether. The layers were separated and the organic phase was washed with saturated sodium chloride, dried over anhydrous magnesium sulfate, and reduced in vacuo. This residue was purified by column chromatography (25% ethyl acetate/hexanes) to provide the final product as a white solid (0.76 g, 85%), mp 100.5–101.5° C. $^1$H NMR (300 MHz,CDCl$_3$) δ 7.39 (d, 1H, J=0.8 Hz), 7.31 (d, 1H, J=8.4 Hz), 7.24 (dd, 1H, J=8.1 Hz, J=1.1 Hz), 5.38 (s, 1H), 3.43 (t, 1H, J=5.6 Hz), 3.07 (m, 2H), 2.43 (s, 3H), 2.38 (s, 3H), 1.55 (m, 2H), 0.89 (t, 3H, J=7.4 Hz). $^{13}$C NMR (75 MHz, CDCl$_3$) δ 149.46, 149.13, 142.88, 134.16, 131.77, 131.06, 129.00, 128.69, 86.85, 46.63, 22.54, 21.25, 14.04, 11.14.

Step D: The compound prepared in Step C (0.69 g, 2.62 mmol) was suspended in ethanol (10 mL), and 15 drops of 10% HCl were added. Upon addition of the HCl significant off-gassing occurred, and at the completion of the off-gassing the reaction mixture was homogeneous. Isoamyl nitrite (0.42 mL, 3.14 mmol) was then added, and the solution darkened upon addition. The solution was stirred at room temperature for 16 hours, and then reduced to dryness-in vacuo. The residue was purified by column chromatography (gradient elution of 25–50% ethyl acetate/hexanes) to give the final product as purple crystals (0.37 g, 48%), mp 83–85° C. $^1$H NMR (300 MHz,CDCl$_3$) δ 10.28 (bs, 1H), 7.38 (d, 1H, J=8.1 Hz), 7.34 (d, 1H, J=1.9 Hz), 7.20 (dd, 1H, J=8. Hz, J=2.2 Hz), 2.72 (m, 2H), 2.70 (s, 3H), 1.42 (m, 2H), 0.78 (t, 3H, J=7.5 Hz). $^{13}$C NMR (75 MHz,CDCl$_3$) δ 152.51, 142.33, 139.08, 130.52, 129.62, 128.55, 43.63, 22.82, 21.13, 11.45, 10.94. Anal. Calcd. for C$_{14}$H$_{17}$ClN$_4$O: C, 57.44; H, 5.85; N, 19.14. Found: C, 57.51; H, 5.83; N, 19.03.

Step E: The compound prepared in Step D (0.34 g, 1.15 mmol) was dissolved in anhydrous pyridine (5 mL) and the solution heated to reflux for 16 hours. The solvent was removed in vacuo and the residue purified by column chromatography (75% ethyl acetate/hexanes) to afford the product as a brown solid (0.2 g, 60%). This product was used in further reactions directly, however a sample was further purified for analytical purposes by washing briefly with diethyl ether to remove a brown oily residue, leaving the final product as an off-white solid, mp 178–180° C. $^1$H NMR (300 MHz,CDCl$_3$) δ 9.46 (bs, 1H), 7.39 (d, 1H, J=8.1 Hz), 7.28 (d, 1H, J=1.1 Hz), 7.09 (dd, 1H, J=8.0, J=1.1), 2.80 (g, 2H, J=7.7 Hz), 2.41 (s, 3H), 2.34 (s, 3H), 1.32 (t, 3H, J=7.7 Hz). 13C NMR (75 MHz,CDCl$_3$) δ 157.73, 153.03, 139.18, 134.15, 130.78, 129.92, 129.74, 128.07, 127.89, 120.13, 23.23, 20.85, 12.86, 12.58. Anal. Calcd. for C$_{14}$H$_{15}$ClN$_4$: C, 61.20; H, 5.50; N, 20.39; Cl, 12.90. Found: C, 61.18; H, 5.9; N, 20.34; Cl, 12.78.

Step F: The compound prepared in Step E (50 mg, 0.18 mmol) was dissolved in anhydrous dimethylformamide (1.5 mL) and sodium bis(trimethylsilyl)amide (0.6 M in toluene, 0.75 mL, 0.45 mmol) was added. The solution was heated to 60° C. for one hour, then 1-bromobutane (0.078 mL, 0.73 mmol) was added. The reaction was held at 60° C. for 2 hours, cooled to room temperature, and diluted with water and diethyl ether. The layers were separated and the organic phase washed with water, dried over anhydrous magnesium sulfate, and reduced to dryness in vacuo. The residue was purified by column chromatography (33% ethyl acetate/hexanes) to give the final product as an oil (45 mg, 75%). $^1$H NMR (300 MHz,CDCl$_3$) δ 7.41 (d, 1H, J=8.1 Hz), 7.31 (d, 1H, J=1.1 Hz), 7.10 (dd, 1H, J=8.1 Hz, J=1.1 Hz) 4.01 (t, 2H, J=7.5 Hz), 2.79 (q, 2H, J=7.3 Hz), 2.51 (s, 3H), 2.36 (s, 3H), 1.83 (m, 2H), 1.43 (m, 2H), 1.34 (t, 3H, J=7.7 Hz), 0.99 (t, 3H, J=7.3 Hz). $^{13}$C NMR (75 MHz,CDCl$_3$) δ 156.98, 152.05, 138.85, 134.31, 130.87, 129.69, 129.64, 128.05, 127.91, 121.98, 44.85, 33.55, 21.26, 20.85, 19.99, 13.75, 13.01, 12.87.

EXAMPLE 330

Preparation of 5-Ethyl-4-[1-(1-methyl)butane]-3-methyl-1-(2-chloro-4-methyl)phenylimidazo[4,5-c]pyrazole The product from Step E, Example 329 (116 mg, 0.42 mmol) was dissolved in anhydrous dimethylformamide (3.5 mL) and sodium bis(trimethylsilyl)amide (0.6 M in toluene, 1.75 mL, 1.05 mmol) was added. The solution was heated to 60° C. for one hour, then 2-bromopentane (0.21 mL, 1.69 mmol) was added. The reaction was held at 100° C. for 40 hours, then cooled to room temperature and diluted with water and diethyl ether. The layers were separated and the organic phase washed with water, dried over anhydrous magnesium sulfate, and reduced to dryness in vacuo. The residue was purified by column chromatography (33% ethyl acetate/hexanes) to give the final product as an oil (23 mg, 16%). $^1$H NMR (300 MHz,CDCl$_3$) δ 7.41 (d, 1H, J=8.1 Hz), 7.32 (s, 1H), 7.12 (d, 1H, J=8.1 Hz) 4.28 (m, 1H), 2.83 (q, 2H, J=7.5 Hz), 2.57 (s, 3H), 2.36 (S, 3H), 1.85 (m, 2H), 1.54 (d, 3H, J=6.6 Hz), 1.33 (t, 3H, J=7.5 Hz), 1.29 (m, 2H), 0.92 (t, 3H, J=7.0 Hz). $^{13}$C NMR (75 MHz,CDCl$_3$) δ 156.77, 152.76, 138.86, 134.23, 130.91, 129.74, 129.67, 128.05, 127.95, 119.73, 51.69, 39.79, 22.31, 22.02, 20.85, 19.87, 15.51, 13.80, 13.07.

EXAMPLE 331

Preparation of 4-(n-Butyl)-5-ethyl-3-methyl-1-(2-chloro-4-trifluoromethyl)phenylimidazo[4,5-c]pyrazole Step A: β-Aminocrotonitrile (8.39 g, 0.10 mol) was dissolved in 1.0N HCl (350 ml) and treated with 2-chloro-4-trifluoromethylhydrazine (21.52 g, 0.10 mol). The reaction was allowed to reflux for 2.5 h, cooled, and decanted into a 2 liter beaker. The solution was diluted with water (250 ml) and neutralized with 10% NaOH. The resulting precipitate was filtered and dried to constant weight to afford 23.61 g (83%) of the desired aminopyrazole as a white crystalline solid, mp 158.0–160.0° C. $^1$H NMR (300 Mhz, CDCl$_3$) δ 7.80 (s, 1H), 7.64 (m, 2H), 5.50 (s, 1H), 3.62 (bs, 2H), 2.25 (s, 3H).

Step B: The compound prepared in Step A (4.0 g, 14.5 mmol) was dissolved in propionic anhydride (9.3 mL, 72.5 mmol) at room temperature and was allowed to stir for 16 hours. Ice was then added and the reaction stirred for 5 hours. The solid product was removed by filtration, washed with water, and dried in vacuo to leave the final product as a yellow solid (3.75 g, 78%), mp 135–138° C. $^1$H NMR (300 MHz,CDCl$_3$) δ 7.81 (s, 1H), 7.66 (m, 2H), 6.93 (bs, 1H), 6.43 (s, 1H), 2.32 (s, 3H), 2.28 (q, 2H, J=7.7 Hz), 1.13 (t, 3H, J=7.7 Hz). $^{13}$C NMR (75 MHz,CDCl$_3$) δ 170.92, 151.05, 138.79, 137.13, 132.02, 130.94, 127.64, 125.03, 124.57, 99.79, 29.82, 14.05, 9.27. Anal. Calcd for C$_{14}$H$_{13}$ClF$_3$N$_3$O: C, 50.69; H,3.95; N, 12.67. Found: C, 51.00; H, 4.05; N, 12.27.

Step C: The compound prepared in Step B (3.63 g, 10.9 mmol) was suspended in tetrahydrofuran (30 mL). To this suspension was added borane/THF complex (32.8 mL, 32.8 mmol), and the reaction refluxed for one hour, then held at room temperature for 16 hours. Excess borane was quenched with 10% NaOH (10 mL) until off-gassing ceased and the reaction was diluted with water and diethyl ether. The layers were separated and the organic phase as washed with saturated sodium chloride, dried over anhydrous magnesium sulfate, and reduced in vacuo. This residue was purified by column chromatography (25% ethyl acetate/hexanes) to provide the final product as a white solid (2.73 g, 79%), mp 139–140° C. $^1$H NMR (300 MHz,CDCl$_3$) δ 7.85 (d, 1H, J=1.9 Hz), 7.72 (dd, 1H, J=8.1 Hz, J=1.5 Hz), 7.60 (d, 1H, J=8.4 Hz), 5.43 (s, 1H), 3.42 (t, 1H, J=5.6 Hz), 3.10 (m, 2H), 2.40 (s, 3H), 1.57 (m, 2H), 0.91 (t, 3H, J=7.5 Hz). $^{13}$C NMR (75 MHz,CDCl$_3$) δ 150.25, 149.43, 135.64, 135.10, 133.08, 127.91, 127.86, 124.95, 124.90, 87.32, 46.70, 22.49, 13.99, 11.14.

Step D: The compound prepared in Step C (2.83 g, 8.91 mmol) was suspended in ethanol (22 mL), and 15 drops of 10% HCl were added. Upon addition of the HCl significant off-gassing occurred, and at the completion of the off-gassing the reaction mixture was homogeneous. Isoamyl nitrite (1.4 mL, 10.7 mmol) was then added, and the solution darkened upon addition. The solution was stirred at room temperature for 16 hours, and then reduced to dryness in vacuo. Hexanes were added to the residual oil and a yellow precipitate formed. This solid was removed by filtration and washed with hexanes, and was later identified as the hydrochloride salt of the desired product (0.51 g, 17%). The filtrate was reduced in vacuo and the residual oil was purified by column chromatography (gradient elution with 25–50% ethyl acetate/hexanes) to give the final product as reddish purple crystals (2.03 g, 66%), mp 95–97° C. $^1$H NMR (300 MHz,CDCl$_3$) δ 10.34 (bs, 1H), 7.83 (s, 1H), 7.70 (m, 2H), 2.73 (s, 3H), 2.70 (m, 2H), 1.45 (m, 2H), 0.81 (t, 3H, J=7.3 Hz). $^{13}$C NMR (75 MHz,CDCl$_3$) δ 153.31, 149.87, 139.45, 139.01, 134.13, 133.84, 130.65, 127.49, 127.44, 124.92, 124.88, 44.10, 22.73, 11.48, 10.89. Anal Calcd. for C$_{14}$H$_{14}$ClF$_3$N$_4$O: C, 48.50; H, 4.08; N, 16.16. Found: C, 48.53; H, 4.11; N, 16.04.

SteP E: The compound prepared in Step D (1.92 g, 5.55 mmol) was dissolved in anhydrous pyridine (30 mL) and the solution heated to reflux for 16 hours. The solvent was removed in vacuo and the residue purified by column chromatography (50% ethyl acetate/hexanes) to afford the product as a brown solid (0.74 g, 41%). This product was used in further reactions directly, however a sample was further purified for analytical purposes by washing briefly with 50% diethyl ether/hexanes to remove a brown oily residue, leaving the final product as an off-white solid, mp 155.5–158° C. $^1$H NMR (300 MHz,CDCl$_3$) δ 8.76 (bs, 1H), 7.78 (d, 1H, J=1.5 Hz), 7.76 (d, 1H, J=8.4 Hz), 7.59 (dd, 1H, J=8.4 Hz, J=1.5 Hz), 2.88 (q, 2H, J=7.6 Hz), 2.47 (s, 3H), 1.38 (t, 3H, J=7.5 Hz). $^{13}$C NMR (75 MHz,CDCl$_3$) δ 157.50, 152.94, 139.71, 131.59, 130.85, 130.40, 129.96, 129.39, 128.13, 128.08, 127.74, 124.92, 124.37, 124.33, 121.32, 120.63, 23.28, 12.90, 12.52. Anal. Calcd. for C$_{14}$H$_{12}$ClF$_3$N$_4$: C, 51.15; H, 3.69; N, 17.04; Cl, 10.79; F, 17.34. Found: C, 51.37; H, 3.77; N, 16.92; Cl, 10.96; F, 16.98.

Step F: The compound prepared in Step E (160 mg, 0.49 mmol) was dissolved in dimethylformamide (5 mL) and sodium bis(trimethylsilyl)amide (0.6 M in toluene, 2.0 mL, 1.22 mmol) was added. The solution was heated to 60° C. for one hour, then 1-bromobutane (0.21 mL, 1.96 mmol) was added. The reaction was held at 60° C. for 1.5 hours, cooled to room temperature, and diluted with water and diethyl ether. The layers were separated and the organic phase washed with water, dried over anhydrous sodium sulfate, and reduced in vacuo. The residue was purified by preparative thin layer chromatography (33% ethyl acetate/hexanes) to give the final product as an oil (83 mg, 44%). $^1$H NMR (300 MHz,CDCl$_3$) δ 7.78 (d, 1H, J=1.5 Hz), 7.73 (d, 1H, J=8.4 Hz), 7.58 (dd, 1H, J=8.4 Hz, J=1.5 Hz), 4.00 (t, 2H, J=7.5 Hz), 2.80 (q, 2H, J=7.5 Hz), 2.52 (s, 3H), 1.81 (m, 2H), 1.44 (m, 2H), 1.36 (t, 3H, J=7.7 Hz), 1.00 (t, 3H, J=7.3 Hz). $^{13}$C NMR (75 MHz,CDCl$_3$) δ 157.22, 151.95, 139.84, 131.45, 130.06, 129.61, 129.23, 128.24, 128.18, 127.58, 125.02, 124.34, 124.29, 122.62, 44.92, 33.56, 21.24, 19.99, 13.73, 13.01, 12.76

EXAMPLE 332

Preparation of 4-(3,4-Difluorobenzyl)-5-ethyl-3-methyl-1-(2-chloro-4-trifluoromethyl)phenylimidazo [4,5-c]pyrazole The product from Step E, Example 331 (160 mg, 0.49 mmol) was dissolved in anhydrous dimethylformamide (5 mL) and sodium bis(trimethylsilyl)amide (0.6 M in toluene, 2.0 mL, 1.22 mmol) was added. The solution was heated to 60° C. for one hour, then a-bromo-3,4-difluorotoluene (0.25 mL, 1.96 mmol) was added. The reaction was held at 60° C. for 2.5 hours, cooled to room temperature, and diluted with water and diethyl ether. The layers were separated and the organic phase washed with water, dried over anhydrous sodium sulfate, and reduced to dryness in vacuo. The residue was purified by column chromatography (33% ethyl acetate/hexanes) followed by recrystallization from diethyl ether/hexanes to give the final product (30 mg, 13%), mp 108–110° C. $^1$H NMR (300 MHz,CDCl$_3$) δ 8 7.80 (d, 1H, J=1.5 Hz), 7.75 (d, 1H, J=8.4 Hz), 7.61 (dd, 1H, J=8.4 Hz, J=1.5 Hz), 7.19 (m, 1H), 6.93 (m, 2H), 5.22 (s, 2H), 2.81 (q, 2H, J=7.5 Hz), 2.21 (s, 3H), 1.33 (t, 3H, J=7.5 Hz). $^{13}$C NMR (75 MHz,CDCl$_3$) δ 157.67, 151.98, 151.69, 139.65, 133.27, 131.52, 130.33, 129.89, 129.33, 128.25, 128.21, 127.71, 124.99, 124.39, 124.35, 122.54, 122.29, 122.20, 118.24, 118.01, 115.55, 115.30, 47.46, 21.39, 12.62, 12.58.

EXAMPLE 333

Preparation of 4-[1-(1-Ethyl)butane]-5-ethyl-3-methyl-1-(2-chloro-4-trifluoromethyl)phenylimidazo [4,5-c]pyrazole The product from Step E, Example 331 (150 mg, 0.45 mmol) was dissolved in anhydrous dimethylformamide (5 mL) and sodium bis(trimethylsilyl)amide (0.6 M in toluene, 1.9 mL, 1.14 mmol) was added. The solution was heated to 60° C. for one hour, then 3-bromohexane (300 mg, 1.82 mmol) was added. The reaction was held at 80° C. for 64 hours, then cooled to room temperature and diluted with water and diethyl ether. The layers were separated and the organic phase washed with water, dried over anhydrous magnesium sulfate, and reduced to dryness in vacuo. The residue was purified by column chromatography (33% ethyl acetate/hexanes) to give the final product as an oil (31 mg, 16%). $^1$H NMR (300 MHz,CDCl$_3$) δ 7.77 (m, 2H), 7.59 (dd, 1H, J=8.4 Hz, J=1.5 Hz), 4.02 (m, 1H), 2.83 (g, 2H, J=7.5 Hz), 2.55 (s, 3H), 1.85 (m, 4H), 1.36 (t, 3H, J=7.7 Hz), 1.27 (m, 2H), 0.92 (t, 3H, J=7.2 HZ), 0.86 (t, 3H, J=7.3 Hz). $^{13}$C NMR (75 MHz,CDCl$_3$) δ 157.91, 152.73, 139.73, 131.50, 130.06, 129.62, 129.31, 128.26, 128.22, 127.60, 125.03, 124.32, 124.27, 121.43, 120.26, 58.24, 38.41, 37.35, 29.48, 21.94, 19.83, 15.47, 13.87, 12.88, 11.14.

EXAMPLE 334

Preparation of 5-Ethyl-4-[1-(1-methyl)butane]-3-methyl-1-(2-chloro-4-trifluoromethyl)phenylimidazo [4,5-c]pyrazole The product from Step E, Example 501 (150 mg, 0.45 mmol) was dissolved in anhydrous dimethylformamide (5 mL) and 10 sodium bis(trimethylsilyl)amide (0.6 M in toluene, 1.9 mL, 1.14 mmol) was added. The solution was heated to 60° C. for one hour, then 2-bromopentane (0.22 mL, 1.82 mmol) was added. The reaction was held at 80° C. for 64 hours, then cooled to room temperature and diluted with water and diethyl ether. The layers were separated and the organic phase washed with water, dried over anhydrous magnesium sulfate, and reduced to dryness in vacuo. The residue was purified by column chromatography (gradient elution with 33–50% ethyl acetate/hexanes) to give the final product as an oil (37 mg, 21%). $^1$H NMR (300 MHz,CDCl$_3$) δ 7.79 (d, 1H, J=1.5 Hz), 7.75 (d, 1H, J=8.1 Hz), 7.59 (dd, 1H, J=8.4 Hz, J=1.5 Hz), 4.30 (m, 1H), 2.84 (q, 2H, J=7.5 Hz), 2.58 (s, 3H), 1.86 (m, 2H), 1.55 (d, 3H, J=6.6 Hz), 1.34 (t, 3H, J=7.5 Hz), 1.22 (m, 2H), 0.93 (t, 3H, J=7.3 Hz). $^{13}$C NMR (75 MHz,CDCl$_3$) δ 157.01, 139.73, 131.43, 129.31, 128.24, 128.20, 127.63, 124.32, 124.27, 120.40, 51.83, 39.77, 22.29, 21.99, 19.86, 15.52, 13.77, 12.93.

EXAMPLE 353

Preparation of 4-(n-Butyl)-5-ethyl-3-methyl-1-(2-chloro-4-methoxy)phenylimidazo[4,5-c]pyrazole This compound was obtained as the second eluting compound from the reaction described in Example 355 (see below) (12 mg, 8%) as a yellow oil. $^1$H NMR (300 MHz, CDCl$_3$) δ 7.42 (d, 1H, J=8.8 Hz), 7.03 (d, 1H, J=2.6 Hz), 6.86 (dd, 1H, J=8.8 Hz, J=2.5 Hz), 4.01 (t, 2H, J=7.3 Hz), 3.82 (s, 3H), 2.79 (q, 2H, J=7.7 Hz), 2.51 (s, 3H), 1.73 (m, 2H), 1.44 (m, 2H), 1.34 (t, 3H, J=7.5), 1.00 (t, 3H, J=7.3 Hz). HRMS Calcd. for M+H ($C_{18}H_{24}ClON_4$): 347.1638. Found: 347.1642.

EXAMPLE 354

Preparation of 4-(n-Butyl)-5-ethyl-3-methyl-1-(2,4-dimethoxy)phenylimidazo[4,5-c]pyrazole This compound was obtained as the third eluting compound from the reaction described in Example 520 (29 mg, 19%) as a yellow oil. $^1$H NMR (300 MHz,CDCl$_3$) δ 7.35 (d, 1H, J=8.8 Hz), 6.57 (d, 1H, J=2.5 Hz), 6.52 (dd, 1H, J=8.6 Hz, J=2.7 Hz), 3.99 (t, 2H, J=7.3 Hz), 3.82 (s, 3H), 3.80 (s, 3H), 2.77 (q, 2H, J=7.7 Hz), 2.50 (s, 3H), 1.82 (m, 2H), 1.43 (m, 2H), 1.33 (t, 3H, J=7.5 Hz), 0.99 (t, 3H, J=7.5 Hz). HRMS Calcd. for M+H ($C_{19}H_{27}CO_2N_4$): 343.2134. Found: 343.2117.

EXAMPLE 355

Preparation of 4-(n-Butyl)-5-ethyl-3-methyl-1-(2-methoxy-4-bromo)phenylimidazo[4,5-c]pyrazole The compound prepared in Step F, Example 325 (178 mg, 0.45 mmol) was dissolved in anhydrous dimethylformamide (2.2 mL). To this solution was added CuBr (9.7 mg, 0.0676 mmol), followed by sodium methoxide (25% in methanol, 0.29 mL, 1.35 mmol). This solution was heated to 155° C. for 30 minutes, cooled to room temperature, and diluted with diethyl ether. This solution was shaken with a 20% solution of NH$_4$OH in saturated aqueous NH$_4$Cl, and the ethereal phase was dried over anhydrous magnesium sulfate and reduced in vacuo to leave a brown oil. This residue was purified by column chromatography (gradient elution with 50–75% ethyl acetate/hexanes), the first eluting compound being the title product as a yellow oil (27 mg, 15%). Further elution provided Examples 521 and 522, described below. $^1$H NMR (300 MHz,CDCl$_3$) δ 7.37 (m, 1H), 7.15 (m, 2H), 3.99 (t, 2H, J=7.3 Hz), 3.86 (s, 3H), 2.78 (q, 2H, J=7.7 Hz), 2.50 (s, 3H), 1.82 (m, 2H), 1.43 (m, 2H), 1.35 (t, 3H, J=7.5 Hz), 0.99 (t, 3H, J=7.5 Hz). HRMS Calcd. for M+H ($C_{18}H_{24}BrON_4$): 391.1134. Found: 391.1133.

EXAMPLE 356

Preparation of 5-Ethyl-4-[1-(1-methyl)butane]-3-methyl-1-(2,6-dichloro-4-methoxy)phenylimidazo[4,5-c]pyrazole The compound prepared in Example 102 (296 mg, 0.74 mmol) was dissolved in anhydrous dimethylformamide (3.5 mL). To this solution was added CuBr (16 mg, 0.11 mmol), followed by sodium methoxide (25% in methanol, 0.25 mL, 1.11 mmol). This solution was heated to 75° C. for 30 minutes, then additional sodium methoxide (0.050 mL, 0.22 mmol) was added and the reaction was heated to 100° C. for two hours. The reaction was cooled to room temperature and and diluted with diethyl ether. This solution was shaken with a 20% solution of NH$_4$OH in saturated aqueous NH$_4$Cl, and the ethereal phase was dried over anhydrous magnesium sulfate and reduced in vacuo to leave a yellow oil. This residue was purified by column chromatography (gradient elution with 25–50% ethyl acetate/hexanes), the first eluting compound being the title product as an oil (39 mg, 13%). Further elution provided Example 524, described below. $^1$H NMR (300 MHz,CDCl$_3$) δ 6.95 (s, 2H), 4.28 (m, 1H), 3.82 (s, 3H), 2.82 (q, 2H, J=7.7 Hz), 2.56 (s, 3H), 1.877 (m, 2H), 1.55 (d, 3H, J=7.0 Hz), 1.33 (t, 3H, J=7.5 Hz), 0.92 (t, 3H, J=7.3 Hz). HRMS Calcd. for M+H ($C_{19}H_{25}Cl_2ON_4$): 395.1405. Found: 395.1406.

EXAMPLE 357

Preparation of 5-Ethyl-4-[1-(1-methyl)butane]-3-methyl-1-(2,4-dichloro-6-methoxy)phenylimidazo[4,5-c]pyrazole This compound was obtained as the second eluting compound from the reaction described in Example 523 as an oil (27 mg. 9%). $^1$H NMR (300 MHz,CDCl$_3$) δ 7.11 (d, 1H, J=2.2 Hz), 6.90 (d, 1H, J=2.2 Hz), 4.28 (m, 1H), 3.76 (s, 3H), 2.81 (g, 2H, J=7.6 Hz), 1.88 (m, 2H), 1.55 (d, 3H, J=7.0 Hz), 1.32 (t, 3H, J=7.5 Hz), 0.92 (t, 3H, J=7.3 Hz). HRMS Calcd. for M+H ($C_{19}H_{25}Cl_3ON_4$): 395.1405. Found: 395.1397.

EXAMPLE 396

Preparation of 4-(n-Butyl)-5-ethyl-3-methyl-1-(2-methyl-4-bromo)phenylimidazo[4,5-c]pyrazole Step A: To 2-methyl-4-bromoaniline (30.0 g, 161 mmol) at 10° C. was added concentrated HCl (400 mL), and to this solution was added sodium nitrite (13.4 g, 193 mmol) in water (125 mL), maintaining an internal temperature of –10° C. during the addition. The reaction was stirred for an hour at 0–5° C., then tin (II) chloride (90.9 g, 403 mmol) in concentrated HCl (395 mL) was added so as to keep the temperature between 5–8° C.; significant foaming occurred during addition. The orange solid was isolated by filtration and dried to give the hydrazine hydrochloride. This compound was dissolved in iN HCl (500 mL) and 3-aminocrotonitrile (13.2 g, 161 mmol) was added and the reaction was heated to reflux for 16 hours. It was cooled to room temperature and the supernatant aqueous phase was decanted and neutralized with 50% NaOH, extracted with ethyl acetate, and the organic solution dried over anhydrous magnesium sulfate and reduced in vacuo to leave the crude product. This was purified by column chromatography (gradient elution of 25–50% ethyl acetate/hexanes) to give the product (11.7 g). The residue from the reaction was dissolved in ethyl acetate and extracted with 1N HCl, and this acidic extract was neutralized with 10% NaOH and extracted with ethyl acetate. The organic phase was dried over anhydrous magnesium sulfate and reduced in vacuo to leave the crude product. This was purified by column chromatography (gradient elution of 25–50% ethyl acetate/hexanes) to recover additional pyrazole as a light yellow solid (total of 13.8 g, 32%), mp 89.5–92° C. $^1$H NMR (300 MHZ,CDCl$_3$) δ 7.47 (d, 1H, J=1.8 Hz), 7.41 (dd, 1H, J=8.5 Hz, J=2.2 Hz), 7.18 (d, 1H, J=8.4 H), 5.42 (s, 1H), 3.49 (bs, 2H), 2.22 (s, 3H), 2.15 (s, 3H). HRMS Calcd. for M+H (C$_{11}$H$_{13}$BrN$_3$): 266.0293. Found: 266.0309. Anal. Calcd. for C$_{11}$H$_{12}$BrN$_3$: C, 49.64; H, 4.54; N, 15.79. Found: C, 49.92; H, 4.53; N, 15.67.

Step B: The compound prepared in Step A (13.8 g, 51.7 mmol) was dissolved in propionic anhydride (33.2 mL, 259 mmol) and was allowed to stir for 16 hours at room temperature. Ice was then added and the reaction stirred for 5 hours, then diethyl ether was added and the phases were separated. The organic phase was washed with saturated sodium chloride, dried over anhydrous magnesium sulfate and reduced in vacua to leave a thick oil. This residue was purified by column chromatography (50% ethyl acetate/hexanes) to give the final product as an off-white solid (13.9 g, 83%), mp 119–121° C. $^1$H NMR (300 MHz,CDCl$_3$) δ 7.51 (s, 1H), 7.43 (dd, 1H, J=8.0 Hz, J=1.8 Hz), 7.12 (d, 1H, J=8.4 Hz)6.91 (bs, 1H), 6.47 (s, 1H), 2.29 (s, 3H), 2.25 (q, 2H, J=7.5 Hz), 2.08 (s, 3H), 1.13m (t, 3H, J=7.5 Hz). HRMS Calcd. for M+H (C$_{14}$H$_{17}$BrN$_3$O): 322.0555. Found: 322.0567. Anal. Calcd. for C$_{14}$H$_{16}$BrN$_3$O: C, 52.19; H, 5.02; N. 13.04. Found: C, 51.94; H, 4.98; N, 12.85.

Step C: The compound prepared in Step B (13.9 g, 43.0 mmol) was suspended in tetrahydrofuran (150 mL). To this suspension was added borane/THF complex (129 mL, 129 mmol), and the reaction refluxed for 16 hours. Excess borane was quenched with 10% NaOH (50 mL) until off-gassing ceased and the reaction was diluted with water and diethyl ether. The layers were separated and the organic phase was washed with saturated sodium chloride, dried over anhydrous magnesium sulfate, and reduced in vacuo to leave the product as a white solid (13.7 g, 103%). mp 116–119° C. $^1$H NMR (300 MHz,CDCl$_3$) δ 7.54 (d, 1H, J=1.8 Hz), 7.49 (dd, 1H, J=8.5 Hz, J=2.2 Hz), 7.14 (d, 1H, J=8.5 Hz), 5.38 (s, 1H), 3.38 (t, 1H, J-5.7 Hz), 3.05 (q, 2H, J=6.7 Hz), 2.37 (s, 3H), 2.03 (s, 3H), 1.53 (m, 2H), 0.88 (t, 3H, J=7.3 Hz). HRMS Calcd. for M+H (C$_{14}$H$_{19}$BrN$_3$): 308.0763. Found: 308.0754.

Step D: The compound prepared in Step C (13.6 g, 44.3 mmol) was suspended in ethanol (110 mL), and one mL of 10% HCl was added. Upon addition of the HCl significant off-gassing occurred, and at the completion of the off-gassing the reaction mixture was homogeneous. Isoamyl nitrite (7.1 mL, 53.2 mmol) was added, and the solution darkened upon addition. The solution was stirred at room temperature for 16 hours, and then a few drops of triethylamine were added to neutralize the HCl. The reaction was reduced to dryness in vacuo and the residue was dissolved in dichloromethane and the insoluble triethylamine hydrochloride was removed by filtration. The reaction was reduced to dryness again and diethyl ether was added, causing a precipitate to form. This solid was isolated by filtration and rinsed with hexanes to leave the product as a purple solid (11.4 g, 76%), mp 120–121.5° C. $^1$H NMR (300 MHz,CDCl$_3$) δ 10.11 (bs, 1H), 7.50 (d, 1H, J=1.8 Hz), 7.45 (dd, 1H, J=8.5 Hz, J=1.8 Hz), 7.21 (d, 1H, J=8.4 Hz), 3.10 (q, 1H, J=7.3 Hz), 2.70 (s, 3H), 2.66 (m, 2H), 2.17 (s, 3H), 1.42 (m, 3H), 0.79 (t, 3H, J=7.3 Hz). HRMS Calcd. for M+H (C$_{14}$H$_{18}$BrN$_4$O): 337.0664. Found: 337.0662. Anal. Calcd. for C$_{14}$H$_{17}$BrN$_4$O: C, 49.86; H, 5.08; N, 16.61. Found: C, 49.90; H, 4.92; N, 16.50.

SteD E: The compound prepared in Step D (11.3 g, 33.5 mmol) was dissolved in anhydrous pyridine (100 mL) and the solution heated to reflux for 16 hours. The solvent was removed in vacuo and the residue purified by column chromatography (50% ethyl acetate/hexanes) to afford the product as a tan solid (7.3 g, 68%) mp 136–138 ° C. $^1$H NMR (300 MHz,CDCl$_3$) δ 8.81 (bs, 1H), 7.44 (m, 1H), 7.35 (m, 2H), 2.83 (q, 2H, J=7.7 Hz), 2.43 (s, 3H), 2.37 (s, 3H), 1.36 (t, 3H, J=7.5 Hz). HRMS Calcd. for M+H (C$_{14}$H$_{16}$BrN$_4$): 319.0559. Found: 319.0555. Anal. Calcd. for C$_{14}$H$_{15}$BrN$_4$: C, 52.68; H, 4.75; N, 17.55. Found: C, 52.53; H, 4.61; N, 17.42.

Step F: The compound prepared in Step E (130 mg, 0.41 mmol) was dissolved in anhydrous dimethylformamide (4 mL) and sodium bis(trimethylsilyl)amide (0.6 M in toluene, 1.7 mL, 1.02 mmol) was added. The solution was heated to 60° C. for one hour, then 1-bromobutane (0.17 mL, 1.63 mmol) was added. The reaction was held at 60° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (15% ethyl acetate/hexanes) to give the final product as an oil (120 mg, 79%). $^1$H NMR (300 MHz,CDCl$_3$) δ 7.43 (m, 1H), 7.36 (m, 2H), 4.01 (t, 2H, J=7.5 Hz), 2.78 (q, 2H, J=7.5 Hz), 2.49 (s, 3H), 2.38 (s, 3H), 1.82 (m, 2H), 1.43 (m, 2H), 1.35 (t, 3H, J-7.5 Hz), 1.00 (t, 3H, J=7.3 Hz). HRMS Calcd. for M+H (C$_{18}$H$_{24}$BrN$_4$): 375.1185. Found: 375.1185. Anal. Calcd. for C$_{18}$H$_{23}$BrN$_4$: C, 57.60; H, 6.19; N, 14.93. Found: C, 57.63; H, 6.00; N, 14.74.

EXAMPLE 397

Preparation of 4-(3,4-Difluorobenzyl)-5-ethyl-3-methyl-1-(2-methyl-4-bromo)phenylimidazo[4,5-c] pyrazole The compound prepared in Step E, Example 396, (130 mg, 0.41 mmol) was dissolved in anhydrous dimethylformamide (4 mL) and sodium bis(trimethylsilyl)amide (0.6 M in toluene, 1.7 mL, 1.02 mmol) was added. The solution was heated to 60° C. for one hour, then α-bromo-3,4-difluorotoluene (0.21 mL, 1.63 mmol) was added. The reaction was held at 60° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (15% ethyl acetate/hexanes) to give the final product as a crystalline solid (125 mg, 69%), mp 127–129° C. $^1$H NMR (300 MHz,CDCl$_3$) δ 7.45 (s, 1H), 7.37 (m, 2H), 7.17 (m, 1H), 6.90 (m, 2H), 5.21 (s, 2H), 2.78 (q, 2H, J=7.5 Hz), 2.9 (s, 3H), 1.57 (s, 3H), 1.32 (t, 3H, J=7./7 Hz). HRMS Calcd. for M+H (C$_{21}$H$_{20}$BrF$_2$N$_4$): 445.0840. Found: 445.0845. Anal. Calcd. for C$_{21}$H$_{19}$BrF2N$_4$: C, 56.64; H, 4.30; N, 12.58. Found: C, 56.46; H, 4.21; N, 12.22.

EXAMPLE 398

Preparation of 5-Ethyl-4-[1-(1-methyl)butane]-3-methyl-1-(2-methyl-4-bromo)phenylimidazo[4,5-c]cpyrazole The compound prepared in Step E, Example 396, (5.38 g, 16.8 mmol) was dissolved in anhydrous dimethylformamide (170 mL) and sodium bis(trimethylsilyl)amide (0.6 M in toluene, 70.2 mL, 42.1 mmol) was added. The solution was heated to 60° C. for one hour, then 2-bromopentane (8.3 mL, 67.2 mmol) was added. The reaction was held at 80° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (gradient elution with 10–50% ethyl acetate/hexanes) to give the final product as an oil (1.68 g, 26%). $^1$H NMR (300 MHz,CDCl$_3$) δ 7.44 (m, 1H), 7.36 (m, 2H), 4.28 (m, 1H), 2.83 (q, 2H, J=7.5 Hz), 2.55 (s, 3H), 2.39 (s, 3H), 1.85 (m, 2H), 1.54 (d, 3H, J=6.6 Hz), 1.34 (t, 3H, J=7.5 Hz), 1.20 (m, 2H), 0.92 (t, 3H, J=7.3 Hz). HRMS Calcd. for M+H (C$_{19}$H$_{26}$BrN$_4$): 389.1341. Found: 389.1341. Anal. Calcd. for C$_{19}$H$_{25}$BrN$_4$: C, 58.61; H, 6.47; N, 14.39. Found: C, 58.88; H, 6.36; N, 14.33.

EXAMPLE 399

Preparation of 4-[1-(1-Ethyl)butane]-5-ethyl-3-methyl-1-(2-methyl-4-bromo)phenylimidazo[4,5-c]pyrazole The compound prepared in Step E, Example 396, (319 mg, 1.0 mol) was dissolved in anhydrous dimethylformamide (10 mL) and sodium bis(trimethylsilyl)amide (0.6 M in toluene, 4.2 mL, 2.5 mmol) was added. The solution was heated to 60° C. for one hour, then 3-bromohexane (660 mg, 4.0 mmol) was added. The reaction was held at 80° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (15% ethyl acetate/hexanes) to give the final product as an oil (37 mg, 9%). $^1$H NMR (300 MHz,CDCl$_3$) δ 7.44 (m, 1H), 7.37 (m, 2H), 4.02 (m, 1H), 2.80 (q, 2H, J=7.5 Hz), 2.52 (s, 3H), 2.38 (s, 3H), 1.83 (m, 4H), 1.35 (t, 3H, J=7.5 Hz), 1.26 (m, 2H), 0.91 (t, 3H, J=7.3 Hz), 0.84 (t, 3H, J=7.5 Hz). HRMS Calcd. for M+H (C$_{20}$H$_{28}$BrN$_4$): 403.1498. Found: 403.1494.

EXAMPLE 400

Preparation of 4-(n-Butyl)-5-ethyl-3-methyl-1-(2-trifluoromethyl-4-bromo)phenylimidazo[4,5-c]pyrazole Step A: To 2-trifluoromethyl-4-bromoaniline (38.4 g, 160 mmol) was added concentrated HCl (400 mL), and to this solution was cooled to 5° C. To this was added sodium nitrite (13.25 g, 192 mmol) in water (125 mL), maintaining an internal temperature of −10° C. with additional cooling. The reaction was stirred for an hour at 0–5° C., then tin (II) chloride (95.0 g, 400 mmol) in concentrated HCl (400 mL) was added so as to keep the temperature between 5–8° C.; significant foaming occurred during addition. The orange solid was recovered by filtration and dried to give the hydrazine hydrochloride (34.9 g, 120 mmol, 75%). This compound was suspended in 1N HCl (500 mL), 3-aminocrotonitrile (9.84 g, 120 mmol) was added and the reaction heated to reflux for 3 hours. It was cooled to room temperature and the supernatant aqueous phase was decanted, filtered to remove a small amount of dark solids, and neutralized with 10% NaOH to give a fine off-white solid. This solid was recovered by filtration and dried to give the product (27.4 g, 71%), mp 117–119° C. $^1$H NMR (300 MHz,CDCl$_3$) δ 7.94 (d, 1H, J=2.2 Hz), 7.80 (dd, 1H, J=8.4 Hz, J=2.2 Hz), 7.33 (d, 1H, J=8.4 Hz), 5.44 (s, 1H), 3.44 (bs, 1H), 2.21 (s, 3H) . HRMS Calcd. for M+H (C$_{11}$H$_{10}$BrF$_3$N$_3$): 320.0011. Found: 320.0005. Anal. Calcd. for C$_{11}$H$_9$BrF$_3$N$_3$: C, 41.27; H, 2.83; N, 13.13. Found: C, 41.33; H, 2.56; N, 12.96.

Step B: The compound prepared in Step A (27.3 g, 85.4 mmol) was dissolved in propionic anhydride (54.8 mL, 427 mmol) and was allowed to stir for 2 hours at room temperature. Ice was then added and the reaction stirred for 16 hours, providing the product as a solid. The product was isolated by filtration and dried to leave an off-white solid (29.8 g, 93%), mp 165.5–167.5° C. $^1$H NMR (300 MHz,CDCl$_3$) δ 7.94 (d, 1H, J=2.2 Hz), 7.80 (dd, 1H, J=8.2 Hz, J=2.0 Hz), 7.33 (d, 1H, J=8.2 Hz), 6.86 (bs, 1H), 6.34 (s, 1H), 2.29 (s, 3H), 2.21 (q, 2H, J=7.5 Hz), 1.08 (t, 3H, J=7.5 Hz). HRMS Calcd. for M+H (C$_{14}$H$_{14}$BrF$_3$ON$_3$) : 376.0273. Found: 376.0267. Anal. Calcd. for C$_{14}$H$_{13}$BrF$_3$ON$_3$: C, 44.70; H, 3.48; N, 11.17. Found: C, 44.47; H, 3.27; N, 11.02.

Step C: The compound prepared in Step B (29.8 g, 79.1 mmol) was suspended in anhydrous tetrahydrofuran (220 mL). To this suspension was added borane/THF complex (237 mL, 237 mmol), and the reaction refluxed for 16 hours. Excess borane was quenched with 10% NaOH (100 mL) until off-gassing ceased, and the reaction was filtered through Celite. Diethyl ether was added and the layers were separated, the organic phase was washed with saturated sodium chloride, dried over anhydrous magnesium sulfate, and reduced in vacuo to leave the product as a white solid (28.4 g, 99%). $^1$H NMR (300 MHz,CDCl$_3$) δ 7.94 (d, 1H, J=2.2 Hz), 7.79 (dd, 1H, J=8.4 Hz, J=2.2 Hz), 5.31 (s, 1H), 3.10 (bs, 1H), 3.01 (m, 2H), 2.23 (s, 3H), 1.54 (m, 2H), 0.90 (t, 3H, J=7.5 Hz). HRMS Calcd. for M+H (C$_{14}$H$_{16}$BrF$_3$N$_3$): 362.0480. Found: 362.0470.

Step D: The compound prepared in Step C (28.3 g, 78.1 mmol) was suspended in ethanol (200 mL), and one mL of 10% HCl was added. Upon addition of the HCl significant off-gassing occurred, and at the completion of the off-gassing the reaction mixture was homogeneous. Isoamyl nitrite (12.6 mL, 93.8 mmol) was then added, and the solution darkened upon addition. The solution was stirred at room temperature for 16 hours, and then a few drops of triethylamine were added to neutralize the HCl. The reaction was reduced to dryness in vacuo and the residue was dissolved in dichloromethane and the insoluble triethylamine hydrochloride was removed by filtration. The reaction was again reduced to dryness and hexanes was added, causing a red precipitate to form. This solid was isolated by filtration and rinsed with hexanes to leave the product as a red solid (18.2 g, 60%). $^1$H NMR (300 MHz,CDCl$_3$) δ 10.34 (bs, 1H), 7.97 (d, 1H, J=1.8 Hz), 7.85 (dd, 1H, J=8.5 Hz, J=2.2 Hz), 7.38 (d, 8.5 Hz), 2.70 (s, 3H), 2.65 (m, 2H), 1.44 (m, 2H), 0.82 (t, 3H, J=7.3 Hz). HRMS Calcd. for M+H ($C_{14}H_{15}BrON_4$): 391.0382. Found: 391.0380. Anal. Calcd. for $C_{14}H_{14}BrON_4$: C, 42.98; H, 3.62; N, 14.32. Found: C, 3.22; H, ; N, 14.09.

Step E: The compound prepared in Step D (18.1 g, 46.2 mmol) was dissolved in anhydrous pyridine (200 mL) and the solution heated to reflux for 16 hours. The solvent was removed in vacuo and the residue purified by column chromatography (gradient elution with 25–50% ethyl acetate/hexanes) to afford the product as a tan solid (13.1 g, 76%) mp 158–160.5° C. $^1$H NMR (300 MHz,CDCl$_3$) δ 8.65 (bs, 1H), 7.92 (d, 1H, J=2.2 H), 7.73 (dd, 1H, J=8.8 Hz, J=2.2 Hz), 7.52 (d, 1H, J=8.4 Hz), 2.85 (q, 2H, J=7.5 Hz), 2.43 (s, 3H), 1.38 (t, 3H, J=7.7 Hz). HRMS Calcd. for M+H ($C_{14}H_{13}BrN_4$): 373.0276. Found: 373.0281. Anal. Calcd. for $C_{14}H_{12}BrN_4$ C, 45.06; H, 3.24; N, 15.01. Found: C, 44.70; H, 3.00; N, 14.59.

Step F: The compound prepared in Step E (153 mg, 0.41 mmol) was dissolved in anhydrous dimethylformamide (4 mL) and sodium bis(trimethylsilyl)amide (0.6 M in toluene, 1.7 mL, 1.02 mmol) was added. The solution was heated to 60° C. for one hour, then 1-bromobutane (0.17 mL, 1.63 mmol) was added. The reaction was held at 60° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (gradient elution with 15–25% ethyl acetate/hexanes) to give the final product as a crystalline solid (68 mg, 39%), mp 78–80° C. $^1$H NMR (300 MHz,CDCl$_3$) δ 7.91 (d, 1H, J=2.2 Hz), 7.72 (dd, 1H, J=8.5 Hz, J=2.2 Hz), 7.55 (d, 1H, J=8.4 Hz), 4.01 (t, 2H, J=7.3 Hz), 2.78 (q, 2H, J=7.5 Hz), 2.48 (s, 3H), 1.83 (m, 2H), 1.42 (m, 2H), 1.35 (t, 3H, J=7.7 Hz), 1.00 (t, 3H, J=7.3 Hz). HRMS Calcd. for M+H ($C_{18}H_{21}BrF_3N_4$): 429.0902. Found: 429.0894. Anal. Calcd. for $C_{18}H_{20}BrF_3N_4$: C, 50.36; H, 4.71; N, 13.05. Found: C, 50.70; H, 4.58; N, 12.91.

EXAMPLE 401

Preparation of 4-(3,4-Difluorobenzyl)-5-ethyl-3-methyl-1-(2-trifluoromethyl-4-bromo)phenylimidazo [4,5-c]pyrazole The compound prepared in Step E, Example 400, (153 mg, 0.41 mmol) was dissolved in anhydrous dimethylformamide (4 mL) and sodium bis(trimethylsilyl)amide (0.6 M in toluene, 1.7 mL, 1.02 mmol) was added. The solution was heated to 60° C. for one hour, then α-bromo-3,4-difluorotoluene (0.21 mL, 1.63 mmol) was added. The reaction was held at 60° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (25% ethyl acetate/hexanes) to give the final product as a crystalline solid (74 mg, 36%), mp 105–107° C. $^1$H NMR (300 MHz,CDCl$_3$) δ 7.93 (d, 1H, J=2.2 Hz), 7.75 (dd, 1H, J=8.8 Hz, J=2.2 Hz), 7.57 (d, 1H, J=8.4 Hz), 7.18 (m, 1H), 6.90 (m, 2H), 5.21 (s, 2H), 2.77 (q, 2H, J=7.5 Hz), 2.18 (s, 3H), 1.32 (t, 3H, J=7.7 Hz). HRMS Calcd. for M+H ($C_{21}H_{17}BrF_5N_4$): 499.0557. Found: 499.0558. Anal. Calcd. for $C_{21}H_{16}BrF_5N_4$: C, 50.52; H, 3.23; N, 11.22. Found: C, 50.98; H, 3.19; N, 11.01.

EXAMPLE 402

Preparation of 5-Ethyl-4-[1-(1-methyl)butane]-3-methyl-1-(2-trifluoromethyl-4-bromo)phenylimidazo [4,5-c]pyrazole The compound prepared in Step E, Example 400, (3.4 g, 9.16 mmol) was dissolved in anhydrous dimethylformamide (100 mL) and sodium bis(trimethylsilyl)amide (0.6 M in toluene, 38.2 mL, 22.9 mmol) was added. The solution was heated to 60° C. for one hour, then 2-bromopentane (4.5 mL, 36.6 mmol) was added. The reaction was held at 80° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (gradient elution with 10–20% ethyl acetate/hexanes) to give the final product as a crystalline solid (829 mg, 20%), mp 51–53° C. $^1$H NMR (300 MHz,CDCl$_3$) δ 7.92 (d, 1H, J=2.2 Hz), 7.73 (dd, 1H, J=8.4 Hz, J=2.2 Hz), 7.58 (d, 1H, J=8.4 Hz), 4.29 (m, 1H), 2.81 (q, 2H, J=7.5 Hz), 2.53 (s, 3H), 1.85 (m, 2H), 1.54 (d, 3H, J=6.6 Hz0<1.34 (t, 3H, J=7.5 Hz), 0.92 (t, 3H, J=7.3 Hz). HRMS Calcd. for M+H ($C_{19}H_{23}BrF_3N_4$): 443.1059. Found: 443.1064. Anal. Calcd. for $C_{19}H_{22}BrF3N_4$: C, 51.48; H, 5.00; N, 12.64. Found: C, 51.84; H, 4.99; N, 12.56.

EXAMPLE 403

Preparation of 5-Ethyl-4-[1-(1-ethyl)butane]-3-methyl-1-(2-trifluoromethyl-4-bromo)phenylimidazo [4,5-c]pyrazole The compound prepared in Step E, Example 400, (373 mg, 1.0 mmol) was dissolved in anhydrous dimethylformamide (10 mL) and sodium bis(trimethylsilyl)amide (0.6 M in toluene, 4.2 mL, 2.5 mmol) was added. The solution was heated to 60° C. for one hour, then 3-bromohexane (660. mg, 4.0 mmol) was added. The reaction was held at 80° C. for 16 hours, cooled to room temperature, and diluted with water and diethyl ether. The layers were separated and the organic phase washed with water, dried over anhydrous magnesium sulfate, and reduced in vacuo. The residue was purified by column chromatography (15% ethyl acetate/ hexanes) to give the final product as an oil (50 mg, 11%). $^1$H NMR (300 MHz,CDCl$_3$) δ 7.91 (d, 1H, J=2.2 Hz), 7.73 (dd, 1H, J=8.5 Hz, J=2.2 Hz), 7.61 (d, 1H, J=8.8 Hz), 4.00 (m, 1H), 2.80 (q, 2H, J=7.5 Hz), 2.51 (s, 3H), 1.83 (m, 4H), 1.35 (t, 3H, J=7.5 Hz), 1.23 (m, 2H), 0.91 (t, 3H, J=7.3 Hz), 0.83 (t, 3H, J=7.5 Hz). HRMS Calcd. for M+H (C$_{20}$H$_{25}$BrF$_3$N$_4$): 457.1215. Found: 457.1223.

EXAMPLE 408

Preparation of 5-Ethyl-4-[1-(1-methyl)butane]-3-methyl-1-(2-methyl-4-acetyl)phenylimidazo[4,5-c]pyrazole The compound prepared in Example 396 (492 mg, 1.26 mmol) was dissolved in anhydrous toluene (5 mL) and dichlorobis (triphenylphosphine)palladium(II) (18 mg, 0.025 mmol) was added, followed by tributyl(1-ethoxyvinyl)tin 548 mg, 1.52 mmol), and the solution was heated to reflux for 2.5 hours. The reaction was cooled to room temperature and quenched with 1N HCl (10 mL) and diethyl ether. After stirring for 30 minutes the layers were separated and the organic phase was washed with saturated aqueous sodium chloride, filtered through Celite, dried over anhydrous magnesium sulfate and reduced to dryness in vacuo. The crude product was purified by column chromatography (gradient elution with 10–20% ethyl acetate/hexanes) to give the final product as a yellow oil (225 mg, 51%). $^1$H NMR (300 MHz,CDCl$_3$) δ 7.91 (m, 1H), 7.85 (dd, 1H, J=8.4 Hz, J=1.8 Hz), 7.68 (d, 1H, J=8.1 Hz), 4.30 (m, 1H), 2.83 (q, 2H, J=7.5 Hz), 2.61 (s, 3H), 2.57 (s, 3H), 2.56 (s, 3H), 1.86 (m, 2H), 1.54 (d, 3H, J=6.6 Hz), 1.35 (t, 3H, J=7.5 Hz), 1.21 (t, 3H, J=7.1 Hz). HRMS Calcd. for M+H (C$_{21}$H$_{29}$ON$_4$): 353.2341. Found: 353.2344. Anal. Calcd. for C$_{21}$H$_{28}$N$_4$O: C, 71.56; H, 8.02; N, 15.90. Found: C, 71.39; H, 7.97; N, 15.55.

The Examples in Table 3 may be prepared as amply exemplified above for the preparation of Examples 325–334, 353–357, 396–403, and 408.

TABLE 3

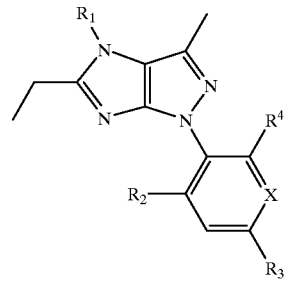

| Ex. | R$_1$ | R$_2$ | R$_3$ | R$_4$ | X | mp °C. |
|---|---|---|---|---|---|---|
| 262 | CH$_2$C(CH$_2$CH$_3$)$_2$ | Me | Me | Me | C | Oil, MS |
| 263 | benzyl | Me | Me | Me | C | 97–98 |
| 264 | n-butyl | Me | Me | Me | C | 81–83 |
| 265 | 2-phenylbenzyl | Me | Me | Me | C | |
| 266 | 4-phenylbenzyl | Me | Me | Me | C | |
| 267 | CH$_2$CH$_2$OCH$_2$CH$_3$ | Me | Me | Me | C | |
| 268 | CH$_2$C(CH$_2$CH$_3$)$_2$ | Me | Me | Me | N | |
| 269 | benzyl | Me | Me | Me | N | |
| 270 | n-butyl | Me | Me | Me | N | |
| 271 | 4-fluorobenzyl | Br | iPr | H | C | 107–108 |
| 272 | 2-phenylbenzyl | Br | iPr | H | C | Oil, MS |
| 273 | 4-phenylbenzyl | Br | iPr | H | C | 135–136 |
| 274 | n-pentyl | Br | iPr | H | C | 132–135 |
| 275 | benzyl | Br | iPr | H | C | Oil, MS |
| 276 | n-butyl | Br | iPr | H | C | 76–69 |
| 277 | CH$_2$cPr | Br | iPr | H | C | Oil, MS |
| 278 | CH$_2$CH(Et)$_2$ | Br | iPr | H | C | Oil, MS |
| 279 | CH(Et)$_2$ | Br | iPr | H | C | Oil, MS |
| 280 | CH$_2$CH$_2$CH(Me)$_2$ | Br | iPr | H | C | Oil, MS |
| 281 | CH(Et)CH$_2$CH$_2$CH$_3$ | Br | iPr | H | C | Oil, MS |
| 282 | CH(Me)CH$_2$CH$_2$CH$_3$ | Br | iPr | H | C | Oil, MS |
| 283 | CH$_2$CH$_2$OCH$_2$CH$_3$ | Br | iPr | H | C | |
| 284 | CH$_2$CH$_2$SCH$_2$CH$_3$ | Br | iPr | H | C | |
| 285 | 4-picolyl | Br | iPr | H | C | |
| 286 | CH(cPr)$_2$ | Br | iPr | H | C | |
| 287 | CH(ethyl)n-butyl | Br | iPr | H | C | |
| 288 | CH(CH$_2$OMe)$_2$ | Br | iPr | H | C | |
| 289 | benzyl | Br | OMe | OMe | C | |
| 290 | n-butyl | Br | OMe | OMe | C | |
| 291 | 4-fluorobenzyl | Br | OMe | OMe | C | |
| 292 | 2-phenylbenzyl | Br | OMe | OMe | C | |
| 293 | 4-phenylbenzyl | Br | OMe | OMe | C | |
| 294 | n-pentyl | Br | OMe | OMe | C | |
| 295 | CH(cPr)$_2$ | Br | OMe | OMe | C | |
| 296 | benzyl | Br | Cl | Cl | C | 125–127 |
| 297 | n-butyl | Br | Cl | Cl | C | 111–112 |

TABLE 3-continued

| Ex. | R₁ | R₂ | R₃ | R₄ | X | mp °C. |
|---|---|---|---|---|---|---|
| 298 | CH₂cPr | Br | Cl | Cl | C | 128–129 |
| 299 | CH₂CH(ethyl)₂ | Br | Cl | Cl | C | 127–128 |
| 300 | CH₂CH₂CH(CH₃)₂ | Br | Cl | Cl | C | 88–89 |
| 301 | 4-fluorobenzyl | Br | Cl | Cl | C | 110–113 |
| 302 | 4-phenylbenzyl | Br | Cl | Cl | C | 131–134 |
| 303 | n-pentyl | Br | Cl | Cl | C | 135–136 |
| 304 | CH(Et)CH₂CH₂CH₃ | Br | Cl | Cl | C | 116–118 |
| 305 | CH(Me)CH₂CH₂CH₃ | Br | Cl | Cl | C | Oil, MS |
| 306 | benzyl | Br | Cl | Br | C | 117–124 |
| 307 | n-butyl | Br | Cl | Br | C | 112–113 |
| 308 | CH₂cPr | Br | Cl | Br | C | 122–123 |
| 309 | CH₂CH(CH₂CH₃)₂ | Br | Cl | Br | C | 124–126 |
| 310 | CH₂CH₂CH(CH₃)₂ | Br | Cl | Br | C | 67–69 |
| 311 | 4-fluorobenzyl | Br | Cl | Br | C | Oil, MS |
| 312 | 4-phenylbenzyl | Br | Cl | Br | C | 124–125 |
| 313 | n-pentyl | Br | Cl | Br | C | 124–125 |
| 314 | n-butyl | Cl | Br | Cl | C | 111–112 |
| 315 | CH₂CH₂CH(CH₃)₂ | Cl | Br | Cl | C | 115–116 |
| 316 | CH₂CH(CH₂CH₃)₂ | Cl | Br | Cl | C | 142–144 |
| 317 | benzyl | Cl | Br | Cl | C | 136–137 |
| 318 | 3,4-difluorobenzyl | Cl | Br | Cl | C | 136–138 |
| 319 | CH₂-(2-tetrahydropyran) | Cl | Br | Cl | C | 136–138 |
| 320 | CH(Et)CH₂CH₂CH₃ | Cl | Br | Cl | C | 132–133 |
| 321 | CH(CH₃)CH₂CH(CH₃)₂ | Cl | Br | Cl | C | Oil, MS |
| 322 | CH(CH₃)CH₂CH₂CH₃ | Cl | Br | Cl | C | 95–98 |
| 323 | n-butyl | Cl | CN | H | C | 163–165 |
| 324 | n-butyl | Cl | CN | CN | C | 151–153 |
| 325 | n-butyl | Cl | Br | H | C | Oil, MS |
| 326 | 3,4-difluorobenzyl | Cl | Br | H | C | 114–116 |
| 327 | CH(Et)CH₂CH₂CH₃ | Cl | Br | H | C | Oil, MS |
| 328 | CH(CH₃)CH₂CH₂CH₃ | Cl | Br | H | C | Oil, MS |
| 329 | n-butyl | Cl | Me | H | C | Oil, MS |
| 330 | CH(CH₃)CH₂CH₂CH₃ | Cl | Me | H | C | Oil, MS |
| 331 | n-butyl | Cl | CF₃ | H | C | Oil, MS |
| 332 | 3,4-difluorobenzyl | Cl | CF₃ | H | C | 108–110 |
| 333 | CH(Et)CH₂CH₂CH₃ | Cl | CF₃ | H | C | Oil, MS |
| 334 | CH(CH₃)CH₂CH₂CH₃ | Cl | CF₃ | H | C | Oil, MS |
| 335 | CH(Et)CH₂CH₂CH₃ | Cl | Cl | H | C | Oil, MS |
| 336 | CH(CH₃)CH₂CH₂CH₃ | Cl | Cl | H | C | 105–107 |
| 337 | n-butyl | Cl | Cl | H | C | Oil, MS |
| 338 | CH₂CH₂CH(CH₃)₂ | Cl | Cl | H | C | Oil, MS |
| 339 | CH₂CH(CH₂CH₃)₂ | Cl | Cl | H | C | Oil, MS |
| 340 | benzyl | Cl | Cl | H | C | Oil, MS |
| 341 | 3,4-difluorobenzyl | Cl | Cl | H | C | 124–125 |
| 342 | CH₂-(2-tetrahydropyran) | Cl | Cl | H | C | 100–101 |
| 343 | CH(CH3)CH2CH(CH3)2 | Cl | Cl | H | C | Oil, MS |
| 344 | n-butyl | Et | Br | Et | C | 54–55 |
| 345 | CH₂CH₂CH(CH₃)₂ | Et | Br | Et | C | Oil, MS |
| 346 | CH₂CH(CH₂CH₃)₂ | Et | Br | Et | C | Oil, MS |
| 347 | benzyl | Et | Br | Et | C | Oil, MS |
| 348 | 3,4-difluorobenzyl | Et | Br | Et | C | Oil, MS |
| 349 | CH₂-(2-tetrahydropyran) | Et | Br | Et | C | Oil, MS |
| 350 | CH(Et)CH₂CH₂CH₃ | Et | Br | Et | C | 70–72 |
| 351 | CH(CH₃)CH₂CH(CH₃)₂ | Et | Br | Et | C | 91–93 |
| 352 | CH(CH₃)CH₂CH₂CH₃ | Et | Br | Et | C | 82–84 |
| 353 | n-butyl | Cl | OMe | H | C | Oil, MS |
| 354 | n-butyl | OMe | OMe | H | C | Oil, MS |
| 355 | n-butyl | OMe | Br | H | C | Oil, MS |
| 356 | CH(CH₃)CH₂CH₂CH₃ | Cl | OMe | Cl | C | Oil, MS |
| 357 | CH(CH₃)CH₂CH₂CH₃ | OMe | Cl | Cl | C | Oil, MS |
| 358 | CH(CH₃)CH₂CH₂CH₃ | Br | OMe | H | C | |
| 359 | CH(CH₃)CH₂CH₂CH₃ | Br | OMe | Cl | C | |

TABLE 3-continued

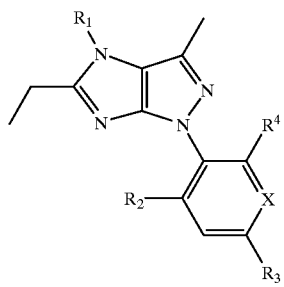

| Ex. | $R_1$ | $R_2$ | $R_3$ | $R_4$ | X | mp °C. |
|---|---|---|---|---|---|---|
| 360 | $CH(CH_3)CH_2CH_2CH_3$ | Br | OMe | OMe | C | |
| 361 | $CH(CH_3)CH_2CH_2CH_3$ | Me | OMe | H | C | |
| 362 | $CH(CH_3)CH_2CH_2CH_3$ | Me | OMe | Cl | C | |
| 363 | $CH(CH_3)CH_2CH_2CH_3$ | Cl | OMe | OMe | N | |
| 364 | benzyl | H | OMe | OMe | N | |
| 365 | n-butyl | H | OMe | OMe | N | |
| 366 | $CH_2cPr$ | H | OMe | OMe | N | |
| 367 | $CH_2CH(CH_2CH_3)_2$ | H | OMe | OMe | N | |
| 368 | $CH(CH_3)CH_2CH_2CH_3$ | H | OMe | OMe | N | |
| 369 | 3,4-difluorobenzyl | H | OMe | OMe | N | |
| 370 | $CH_2cPr$ | Me | Me | Me | N | |
| 371 | $CH_2CH(CH_2CH_3)_2$ | Me | Me | Me | N | |
| 372 | $CH(CH_3)CH_2CH_2CH_3$ | Me | Me | Me | N | |
| 373 | 3,4-difluorobenzyl | Me | Me | Me | N | |
| 374 | $CH_2cPr$ | Me | Me | H | N | |
| 375 | $CH_2CH(CH_2CH_3)_2$ | Me | Me | H | N | |
| 376 | $CH(CH_3)CH_2CH_2CH_3$ | Me | $NMe_2$ | H | N | |
| 377 | 3,4-difluorobenzyl | Me | $NMe_2$ | H | N | |
| 378 | n-pentyl | Et | Me | Et | C | |
| 379 | benzyl | Et | Me | Et | C | |
| 380 | n-pentyl | H | Me | Me | N | |
| 381 | benzyl | H | Me | Me | N | |
| 382 | n-pentyl | H | $NMe_2$ | Me | N | |
| 383 | benzyl | H | $NMe_2$ | Me | N | |
| 384 | n-pentyl | $CF_3$ | $NMe_2$ | H | C | |
| 385 | benzyl | $CF_3$ | $NMe_2$ | H | C | |
| 386 | n-pentyl | Me | $NMe_2$ | H | C | |
| 387 | benzyl | Me | $NMe_2$ | H | C | |
| 388 | n-pentyl | Br | $NMe_2$ | H | C | |
| 389 | benzyl | Br | $NMe_2$ | H | C | |
| 390 | n-pentyl | Br | iPr | OMe | C | |
| 391 | benzyl | Br | iPr | OMe | C | |
| 392 | n-pentyl | Br | SMe | H | C | |
| 393 | benzyl | Br | SMe | H | C | |
| 394 | n-pentyl | Br | SOMe | H | C | |
| 395 | benzyl | Br | $SO_2Me$ | H | C | |
| 396 | n-butyl | Me | Br | H | C | Oil, MS |
| 397 | 3,4-difluorobenzyl | Me | Br | H | C | 127–129 |
| 398 | $CH(CH_3)CH_2CH_2CH_3$ | Me | Br | H | C | Oil, MS |
| 399 | $CH(Et)CH_2CH_2CH_3$ | Me | Br | H | C | Oil, MS |
| 400 | n-butyl | $CF_3$ | Br | H | C | 78–80 |
| 401 | 3,4-difluorobenzyl | $CF_3$ | Br | H | C | 105–107 |
| 402 | $CH(CH_3)CH_2CH_2CH_3$ | $CF_3$ | Br | H | C | 51–53 |
| 403 | $CH(Et)CH_2CH_2CH_3$ | $CF_3$ | Br | H | C | Oil, MS |
| 404 | n-butyl | Br | Me | F | C | |
| 405 | 3,4-difluorobenzyl | Br | Me | H | C | |
| 406 | $CH(CH_3)CH_2CH_2CH_3$ | OMe | Me | H | C | |
| 407 | $CH(Et)CH_2CH_2CH_3$ | COMe | Me | H | C | |
| 408 | n-butyl | Me | COMe | H | C | |
| 409 | 3,4-difluorobenzyl | Me | COMe | Me | C | |
| 410 | $CH(CH_3)CH_2CH_2CH_3$ | Cl | COMe | H | C | |
| 411 | $CH(Et)CH_2CH_2CH_3$ | Cl | COMe | Cl | C | |
| 412 | n-butyl | Cl | Ph | H | C | |
| 413 | 3,4-difluorobenzyl | Cl | Ph | OMe | C | |
| 414 | $CH(CH_3)CH_2CH_2CH_3$ | Cl | $CO_2Me$ | Cl | C | |
| 415 | $CH(Et)CH_2CH_2CH_3$ | Cl | OCOMe | Cl | C | |

Examples 416–452 given in TABLE 4 may be prepared from compounds of formula $R^3(NH_2)C=C(CN)H$ where $R^3$ is Me and the appropriate hydrazine of formula $R^4NHNH_2$, where $R^4$ corresponds to the substitutions exemplified in Table 4 to give initially compounds of formula (III). Conversion to compounds of formula (I) may then follow the preparation detailed for Examples 38 and 164.

TABLE 4

[Structure with R¹ on N, ethyl, methyl, pyrazole-imidazole core, and phenyl with R², R³, R⁴, R⁵ substituents]

| Ex. | R¹ | R² | R³ | R⁴ | R⁵ | mp °C. |
|---|---|---|---|---|---|---|
| 416 | n-butyl | Cl | H | Cl | H | Oil, MS |
| 417 | $CH_2CH_2CH(CH_3)_2$ | Cl | H | Cl | H | Oil, MS |
| 418 | $CH_2CH(CH_2CH_3)_2$ | Cl | H | Cl | H | Oil, MS |
| 419 | benzyl | Cl | H | Cl | H | 113–114 |
| 420 | 3,4-difluorobenzyl | Cl | H | Cl | H | Oil, MS |
| 421 | $CH_2$-(2-tetrahydropyran) | Cl | H | Cl | H | 125–126 |
| 422 | $CH(CH_2CH_3)(CH_2CH_2CH_3)$ | Cl | H | Cl | H | Oil, MS |
| 423 | $CH(CH_3)CH_2CH(CH_3)_2$ | Cl | H | Cl | H | Oil, MS |
| 424 | $CH(CH_3)CH_2CH_2CH_3$ | Cl | H | Cl | H | Oil, MS |
| 425 | n-butyl | H | Cl | Cl | Cl | Oil, MS |
| 426 | $CH_2CH_2CH(CH_3)_2$ | H | Cl | Cl | Cl | Oil, MS |
| 427 | $CH_2CH(CH_2CH_3)_2$ | H | Cl | Cl | Cl | Oil, MS |
| 428 | benzyl | H | Cl | Cl | Cl | Oil, MS |
| 429 | 3,4-difluorobenzyl | H | Cl | Cl | Cl | Oil, MS |
| 430 | $CH_2$-(2-tetrahydropyran) | H | Cl | Cl | Cl | Oil, MS |
| 431 | n-butyl | Cl | Cl | Cl | H | Oil, MS |
| 432 | $CH_2CH_2CH(CH_3)_2$ | Cl | Cl | Cl | H | Oil, MS |
| 433 | $CH_2CH(CH_2CH_3)_2$ | Cl | Cl | Cl | H | Oil, MS |
| 434 | benzyl | Cl | Cl | Cl | H | 153–155 |
| 435 | 3,4-difluorobenzyl | Cl | Cl | Cl | H | Oil, MS |
| 436 | $CH_2$-(2-tetrahydropyran) | Cl | Cl | Cl | H | Oil, MS |
| 437 | $CH(CH_2CH_3)(CH_2CH_2CH_3)$ | Cl | Cl | Cl | H | Oil, MS |
| 438 | $CH(CH_3)CH_2CH(CH_3)_2$ | Cl | Cl | Cl | H | Oil, MS |
| 439 | $CH(CH_3)CH_2CH_2CH_3$ | Cl | Cl | Cl | H | Oil, MS |
| 440 | benzyl | Br | Me | F | H | |
| 441 | $CH(CH_3)CH_2CH(CH_3)_2$ | Br | Me | F | H | |
| 442 | $CH(CH_3)CH_2CH_2CH_3$ | Me | Br | F | H | |
| 443 | benzyl | Me | Me | F | Me | |
| 444 | $CH(CH_3)CH_2CH(CH_3)_2$ | Cl | Me | F | Me | |
| 445 | $CH(CH_3)CH_2CH_2CH_3$ | Cl | Cl | F | H | |
| 446 | benzyl | Me | Br | Cl | H | |
| 447 | $CH(CH_3)CH_2CH(CH_3)_2$ | Me | Me | Me | H | |
| 448 | $CH(CH_3)CH_2CH_2CH_3$ | Cl | Me | Me | H | |
| 449 | benzyl | Cl | Br | Me | H | |
| 450 | $CH(CH_3)CH_2CH(CH_3)_2$ | Me | Cl | Me | H | |
| 451 | $CH(CH_3)CH_2CH_2CH_3$ | H | OMe | Me | Me | |
| 452 | benzyl | Cl | $NO_2$ | Cl | H | |

Examples 453–471 given in TABLE 5 may be preferably prepared by treatment of compounds of formula (I, R³ is OH or SH) with a base such as, but not limited to, potassium hydroxide in a solvent such as acetone or other inert solvent with a reagent R¹⁰-X where X is a leaving group (vide supra). These product compounds arise via the tautomeric nature of compounds of formula (I) where R³ is OH or SH.

TABLE 5

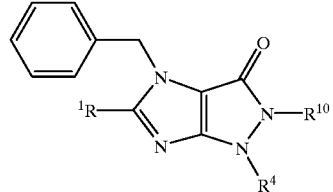

| Example | R¹ | R¹⁰ | R³ | mp °C. |
|---|---|---|---|---|
| 453 | Me | H | 2,4,6-trimethylphenyl | |
| 454 | Me | Me | 2,4,6-trichlorophenyl | |
| 455 | Me | $CH_2cPr$ | 4-chloro-2,6-dibromophenyl | |
| 456 | Me | COPh | 2-bromo-4,6-dichlorophenyl | |
| 457 | Et | H | 2,4,6-trimethylphenyl | |
| 458 | Et | Me | 2,4,6-trichlorophenyl | |
| 459 | Et | Et | 2,4,6-trichlorophenyl | |
| 460 | Et | i-Pr | 2,4,6-trichlorophenyl | |
| 461 | Et | c-Pr | 2,4,6-trichlorophenyl | |
| 462 | Et | n-Pr | 2,4,6-trichlorophenyl | |
| 463 | Et | $CH_2cPr$ | 2,4,6-trichlorophenyl | |
| 464 | Et | c-pentyl | 2,4,6-trichlorophenyl | |
| 465 | Et | $CH_2cPr$ | 4-chloro-2,6-dibromophenyl | |
| 466 | Et | COPh | 2-bromo-4,6-dichlorophenyl | |
| 467 | Et | Me | 2,4,6-trimethylphenyl | |
| 468 | Et | Me | 4-chloro-2,6-dibromophenyl | |
| 469 | Et | Me | 2-bromo-4,6-dichlorophenyl | |
| 470 | Ph | Me | 2,4,6-trimethylphenyl | |
| 471 | Ph | $CH_2cPr$ | 2,4,6-trichlorophenyl | |

UTILITY

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 µg/ml to be used in the assay.

Binding assays are performed in 96 well plates; each well having a 300 µl capacity. To each well is added 50 µl of test drug dilutions (final concentration of drugs range from $10^{-10}$–$10^{-5}$ M), 100 µl of $^{125}$I-ovine-CRF ($^{125}$I-o-CRF) (final concentration 150 pM) and 150 µl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 370° C. for 10 min in 200 ml of buffer containing 100 mM Tris-HCl (pH 7.4 at 370° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6m}$) and 0.8 mg original wet weight tissue (approximately 40–60 mg protein). Reactions are initiated by the addition of 1 mM ATP/[$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering treating psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formulae (I) or (II):

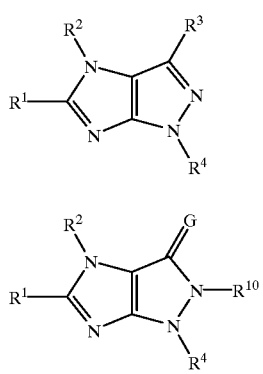

isomers thereof, stereoisomeric forms thereof, or mixtures of stereoisomeric forms thereof, and pharmaceutically acceptable salt forms thereof, wherein: G is O or S;

$R^1$ is selected from H, $C_1$–$C_6$ alkyl, $C_2$–$C_6$ alkenyl, $C_2$–$C_6$ alkynyl, $C_1$–$C_6$ haloalkyl $C_3$–$C_6$ cycloalkyl, $C_4$–$C_8$ cycloalkylalkyl, C1–C6 alkoxy, aryl, heteroaryl or heterocyclyl;

$R^2$ is $C_1$–$C_{10}$ alkyl, $C_3$–$C_{10}$ alkenyl, $C_3$–$C_{10}$ alkynyl, $C_3$–$C_8$ cycloalkyl, $C_4$–$C_{12}$ cycloalkylalkyl, where each group can be optionally substituted with 1 to 3 substituents independently selected at each occurrence from $C_1$–$C_6$ alkyl, $C_3$–$C_{10}$ alkenyl, $C_3$–$C_{10}$ alkynyl, $C_3$–$C_6$ cycloalkyl, aryl, heteroaryl, heterocyclyl, halogen, cyano, $NR^6R^7$, $OR^7$, thiol, $S(O)_nR^9$, $COR^7$, $CO_2R^7$, $OC(O)R^9$, $NR^8COR^7$, $NR^8CONR^6R^7$, $NR^8CO_2R^9$, $CONR^6R^7$;

or $S(O)_nR^9$, $COR^7$, $CO_2R^7$, $CONR^6R^7$;

or $C_1$–$C_4$ haloalkyl or aryl or aryl($C_1$–$C_4$ alkyl), heteroaryl or heteroaryl ($C_1$–$C_4$ alkyl), heterocyclyl, or heterocyclyl($C_1$–$C_4$ alkyl), wherein $C_1$–$C_4$ alkyl in aryl($C_1$–$C_4$ alkyl), heteroaryl($C_1$–$C_4$ alkyl) or heterocyclyl($C_1$–$C_4$ alkyl) is optionally substituted with substituents selected from $C_1$–$C_8$ alkyl, $COR^7$, $CO_2R^7$, $S(O)_nR^9$, cyano and aryl;

n is independently at each occurrence 0, 1, or 2;

$R^3$ is H, $C_1$–$C_6$ alkyl, $C_2$–$C_6$ alkenyl, $C_2$–$C_6$ alkynyl, $C_1$–$C_6$ haloalkyl, $C_3$–$C_6$ cycloalkyl, $C_2$–$C_{10}$ alkoxyalkyl, $C_1$–$C_6$ hydroxyalkyl, cyano, $OR^6$, thiol, $S(O)_nR^9$, $NR^6R^7$, aryl, or heteroaryl;

$R^4$ is phenyl optionally substituted with 1 to 4 $R^5$ groups;

$R^5$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, where $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl are optionally substituted with 1–3 substituents independently selected at each occurrence from $C_1$–$C_4$ alkyl, nitro, halogen, cyano, $NR^6R^7$, $NR^8COR^7$, $NR^8CO_2R^9$, $COR^7$, $OR^7$, $CONR^6R^7$, $NR^8CONR^6R^7$, $CO_2R^7$, thiol, or $S(O)_nR^9$;

or nitro, halogen, cyano, $C_1$–$C_4$ haloalkyl, $NR^6R^7$, $NR^8COR^7$, $NR^8CO_2R^9$, $COR^7$, $OR^7$, $CONR^6R^7$, $NR^8CONR^6R^7$, $CO_2R^7$, thiol, or $S(O)_nR^9$;

$R^6$ and $R^7$ are independently at each occurrence selected from:

(1) H;

(2) $C_1$–$C_{10}$ alkyl, $C_3$–$C_{10}$ alkenyl, $C_3$–$C_{10}$ alkynyl, $C_2$–$C_8$ alkoxyalkyl, $C_3$–$C_6$ cycloalkyl, or $C_4$–$C_{12}$ cycloalkylalkyl, each optionally substituted with 1–6 substituents independently selected at each occurrence from $C_1$–$C_6$ alkyl, $C_3$–$C_6$ cycloalkyl, halogen, $C_1$–$C_4$ haloalkyl, cyano, nitro, $OR^{12}$, thiol, $S(O)_nR^9$, $COR^{12}$, $CO_2R^{12}$, $NR^8COR^{12}$, $NR^8CONR^{11}R^{12}$, $NR^8CO_2R^9$, $NR^{11}R^{12}$, and $CONR^{11}R^{12}$;

(3) aryl, aryl($C_1$–$C_4$ alkyl), heteroaryl or heteroaryl ($C_1$–$C_4$ alkyl), heterocyclyl, or heterocyclyl($C_1$–$C_4$ alkyl;

$R^8$ is independently at each occurrence selected from H, $C_1$–$C_4$ alkyl, C3–C8 alkenyl, $C_3$–$C_6$ cycloalkyl, or $C_4$–$C_7$ cycloalkylalkyl;

or phenyl or phenyl($C_1$–$C_4$ alkyl), each optionally substituted with 1–3 substitutents selected from C1–C4 alkyl, halogen, C1–C4, C1–C4 alkoxy, OH;

$R^9$ is independently at each occurrence selected from H, $C_1$–$C_4$ alkyl, $C_2$–$C_4$ alkoxyalkyl, $C_3$–$C_6$ cycloalkyl, $C_4$–$C_7$ cycloalkylalkyl;

or phenyl or phenyl($C_1$–$C_4$ alkyl), each optionally substituted with 1–3 substituents selected from C1–C4 alkyl, halogen, C1–C4 haloalkyl, C1–C4 alkoxy, OH;

$R^{10}$ is H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl), heteroaryl, heteroaryl($C_1$–$C_4$ alkyl), heterocyclyl, heterocyclyl ($C_1$–$C_4$ alkyl);

$R^{11}$ and $R^{12}$ are independently at each occurrence selected from H, $C_1$–$C_6$ alkyl, $C_3$–$C_6$ cycloalkyl, $C_4$–$C_7$ cycloalkylalkyl, or $C_1$–$C_4$ haloalkyl;

or phenyl or phenyl($C_1$–$C_4$ alkyl), each optionally substituted with 1–3 substituents selected from C1–C4 alkyl, halogen, C1–C4 haloalkyl, C1–C4 alkoxy, OH;

aryl is phenyl or naphthyl, each optionally substituted with 1 to 5 substituents independently selected at each occurrence from $R^{13}$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl, 2,3-dihydrobenzofuranyl, 2,3-dihydrobenzothienyl, or indazolyl, each optionally substituted with 1 to 4 substituents independently selected from at each occurrence $R^{13}$;

heterocyclyl is saturated or partially saturated heteroaryl, optionally substituted with 1 to 3 substituents independently selected at each occurrence from $R^{13}$;

$R^{13}$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, where $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl are optionally substituted with 1–3 substituents independently selected at each occurrence from $C_1$–$C_4$ alkyl, nitro, halogen, cyano, $NR^8R^9$, $NR^8COR^9$, $NR^8CO_2R^9$, $COR^9$, $OR^9$, $CONR^8R^9$, $NR^8CONR^8R^9$, $CO_2R^9$, thiol, or $S(O)_nR^9$ or nitro, halogen, cyano, $C_1$–$C_4$ haloalkyl, $NR^8R^9$, $NR^8COR^9$, $NR^8CO_2R^9$, $COR^9$, $OR^9$, $CONR^8R^9$, $NR^8CONR^8R^9$, $CO_2R^9$, thiol, or $S(O)_nR^9$; with the proviso that in formula (I) where $R^3$ is methyl, $R^2$ is not methyl.

2. A compound of claim 1 and isomers thereof, stereoisomeric forms thereof, or mixtures of stereoisomeric forms thereof, or pharmaceutically acceptable salts thereof wherein: $R^4$ is phenyl optionally substituted by 1 to 4 $R^5$ groups.

3. A compound of claim 1 and isomers thereof, stereoisomeric forms thereof, or mixtures of stereoisomeric forms thereof, or pharmaceutically acceptable salts thereof wherein: $R^1$ is selected from H, $C_1$–$C_6$ alkyl, $C_1$–$C_6$ haloalkyl, $C_3$–$C_6$ cycloalkyl or aryl.

4. A compound of claim 3 and isomers thereof, stereoisomeric forms thereof, or mixtures of stereoisomeric forms thereof, or pharmaceutically acceptable salts thereof wherein: $R^1$ is selected from H, $C_1$–$C_6$ alkyl, $C_1$–$C_6$ haloalkyl, $C_3$–$C_6$ cycloalkyl or aryl and $R^4$ is phenyl optionally substituted by 1 to 4 $R^5$ groups.

5. A compound of claim 1 and isomers thereof, stereoisomeric forms thereof, or mixtures of stereoisomeric forms thereof, or pharmaceutically acceptable salts thereof, selected from the group:

1-(2-chloro-4-trifluoromethyl)phenyl-5-ethyl-3-methyl-4-[1-(1-methyl)butane]imidazo[4,5-c]pyrazole;

1-(2-chloro-4-trifluoromethyl)phenyl-5-ethyl-4-[1-(1-ethyl)butane]-3-methylimidazo[4,5-c]pyrazole;

4-(n-butyl)-1-(2-chloro-4-bromo)phenyl-5-ethyl-3-methylimidazo[4,5-c]pyrazole;

1-(2-chloro-4-bromo)phenyl-5-ethyl-3-methyl-4-[1-(1-methyl)butane]imidazo[4,5-c]pyrazole;

1-(2-chloro-4-bromo)phenyl-5-ethyl-4-[1-(1-ethyl)butane]-3-methylimidazo[4,5-c]pyrazole;

5-ethyl-3-fluoromethyl-4-[1-(1-methyl)butane]-1-(2,4,6-trichloro)phenylimidazo[4,5-c]pyrazole;

5-ethyl-4-[1-(1-methyl)butane]-1-(2,4,6-trichloro)phenylimidazo[4,5-c]pyrazole;

1-(2,6-dichloro-4-bromo)phenyl-5-ethyl-4-[1-(1-ethyl)butane]-3-methylimidazo[4,5-c]pyrazole;

1-(2,4-dichloro)phenyl-5-ethyl-4-[1-(1-ethyl)butane]-3-methylimidazo[4,5-c]pyrazole;

1-(2,4-dichloro)phenyl-5-ethyl-3-methyl-4-[1-(1-methyl)butane]imidazo[4,5-c]pyrazole;

1-(2,4-dichloro)phenyl-5-ethyl-3-methyl-4-[1-(1,3-dimethyl)butane]imidazo[4,5-c]pyrazole;

1-(2,6-dichloro-4-bromo)phenyl-5-ethyl-3-methyl-4-[1-(1-methyl)butane]imidazo[4,5-c]pyrazole;

5-ethyl-4-[1-(1-ethyl)butane]-3-methyl-1-(2,4,5-trichloro)phenylimidazo[4,5-c]pyrazole;

5-ethyl-3-methyl-4-[1-(1-methyl)butane]-1-(2,4,5-trichloro)phenylimidazo[4,5-c]pyrazole;

5-ethyl-4-[1-(1-methyl)pentane]-3-methyl-1-(2,4,6-trichloro)phenylimidazo[4,5-c]pyrazole;

1-(2-bromo-4-isopropyl)phenyl-5-ethyl-4-[1-(1-ethyl)butane]-3-methylimidazo[4,5-c]pyrazole;

1-(2-bromo-4-isopropyl)phenyl-5-ethyl-3-methyl-4-[1-(1-methyl)butane]imidazo[4,5-c]pyrazole;

1-(2-bromo-4,6-dichloro)phenyl-5-ethyl-4-[1-(1-ethyl)butane]-3-methylimidazo[4,5-c]pyrazole;

1-(2-bromo-4,6-dichloro)phenyl-5-ethyl-3-methyl-4-[1-(1-methyl)butane]imidazo[4,5-c]pyrazole;

4-(n-butyl)-1-(2,6-dichloro-4-bromo)phenyl-5-ethyl-3-methylimidazo[4,5-c]pyrazole;

1-(2,6-dichloro-4-bromo)phenyl-5-ethyl-3-methyl-4-[1-(3-methyl)butane]imidazo[4,5-c]pyrazole;

1-(2,6-dichloro-4-bromo)phenyl-5-ethyl-4-[1-(2-ethyl)butane]-3-methylimidazo[4,5-c]pyrazole;

4-benzyl-1-(2,6-dichloro-4-bromo)phenyl-5-ethyl-3-methylimidazo[4,5-c]pyrazole; and 1-(2,6-dichloro-4-bromo)phenyl-4-(3,4-difluorobenzyl)-5-ethyl-3-methylimidazo[4,5-c]pyrazole.

6. A pharmaceutical composition comprising a pharmaceutically acceptable carrier and a therapeutically effective amount of a compound of claim 1.

7. A pharmaceutical composition comprising a pharmaceutically acceptable carrier and a therapeutically effective amount of a compound of claim 2.

8. A pharmaceutical composition comprising a pharmaceutically acceptable carrier and a therapeutically effective amount of a compound of claim 3.

9. A pharmaceutical composition comprising a pharmaceutically acceptable carrier and a therapeutically effective amount of a compound of claim 4.

10. A pharmaceutical composition comprising a pharmaceutically acceptable carrier and a therapeutically effective amount of a compound of claim 5.

11. A method of treating affective disorder, anxiety or depression, comprising: administering to the mammal a therapeutically effective amount of a compound of claim 1.

* * * * *